United States Patent [19]
Greenlee et al.

[11] Patent Number: 5,686,478
[45] Date of Patent: Nov. 11, 1997

[54] ENDOTHELIN ANTAGONISTS

[75] Inventors: William J. Greenlee, Teaneck; Thomas F. Walsh, Westfield, both of N.J.

[73] Assignee: Merck & Co. Inc., Rahway, N.J.

[21] Appl. No.: 267,981

[22] Filed: Jul. 7, 1994

Related U.S. Application Data

[63] Continuation-in-part of Ser. No. 95,126, Jul. 20, 1993, abandoned.

[51] Int. Cl.$^6$ .................... C07D 257/06; A61K 31/41
[52] U.S. Cl. .................... 514/382; 514/464; 514/466; 548/252; 548/253; 549/441; 549/444; 549/447
[58] Field of Search .................... 514/382, 464, 514/466; 548/252, 253; 549/441, 444, 447

[56] References Cited

U.S. PATENT DOCUMENTS

| | | |
|---|---|---|
| 3,499,008 | 3/1970 | Talet et al. |
| 4,268,512 | 5/1981 | Thominet et al. |
| 4,600,709 | 7/1986 | Ballenegger et al. |
| 4,748,272 | 5/1988 | Youssefyeh. |
| 5,082,838 | 1/1992 | Naka et al. |
| 5,114,918 | 5/1992 | Ishikawa et al. |
| 5,187,195 | 2/1993 | Oohata et al. |
| 5,326,776 | 7/1994 | Winn et al. |
| 5,334,598 | 8/1994 | Bagley et al. ................ 514/303 |
| 5,352,800 | 10/1994 | Bills et al. ................ 548/539 |
| 5,374,638 | 12/1994 | Dhanoa et al. ................ 514/326 |
| 5,401,745 | 3/1995 | Bagley et al. ................ 514/259 |
| 5,420,133 | 5/1995 | Dhanoa et al. ................ 514/259 |
| 5,559,105 | 9/1996 | Bryan et al. ................ 514/63 |

FOREIGN PATENT DOCUMENTS

| | | |
|---|---|---|
| 436 189 A1 | 7/1990 | European Pat. Off. |
| 405 421 A2 | 1/1991 | European Pat. Off. |
| 457 195 A2 | 11/1991 | European Pat. Off. |
| 460 679 A2 | 12/1991 | European Pat. Off. |
| 496452 A1 | 7/1992 | European Pat. Off. |
| 510 526 A1 | 10/1992 | European Pat. Off. |
| 526 642 A1 | 2/1993 | European Pat. Off. |
| 526 708 A1 | 2/1993 | European Pat. Off. |
| 558 258 A1 | 9/1993 | European Pat. Off. |
| 562 599 A1 | 9/1993 | European Pat. Off. |
| 569 193 A1 | 11/1993 | European Pat. Off. |
| 601 386 A1 | 6/1994 | European Pat. Off. |
| 3829431 A1 | 3/1990 | Germany. |
| 06122625 | 6/1994 | Japan. |
| 2 259 540A | 3/1993 | United Kingdom. |
| WO 92 00952 | 1/1992 | WIPO. |
| WO 92/15321 | 9/1992 | WIPO. |
| WO 92/20706 | 11/1992 | WIPO. |
| WO 93 08799 | 5/1993 | WIPO. |
| WO 93 13052 | 7/1993 | WIPO. |
| WO 93 13069 | 7/1993 | WIPO. |
| WO 93 23404 | 11/1993 | WIPO. |
| WO 94 14796 | 12/1993 | WIPO. |
| WO 94 02474 | 2/1994 | WIPO. |
| WO 94 14434 | 7/1994 | WIPO. |

OTHER PUBLICATIONS

Chem. Pharm. Bulletin, vol. 31, No. 9, pp. 3039–3055 (1983), by Ishii, et al.

"Antihypertensive Effects of the Endothelin Receptor Antagonist BQ–123 in Conscious Spontaneously Hypetensive Rats" E. H. Ohlstein, et al. Journal of Cardiovascular Pharmacology, vol. 22, (Suppl. 8), 1993, pp. S321–S324.

"Direct and Sympathetically Mediated Vasoconstriction in Essential Hypertension" W. G. Haynes, et al. J. Clin. Invest., vol. 94, Oct. 1994, pp. 1359–1364.

"Role of Endothelin in Hypertension" B.K. Krämer, et al. Clin. Investig., vol. 72, (1994), pp. 88–93.

"Potential Role of Endothelin in Hypertension" T. F. Lüscher, et al. Hypertension, vol. 21, No. 6, Part 1, Jun. 1993, pp. 752–757.

"BQ123, An ET(A) Receptor Antagonist, Attenuates Hypoxic Pulmonary–Hypertension in Rats" Bonvallet, S. T., et al. American Journal of Physiology, vol. 266, No. 4, (Apr. 1994), pp. H1327–H1331.

"Endothelin–A Receptor Antagonist Prevents Acute Hypoxia–Induced Pulmonary–Hypertension in the Rat" Oparil, S., et al. American Journal of Physiology–Lung Cellular and Molecular Physiology, vol. 12., No. 1, (Jan. 1995), pp. L95–L100.

"Protection from Pulmonary Hypertension with an Orally Active Endothelin Receptor Antagonist in Hypoxic Rats" American Journal of Physiology–Heart and Circulatory Physiology, vol. 37, No. 2, (Feb. 1995), pp. H828–H835.

(List continued on next page.)

Primary Examiner—Joseph McKane
Assistant Examiner—Richard S. Myers
Attorney, Agent, or Firm—Valerie J. Camara; Mark R. Daniel

[57] ABSTRACT

Novel derivatives of the general structural Formula I

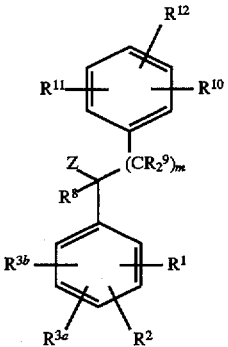

have endothelin antagonist activity and are therefore useful in treating cardiovascular disorders, such as hypertension, pulmonary hypertension, postischemic renal failure, vasospasm, cerebral and cardiac ischemia, myocardial infarction, endotoxic shock, benign prostatic hyperplasia, complications of diabetes, migraine, bone resorption, and inflammatory diseases, including Raynaud's disease and asthma.

20 Claims, No Drawings

OTHER PUBLICATIONS

"Endothelial Dysfunction and Remodeling of the Pulmonary Ciculation in Chronic Hypoxic Pulmonary–Hypertension" Dinhxuan, A.T., et al. ACP–Applied Cardiopulmonary Pathophysiology, vol. 5, No. 2, (1994), pp., 93–99.

"Cyclosporine–Induced Elevation in Circulating Endothelin–1 in Patients with Solid–Organ Transplants" Grieff, M., et al. Transplantation vol. 54, No. 4, (Oct. 1993), pp. 880–884.

"Cyclosporine–Induced Hypertension After Transplantation" Textor, S. C., et al. Mayo Clinical Proceedings, vol. 69, (1994), pp. 1182–1193.

"A Role for Endogenous Endothelin–1 in Neointimal Formation After Rat Carotid Artery Balloon Angioplasty" Douglas S. A., et al. Circulation Research, vol. 75, (1994), pp. 190–197.

"[125I]–Endothelin–1 Binding to Vasa Vasorum and Regions of Neovascularization in Human and Porcine Blood Vessels: A Possible Role for Endothelin in Intimal Hyperplasia and Atheroscelerosis" Dashwood, M.R., et al. Journal of Cardiovascular Pharmacology, vol. 22, (Suppl. 8), (1993), pp. S343–S347.

"The Endothelin–1 Receptor Antagonist BQ–123 Reduces Infarct Size in a Canine Model of Coronary Occlusion and Reperfusion" Grover, G. J., et al. Cardiovascular Research, vol. 75, No. 9, (Sep. 1993), pp. 1613–1618.

"The Effects of the Endothelin ETa Receptor Antagonist, FR139317, on Infarct Size in a Rabbit Model of Acute Myocardial Ischemia and Reperfusion" McMurdo, L., et al. British Journal of Pharmacology, (1994), vol. 112, pp. 75–80.

"Vasodilator Effects of the Endothelin–1 Receptor Antagonist Bosentan in Patients with Severe Chronic Heart Failure" Kiowski, W., et al. Journal Am. College of Cardiology, Feb. 1995, pp. 296A, abstract No. 779–1.

"Nonpeptide Endothelin Receptor Antagonists. III. Effect of SB 209670 and BQ123 on Acute Renal Failure in Anesthetized Dogs" Brooks, D. P., et al. Journal of Pharmacology and Experimental Therapeutics, vol. 271, (1994), pp. 769–775.

"Reversal of Postischemic Acute Renal Failure with a Selective Endothelin $_A$ Receptor Antagonist in the Rat" Gellai, M., et al. Journal of Clinical Investigator, vol. 93, (1994), pp. 900–906.

"Effects of BQ–123 on Renal–Function and Acute Cyclosporine Induced Renal Dysfunction", Kivlighn, S.D. et al., Kidney International, vol. 45, No. 1, (Jan. 1994), pp. 131–136.

"Endotoxin–Mediated Changes In Plasma Endothelin Concentrations, Renal Endothelin Receptor And Renal–Function", Nambi, P. et al., vol. 48, No. 3, (Mar. 1994), pp. 147–156.

"Effect of Total–Body Cold–Exposure on Plasma–Concentrations of Vonwillebrand–Factor, Endothelin–1 and Thrombomodulin in Systemic Lupus–Erythematosus Patients with or without Raynauds–Phenomeon", Matsuda, J., et al. Acta Haematologica, vol. 88, No. 4, (1992), pp. 189–193.

"Localization of Endothelin–1 and Its Binding–Sites in Scleroderma Skin" Vancheeswaran, R., et al. Journal of Rheumatology, vol. 21, No. 7, (Jul. 1994), pp. 1268–1276.

"Increased Endothelin–1 Production in Fibroblasts Derived from Patients with Systemic–Sclerosis" Kawaguchi, Y., et al. Annals of the Rheumatic Diseases, vol. 53, No. 8, (Aug. 1994), pp. 506–510.

"Characterization of Endothelin–Binding Sites in Human Skin and Their Regulation in Primary Raynauds–Phenomenon and Systemic–Sclerosis" Knock G.A., et al. Journal of Investigative Dermatology, vol. 101, No. 1, (Jul. 1993), pp. 73–78.

"Raynaud Phenomenon" Coffman, J.D., et al. Current Opinion in Cardiology, vol. 8, No. 5, (Sep. 1993), pp. 821–828.

"Parameters of Vascular Function in Idiopathic and Silica–Induced Systemic–Sclerosis" Haustein, U.F., et al. Hautarzt, vol. 44, No. 11, (Nov. 1993), pp. 717–722.

"Circulating Endothelin–1 Levels in Systemic–Sclerosis Subsets—A Marker of Fibrosis or Vascular Dysfunction" Vancheeswaran, R., et al. Journal of Rheumatology, vol. 21, No. 10, (Oct. 1994).

"Endothelin and Collagen Vascular Disease: A Review with Special Reference to Raynauds–Phenomenon and Systemic–Sclerosis" Yamane, K. Internal Medicine, vol. 33, No. 10, (Oct. 1994), pp. 579–582.

"A Pathogenic Role for Endothelin in Raynauds–Phenomenon" Bottomley, W., et al. Acta Dermato–Venereologica, vol. 74, No. 6, (Nov. 1994), pp. 433–434.

"BQ 123, A Peptidic Endothelin ETA Receptor Antagonist, Prevents the Early Cerebral Vasospasm Following Subarachnoid Hemorrhage After Interacisternal but no Intravenous–Injection" Clozel, M., et al. Life Sciences, vol. 52, No. 9, (1993), pp. 825–834.

"An Endothelin ET(A) Receptor Antagonist, FR139317, Ameliorates Cerebral Vasospasm in Dogs" Nirei, H., et al. Life Sciences, vol. 52, No. 23, (1993), pp. 1869–1874.

"Reversal of Subarachnoid Hemorrhage–Induced Vasoconstriction with an Endothelin Receptor Antagonist" Foley, P.L. et al. Neurosurgery, vol. 34, No. 1, (Jan. 1994), pp. 108–113.

"Endothelin Levels Increase in Rat Focal and Global–Ischemia" Barone, F.C., et al. Journal of Cerebral Blood Flow and Metabolism, vol. 14, No. 2, (Mar. 1994), pp. 337–342.

"Endothelin ET(A) and ET(B) Receptors in Subarachnoid Hemorrhage–Induced Cerebral Vasospasm" Zuccarello, M., et al. European Journal of Pharmacology, vol. 259, No. 1, (Jun. 23 1994), pp. R1–R2.

"Changes of Endothelin Concentration in Cerebrospinal–Fluid and Plasma of Patients with Aneurysmal Subarachnoid Hemorrhage" Shirakami, G., et al. Acta Anaesthesiologica Scandinavica, vol. 38, No. 5, (Jul. 1994), pp. 457–461.

"Prevention of Delayed Vasospasm by an Endothelin ET(A) Receptor Antagonist, BQ–123—Change of ET(A) Receptor Messenger–RNA Expression in a Canine Subarachnoid Hemorrhage Model" Itoh, S., et al. Journal fo Neurosurgery, vol. 81, No. 5, (Nov. 1994), pp. 759–764.

"Endothelin Concentrations in Patients with Aneurysmal Subarachnoid Hemorrhage—Correlation with Cerebral Vasopspasm, Delayed Ischemic Neurological Deficits, and Volume of Hematoma" Seifert V., et al. Journal of Neurosurgery, vol. 82, No. 1, (Jan. 1995), pp. 55–62.

ENDOTHELIN ANTAGONISTS

RELATED APPLICATIONS

This application is a continuation in part application of U.S. Ser. No. 08/095,126 filed Jul. 20, 1993, now abandoned.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1-3]

Endothelin-1 (ET-1) is one of three recently identified potent vasoconstricting peptides which also includes endothelin-2 (ET-2) and endothelin-3 (ET-3) whose sequences differ from ET-1 by two and six amino acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma compared to normal levels.[5-8]

An experimental model of cerebral vasospasm and a second model of acute renal failure have led to the conclusion that endothelin is one of the mediators causing cerebral vasospasm following a subarachnoid hemorrhage, and renal failure.[9-10]

Endothelin was also found to control the release of many physiological substances such as renin, atrial natriuretic peptide, endothelium-derived relaxing factor (EDRF), thromboxane $A_2$,[14] prostacyclin, norepinephrine, angiotensin II and substance P.[11-16] Further, endothelin causes contraction of the smooth muscle of the gastrointestinal tract and the uterine smooth muscle.[17-19] Endothelin has also been shown to promote the growth of rat vascular smooth muscle cells which would suggest a possible relevance to arterial hypertrophy.[20]

Endothelin receptors are present in high concentration in the peripheral tissues and also in the central nervous system, and cerebral administration of endothelin has been shown to induce behavioral changes in animals, suggesting that endothelin may play an important role in controlling neural functions.[21]

Endotoxin has been shown to promote the release of endothelin. This finding has suggested that endothelin is an important mediator for endotoxin-induced diseases.[22-23]

A study has shown that cyclosporin added to a renal cell culture, increased endothelin secretion.[24] Another study has shown that administration of cyclosporin to rats, led to a decrease in the glomerular filtration rate and an increase in the blood pressure, in association with a remarkable increase in the circulating endothelin level. This cyclosporin-induced renal failure can be suppressed by the administration of anti-endothelin antibody.[25] These studies suggest that endothelin is significantly involved in the pathogenesis of cyclosporin-induced renal disease.

A recent study in patients with congestive heart failure demonstrated a good correlation between the elevated levels of endothelin in the plasma and the severity of the disease.[26]

Endothelin is an endogenous substance which directly or indirectly (through the controlled release of various other endogenous substances) induces sustained contraction of vascular or non-vascular smooth muscles. Its excess production or excess secretion is believed to be one of the factors responsible for hypertension, pulmonary hypertension, Raynaud's disease, bronchial asthma, acute renal failure, myocardial infarction, angina pectoris, arteriosclerosis, cerebral vasospasm and cerebral infarction. See A. M. Doherty, *Endothelin: A New Challenge*. J. Med. Chem., 35, 1493–1508 (1992).

Substances which specifically inhibit the binding of endothelin to its receptor are believed to block the physiological effects of endothelin and are useful in treating patients with endothelin related disorders.

The novel compounds of the present invention are useful as a non-peptidic endothelin antagonists, and have not been disclosed in any issued patents or published patent applications. Among the published patent applications disclosing linear and cyclic peptidic compounds as endothelin antagonists are the following: Fujisawa in European Patent Application EP-457,195 and Patent Cooperation Treaty (PCT) International Application No. WO 93/10144, Banyu in EP-436,189 and 460,679, Immunopharmaceutics Inc. in WO 93/225580, Warner Lambert Co. WO 92/20706 and Takeda Chemical Ind. in EP-528,312, EP-543,425, EP-547, 317 and WO 91/13089.

Fujisawa has also disclosed two nonpeptidic endothelin antagonist compounds: anthraquinone derivatives produced by a fermentation process using Streptomyces sp. No. 89009 in EP-405,421 and U.S. Pat. No. 5,187,195; and a 4-phenoxyphenol derivative produced by a fermentation process using *Penicillium citreonigrum* F-12880 in a UK Patent Application GB 2259450. Shionogi and Co. has also disclosed nonpeptidic endothelin antagonist triterpene compounds which were produced by a fermentation process using *Myrica cerifera* in WO 92/12991.

Among the non-peptidic endothelin antagonist compounds which are known in the patent literature are: 1) a series of substituted (1,4-quinolinoxy) methylbiphenylcarboxylic acids disclosed by Roussel-Uclaf in EP-498,723; 2) a series of of N-(4-pyrimidinyl) benzenesulfonamides with different substitution patterns from Hoffmann-La Roche published in EP-510,526, EP-526,708 and EP-601,386; 3) a series of naphthalenesulfonamides and benzenesulfonamides disclosed by E. R. Squibb & Sons in EP-558,258 and EP-569,193, respectively; 4) a series of compounds represented by 3-(3-indolylmethyl)-1,4-diaza-2,5-dioxobicyclo[4.3.0]nonane-9-carboxylic acid from ImmunoPharmaceutics Inc. in WO 93/23404; 5) a series of fused [1,2,4]thiadiazoles substituted with an iminosulfonyl substituent from Takeda Chemical Ind. has been disclosed in EP-562,599; and 6) a series of indane and indene derivatives from SmithKline Beecham Corp. disclosed in WO 93/08779; and a series of related phenylalkyl derivatives from SmithKline Beecham disclosed in WO 94/02474.

REFERENCES

1 Nature, 332, 411–415 (1988).
2 FEBS Letters, 231, 440–444 (1988).
3 Biochem. Biophys. Res. Commun. 154, 868–875 (1988).
4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).
8 The Lancet, ii, 207 (1990) and The Lancet, ii, 747–748 (1989).
9 Japan. Soc. Cereb. Blood Flow & Metabol. 1, 73 (1989).

10 J. Clin. Invest., 83, 1762–1767 (1989).
11 Biochem. Biophys. Res. Comm. 157, 1164–1168 (1988).
12 Biochem. Biophys. Res. Comm. 155, 167–172 (1989).
13 Proc. Natl. Acad. Sci. U.S.A., 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).
18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

SUMMARY OF THE INVENTION

This invention is concerned with non-peptidic endothelin receptor antagonists represented by the compound of Formula I, pharmaceutical compositions containing these compounds, as well as combination therapies which include a compound of the present invention. The compounds of the present invention are therapeutic agents particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, benign prostatic hyperplasia, complications of diabetes, migraine, bone resorption inflammatory bowel diseases, including Crohn's disease and ulcerative colitis, as well as other inflammatory diseases, or endotoxic shock caused by or associated with endothelin.

This invention further constitutes a method for antagonizing endothelin receptors in a mammal, including humans, which comprises administering to a mammal in need of such treatment an effective amount of a compound of Formula I.

DETAILED DESCRIPTION OF THE INVENTION

This invention is concerned with novel compounds of structural Formula I:

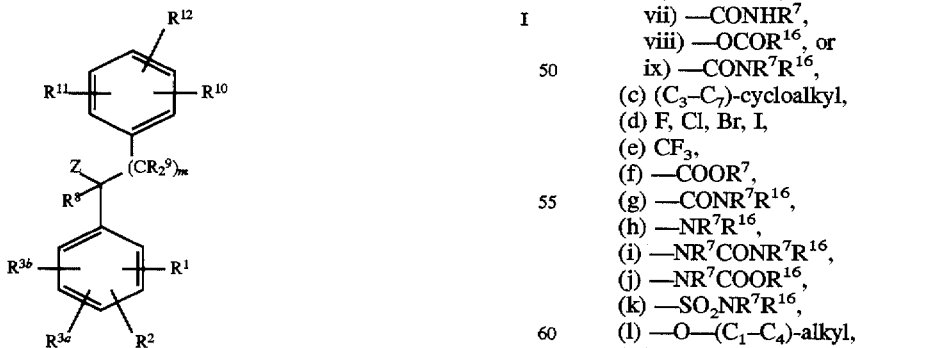

I or a pharmaceutically acceptable salt thereof, wherein:

$R^1$, $R^2$, $R^{3a}$ and $R^{3b}$ are independently:
  (a) H,
  (b) F, Cl, Br, or I,
  (c) —$NO_2$,
  (d) —$NH_2$,
  (e) —NH($C_1$–$C_4$)-alkyl,
  (f) —N[($C_1$–$C_4$)-alkyl]$_2$,
  (g) —$SO_2NHR^7$,
  (h) —$CF_3$,
  (i) ($C_1$–$C_4$)-alkyl,
  (j) —$OR^7$,
  (k) —S(O)$_n$—($C_1$–$C_4$)-alkyl,
  (l) —NHCO—($C_1$–$C_4$)-alkyl,
  (m) —NHCO—O($C_1$–$C_4$)-alkyl,
  (n) —$CH_2$O—($C_1$–$C_4$)-alkyl,
  (o) —O—($CH_2$)$_x$—$OR^7$,
  (p) —$CONR^7R^{16}$, or
  (q) —$COOR^7$;

m is: 1 or 2;

n is: 0, 1 or 2;

x is: 2, 3, or 4;

$R^1$ and $R^2$ on adjacent carbon atoms can be joined together to form a ring structure:

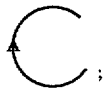;

A represents:
  a) —Y—C($R^4$)=C($R^5$)—,
  b) —Y—C($R^4$)=N—,
  c) —Y—N=C($R^4$)—,
  d) —Y—[C($R^6$)($R^6$)]$_s$—Y—,
  e) —Y—C($R^6$)($R^6$)—C($R^6$)($R^6$)—,
  f) —C($R^4$)=C($R^5$)—Y—,
  g) —N=C($R^4$)—Y—,
  h) —C($R^6$)($R^6$)—C($R^6$)($R^6$)—Y—, or
  i) —C($R^4$)=C($R^5$)—C($R^4$)=C($R^5$)—;

s is: 1 or 2;

Y is: —O—, —S(O)$_n$— and $NR^7$;

$R^4$ and $R^5$ are independently:
  (a) H,
  (b) ($C_1$–$C_6$)-alkyl or ($C_2$–$C_6$)-alkenyl each of which is unsubstituted or substituted with one or two substituents selected from the group consisting of:
    i) —OH,
    ii) —O—($C_1$–$C_4$)-alkyl,
    iii) —S(O)$_n$—($C_1$–$C_4$)-alkyl,
    iv) —$NR^7$—($C_1$–$C_4$)-alkyl,
    v) —$NHR^7$,
    vi) —$COOR^7$,
    vii) —$CONHR^7$,
    viii) —$OCOR^{16}$, or
    ix) —$CONR^7R^{16}$,
  (c) ($C_3$–$C_7$)-cycloalkyl,
  (d) F, Cl, Br, I,
  (e) $CF_3$,
  (f) —$COOR^7$,
  (g) —$CONR^7R^{16}$,
  (h) —$NR^7R^{16}$,
  (i) —$NR^7CONR^7R^{16}$,
  (j) —$NR^7COOR^{16}$,
  (k) —$SO_2NR^7R^{16}$,
  (l) —O—($C_1$–$C_4$)-alkyl,
  (m) —S(O)$_n$—($C_1$–$C_4$)-alkyl, or
  (n) —$NHSO_2R^{16}$;

$R^6$ is:
  (a) H,
  (b) F, or
  (c) ($C_1$–$C_4$)-alkyl unsubstituted or substituted with one of the following substituents:

i) —OH,
ii) —NR$^7$R$^{16}$,
iii) —COOR$^7$,
iv) —CONHR$^7$, or
v) —CONR$^7$R$^{16}$;

R$^7$ is:
(a) H,
(b) (C$_1$–C$_6$)-alkyl,
(c) phenyl;
(d) benzyl, or
(e) (C$_3$–C$_7$)-cycloalkyl;

R$^8$ is:
(a) H,
(b) (C$_1$–C$_6$)-alkyl, unsubstituted or substituted with a substituent selected from the group consisting of:
  i) -phenyl,
  ii) —(C$_3$–C$_7$)-cycloalkyl,
  iii) —NR$^7$R$^{16}$,
  iv) -morpholin-4-yl,
  v) —OH,
  vi) —CO$_2$R$^7$, or
  vii) —CON(R$^7$)$_2$,
(c) phenyl, unsubstituted or substituted with a substituent selected from the group consisting of:
  i) (C$_1$–C$_4$)-alkyl,
  ii) —O—(C$_1$–C$_4$)-alkyl,
  iii) —CONR$^7$R$^{16}$,
  iv) F, Cl, Br or I,
  v) —COOR$^7$, or
  vi) 2,3-, or 3,4-methylenedioxy;

R$^9$ is:
(a) H,
(b) (C$_1$–C$_6$)-alkyl, unsubstituted or substituted with a substituent selected from the group consisting of:
  i) -phenyl,
  ii) —(C$_3$–C$_7$)-cycloalkyl,
  iii) —NR$^7$R$^{16}$,
  iv) —OH,
  v) —O—(C$_1$–C$_4$)-alkyl,
  vi) —CF$_3$,
  vii) —COOR$^7$,
  viii) —S(O)$_n$—(C$_1$–C$_4$)-alkyl, or
  ix) —CON(R$^7$)$_2$;
(c) (C$_3$–C$_7$)-cycloalkyl,
(d) F, Cl, Br, I,
(e) —COOR$^7$,
(f) —CON(R$^7$)$_2$,
(g) -perfluoro-(C$_1$–C$_4$)-alkyl,
(h) —O—(CH$_2$)$_m$—OR$^7$, or
(i) —S(O)$_n$—(C$_1$–C$_4$)-alkyl;

R$^{10}$ and R$^{11}$ are independently:
(a) H,
(b) (C$_1$–C$_6$)-alkyl, unsubstituted or substituted with (C$_3$–C$_7$)-cycloalkyl,
(c) (C$_2$–C$_6$)-alkenyl,
(d) (C$_2$–C$_6$)-alkynyl,
(e) Cl, Br, F, I,
(f) (C$_1$–C$_6$)-alkoxy,
(g) when R$^{10}$ and R$^{11}$ are on adjacent carbons, they can be joined to form a phenyl ring,
(h) perfluoro-(C$_1$–C$_6$)-alkyl,
(i) (C$_3$–C$_7$)-cycloalkyl, unsubstituted or substituted with (C$_1$–C$_6$)-alkyl,
(j) phenyl,
(k) (C$_1$–C$_6$)-alkyl-S(O)$_n$—(CH$_2$)$_n$—,
(l) hydroxy-(C$_1$–C$_6$)-alkyl,
(m) —CF$_3$,
(n) —CO$_2$R$^7$,
(o) —OH,
(p) —NR$^7$R$^{16}$,
(q) —[(C$_1$–C$_6$)-alkyl]NR$^7$R$^{16}$,
(r) —NO$_2$,
(s) —(CH$_2$)$_n$—SO$_2$—N(R$^7$)$_2$,
(t) —NR$^7$CO—(C$_1$–C$_4$)-alkyl,
(u) —CON(R$^7$)$_2$, or
(v) when R$^{10}$ and R$^{11}$ are on adjacent carbons, they can join together to form a ring, where R$^{10}$ and R$^{11}$ are represented by —O—CH$_2$—O—;

R$^{12}$ is:
(a) H
(b) (C$_1$–C$_6$)-alkyl, unsubstituted or substituted with one or two substituents selected from the group consisting of:
  i) —OH,
  ii) —O—(C$_1$–C$_4$)-alkyl,
  iii) —O—(C$_1$–C$_4$)-cycloalkyl,
  iv) —S(O)$_n$—(C$_1$–C$_4$)-alkyl,
  iv) —NR$^7$—(C$_1$–C$_4$)-alkyl,
  v) —NR$^7$R$^{16}$,
  vi) —COOR$^7$,
  vii) —CONHR$^7$,
  viii) —OCOR$^{16}$,
  ix) —CONR$^7$R$^{16}$,
  x) —NR$^7$CONR$^7$R$^{16}$,
  xi) —NR$^7$COOR$^{16}$,
  xii) —C(R$^6$)(OH)—C(R$^6$)(R$^7$)(OH), or
  xiii) —SO$_2$NR$^7$R$^{16}$,
(c) (C$_3$–C$_7$)-cycloalkyl,
(d) —C(R$^6$)(OH)—C(R$^6$)(R$^7$)(OH),
(e) -perfluoro-(C$_1$–C$_4$)-alkyl,
(f) —OR$^7$,
(g) —COOR$^{13}$,
(h) —COR$^{16}$,
(i) —CONR$^7$R$^{16}$,
(j) —CONHSO$_2$R$^{16}$;
(k) —NO$_2$,
(l) —NH$_2$,
(m) —NR$^7$R$^{16}$,
(n) —NR$^7$CONR$^7$R$^{16}$,
(o) —NR$^7$COOR$^{16}$,
(p) —NR$^7$COR$^{16}$,
(q) —NR$^7$CONHSO$_2$R$^{16}$,
(r) —NR$^7$SO$_2$R$^{16}$,
(s) —NR$^7$SO$_2$NH$_2$,
(t) —NR$^7$SO$_2$NHR$^{16}$,
(u) —NR$^7$SO$_2$N(R$^{16}$)$_2$,
(v) —NR$^7$SO$_2$NHCOR$^{16}$,
(w) —SO$_2$NR$^7$R$^{16}$,
(x) —S(O)$_2$—NR$^7$COR$^{16}$,
(y) —S(O)$_2$—NR$^7$COOR$^{16}$,
(z) —S(O)$_2$—NR$^7$CONHR$^{16}$,
(aa) —S(O)$_2$—NR$^7$CONH$_2$, or
(ab) —S(O)$_n$—(C$_1$–C$_4$)-alkyl;

Z is:
(a) —CO$_2$R$^{13}$,
(b) —CONH-(tetrazol-5-yl),
(c) —CONHSO$_2$-phenyl, wherein phenyl is unsubstituted or substituted with one or two substituents selected from the group consisting of:
  i) (C$_1$–C$_4$)-alkyl,
  ii) —O—(C$_1$–C$_4$)-alkyl,
  iii) —CONR$^7$R$^{16}$,
  iv) F, Cl, Br or I,
  v) —COOR$^7$, vi) $(C_1-C_4)$-perfluoroalkyl,
vii) $(C_3-C_7)$-cycloalkyl,
viii) $NR^7R^{16}$,
ix) $SO_2NR^7R^{16}$,
x) hydroxy, or
xi) 2,3-, or 3,4-methylenedioxy;
(d) —$CONHSO_2$—$(C_1-C_8)$-alkyl, wherein the alkyl group is unsubstituted or substituted as defined in $R^4(b)$,
(e) —$CONHSO_2$—$(C_1-C_4)$-perfluoroalkyl,
(f) —$CONHSO_2$—$(C_3-C_7)$-cycloalkyl,
(g) —$CONHSO_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl, quinolinyl, or carbazolyl, unsubstituted or substituted with $(C_1-C_6)$-alkyl,
(h) -tetrazol-5-yl,
(i) —$CONHSO_2NH$-phenyl, wherein phenyl is unsubstituted or substituted with one or two substituents selected from the group consisting of:
 i) $(C_1-C_4)$-alkyl,
 ii) —O—$(C_1-C_4)$-alkyl,
 iii) —$CONR^7R^{16}$,
 iv) F, Cl, Br or I,
 v) —$COOR^7$,
 vi) $(C_1-C_4)$-perfluoroalkyl,
 vii) $(C_3-C_7)$-cycloalkyl,
 viii) $NR^7R^{16}$,
 ix) $SO_2NR^7R^{16}$,
 x) hydroxy, or
 xi) 2,3-, or 3,4-methylenedioxy;
(j) —$CONHSO_2NH$—$(C_1-C_8)$-alkyl, wherein the alkyl group is unsubstituted or substituted as defined in $R^4(b)$,
(k) —$CONHSO_2NH$—$(C_1-C_4)$-perfluoroalkyl,
(l) —$CONHSO_2NH$—$(C_3-C_7)$-cycloalkyl,
(m) —$CONHSO_2NH$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl, quinolinyl, or carbazolyl, unsubstituted or substituted with $(C_1-C_6)$-alkyl;
(n) —$SO_2NHCO$-phenyl, wherein phenyl is as defined in Z(c) above,
(o) —$SO_2NHCO$—$(C_1-C_8)$-alkyl, wherein the alkyl group is unsubstituted or substituted as defined in $R^4(b)$,
(p) —$SO_2NHCO$-$(C_1-C_4)$-perfluoroalkyl,
(q) —$SO_2NHCO$-heteroaryl, wherein heteroaryl is as defined in Z(g) above,
(r) —$SO_2NHCON(R^{16})_2$ wherein the $R^{16}$ groups are the same or different,
(r) —$SO_2NHCOOR^{16}$,
(o) —$PO(OR^7)_2$, wherein the $R^7$ groups are the same or different, or
(p) —$PO(R^{16})OR^7$;
$R^{13}$ is:
(a) H,
(b) $(C_1-C_6)$-alkyl,
(c) $CHR^{14}$—O—$COR^{15}$,
(d) $CH_2CH_2$—$N[(C_1-C_2)$-alkyl$]_2$,
(e) $CH_2CH_2$—$N[CH_2CH_2]_2O$,
(f) $(CH_2CH_2O)_y$—O—$[(C_1-C_4)$-alkyl], wherein y is 1 or 2,
(g) phenyl, naphthyl, $CH_2$-phenyl or $CH_2$-naphthyl, where phenyl or naphthyl is substituted or unsubstituted with $CO_2$—$(C_1-C_6)$-alkyl,

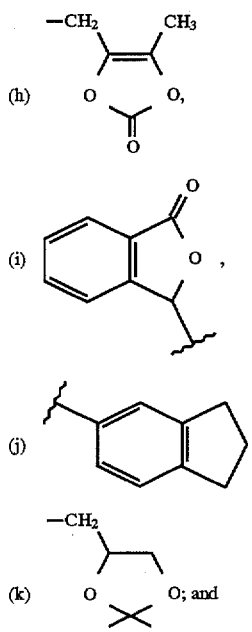

$R^{14}$ and $R^{15}$ independently are $(C_1-C_6)$-alkyl or phenyl; and

R16 is
(a) —$(C_1-C_6)$-alkyl,
(b) —$(C_1-C_4)$-perfluoroalkyl,
(c) —$(C_1-C_4)$-polyfluoroalkyl,
(d) -phenyl, unsubstituted or substituted with a substituent selected from the group consisting of:
 i) $(C_1-C_4)$-alkyl,
 ii) —O—$(C_1-C_4)$-alkyl,
 iii) —$CONR^7R^{16}$,
 iv) F, Cl, Br or I,
 v) —$COOR^7$,
(e) —$(C_1-C_4)$-alkyl-phenyl, wherein the phenyl is unsubstituted or substituted with a substituent selected from the group consisting of:
 i) $(C_1-C_4)$-alkyl,
 ii) —O—$(C_1-C_4)$-alkyl,
 iii) —$CONR^7R^{16}$
 iv) F, Cl, Br or I,
 v) —$COOR^7$, or
(f) —$(C_3-C_7)$-cycloalkyl.

An embodiment of the invention is the compound of structural Formula II:

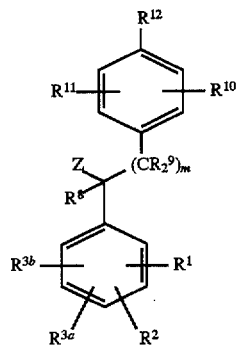

or a pharmaceutically acceptable salt thereof, wherein:

$R^1$, $R^2$, $R^{3a}$ and $R^{3b}$ are independently:
(a) H,
(b) F, Cl, Br, or I,
(c) —$NO_2$,
(d) —$NH_2$,
(e) —$NH(C_1-C_4)$-alkyl,
(f) —$N[(C_1-C_4)$-alkyl$]_2$,
(g) —$SO_2NHR^7$,
(h) —$CF_3$,
(i) —$(C_1-C_4)$-alkyl,
(j) —$OR^7$,
(k) —$S(O)_n$—$(C_1-C_4)$-alkyl,
(l) —NHCO—$(C_1-C_4)$-alkyl,
(m) —NHCO—$O(C_1-C_4)$-alkyl,
(n) —$CH_2O$—$(C_1-C_4)$-alkyl,
(o) —O—$(CH_2)_x$—$OR^7$,
(p) —$CONR^7R^{16}$, or
(q) —$COOR^7$;

x is 2, 3, or 4;

m is: 1 or 2;

n is 0, 1 or 2;

$R^1$ and $R^2$ on adjacent carbon atoms can be joined together to form a ring structure:

A represents:
a) —Y—$C(R^4)$=$C(R^5)$—,
b) —Y—$C(R^4)$=N—,
c) —Y—N=$C(R^4)$—,
d) —Y—$[C(R^6)(R^6)]_s$—Y—,
e) —Y—$C(R^6)(R^6)$—$C(R^6)(R^6)$—,
f) —$C(R^4)$=$C(R^5)$—Y—,
g) —N=$C(R^4)$—Y—,
h) —$C(R^6)(R^6)$—$C(R^6)(R^6)$—Y—, or
i) —$C(R^4)$=$C(R^5)$—$C(R^4)$=$C(R^5)$—;

s is 1 or 2,

Y is —O—, —$S(O)_n$— and $NR^7$;

$R^4$ and $R^5$ are independently:
(a) H,
(b) $(C_1-C_6)$-alkyl or $(C_2-C_6)$-alkenyl each of which is unsubstituted or substituted with one or two substituents selected from the group consisting of:
  i) —OH,
  ii) —O—$(C_1-C_4)$-alkyl,
  iii) —$S(O)_n$—$(C_1-C_4)$-alkyl,
  iv) —$NR^7$—$(C_1-C_4)$-alkyl,
  v) —$NHR^7$,
  vi) —$COOR^7$,
  vii) —$CONHR^7$,
  viii) —$OCOR^{16}$, or
  ix) —$CONR^7R^{16}$,
(c) $(C_3-C_7)$-cycloalkyl,
(d) F, Cl, Br, I,
(e) $CF_3$,
(f) —$COOR^7$,
(g) —$CONR^7R^{16}$,
(h) —$NR^7R^{16}$,
(i) —$NR^7CONR^7R^{16}$,
(j) —$NR^7COOR^{16}$,
(k) —$SO_2NR^7R^{16}$,
(l) —O—$(C_1-C_4)$-alkyl,
(m) —$S(O)_n$—$(C_1-C_4)$-alkyl, or
(n) —$NHSO_2R^{16}$;

$R^6$ is:
(a) H,
(b) F, or
(c) $(C_1-C_4)$-alkyl unsubstituted or substituted with one or two substituents selected from the group consisting of:
  i) —OH,
  ii) —$NR^7R^{16}$,
  iii) —$COOR^7$,
  iv) —$CONHR^7$, or
  v) —$CONR^7R^{16}$;

$R^7$ is:
(a) H,
(b) $(C_1-C_6)$-alkyl, (c) phenyl, (d) benzyl, or (e) $(C_3-C_7)$-cycloalkyl;

$R^8$ is:
(a) H,
(b) $(C_1-C_6)$-alkyl, unsubstituted or substituted with one or two substituents selected from the group consisting of:
  i) -phenyl,
  ii) —$(C_3-C_7)$-cycloalkyl,
  iii) —$NR^7R^{16}$,
  iv) -morpholin-4-yl,
  v) —OH,
  vi) —$CO_2R^7$, or
  (vii) —$CON(R^7)_2$, or
(c) phenyl;

$R^9$ is:
(a) H,
(b) $(C_1-C_6)$-alkyl, unsubstituted or substituted with a substituent selected from the group consisting of:
  i) -phenyl,
  ii) —$(C_3-C_7)$-cycloalkyl,
  iii) —$NR^7R^{16}$,
  iv) —OH,
  v) —O—$(C_1-C_4)$-alkyl,
  vi) —$CF_3$,
  vii) —$COOR^7$,
  viii) —$S(O)_n$—$(C_1-C_4)$-alkyl, or
  ix) —$CON(R^7)_2$;
(c) $(C_3-C_7)$-cycloalkyl,
(d) F, Cl, Br, I,
(e) —$COOR^7$,
(f) —$CON(R^7)_2$,
(g) -perfluoro-$(C_1-C_4)$-alkyl,
(h) —O—$(CH_2)_m$—$OR^7$, or
(i) —$S(O)_n$—$(C_1-C_4)$-alkyl;

$R^{10}$ and $R^{11}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^{10}$ and $R^{11}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) phenyl,
(k) $(C_1-C_6)$-alkyl-$S(O)_n$—$(CH_2)_n$—,
(l) hydroxy-$(C_1-C_6)$-alkyl,
(m) —$CF_3$,
(n) —$CO_2R^7$, (o) —OH,
(p) —NR$^7$R$^{16}$,
(q) —[(C$_1$–C$_6$)-alkyl]NR$^7$R$^{16}$,
(r) —NO$_2$,
(s) —(CH$_2$)$_n$—SO$_2$—N(R$^7$)$_2$,
(t) —NR$^7$CO—(C$_1$–C$_4$)-alkyl,
(u) —CON(R$^7$)$_2$, or
(v) when R$^{10}$ and R$^{11}$ are on adjacent carbons, they can join together to form a ring, where R$^{10}$ and R$^{11}$ are represented by —O—CH$_2$—O—;

R$^{12}$ is:
(a) H,
(b) (C$_1$–C$_6$)-alkyl, unsubstituted or substituted with one or two substituents selected from the group consisting of:
  i) —OH,
  ii) —O—(C$_1$–C$_4$)-alkyl,
  iii) —O—(C$_1$–C$_4$)-cycloalkyl,
  iv) —S(O)$_n$—(C$_1$–C$_4$)-alkyl,
  iv) —NR$^7$—(C$_1$–C$_4$)-alkyl,
  v) —NR$^7$R$^{16}$,
  vi) —COOR$^7$,
  vii) —CONHR$^7$,
  viii) —OCOR$^{16}$,
  ix) —CONR$^7$R$^{16}$,
  x) —NR$^7$CONR$^7$R$^{16}$,
  xi) —NR$^7$COOR$^{16}$,
  xii) —C(R$^6$)(OH)—C(R$^6$)(R$^7$)(OH), or
  xiii) —SO$_2$NR$^7$R$^{16}$,
(c) (C$_3$–C$_7$)-cycloalkyl,
(d) —C(R$^6$)(OH)—C(R$^6$)(R$^7$)(OH),
(e) -perfluoro-(C$_1$–C$_4$)-alkyl,
(f) —OR$^7$,
(g) —COOR$^{13}$,
(h) —COR$^{16}$,
(i) —CONR$^7$R$^{16}$,
(j) —CONHSO$_2$R$^{16}$;
(k) —NO$_2$,
(l) —NH$_2$,
(m) —NR$^7$R$^{16}$,
(n) —NR$^7$CONR$^7$R$^{16}$,
(o) —NR$^7$COOR$^{16}$,
(p) —NR$^7$COR$^{16}$,
(q) —NR$^7$CONHSO$_2$R$^{16}$,
(r) —NR$^7$SO$_2$R$^{16}$,
(s) —NR$^7$SO$_2$NH$_2$,
(t) —NR$^7$SO$_2$NHR$^{16}$,
(u) —NR$^7$SO$_2$N(R$^{16}$)$_2$,
(v) —NR$^7$SO$_2$NHCOR$^{16}$,
(w) —SO$_2$NR$^7$R$^{16}$,
(x) —S(O)$_2$—NR$^7$COR$^{16}$,
(y) —S(O)$_2$—NR$^7$COOR$^{16}$,
(z) —S(O)$_2$—NR$^7$CONHR$^{16}$,
(aa) —S(O)$_2$—NR$^7$CONH$_2$, or
(ab) —S(O)$_n$—(C$_1$–C$_4$)-alkyl;

Z is:
(a) —CO$_2$R$^{13}$,
(b) —CONH-(tetrazol-5-yl),
(c) —CONHSO$_2$-phenyl, wherein phenyl is unsubstituted or substituted with one or two substituents selected from the group consisting of:
  i) (C$_1$–C$_4$)-alkyl,
  ii) —O—(C$_1$–C$_4$)-alkyl,
  iii) —CONR$^7$R$^{16}$,
  iv) F, Cl, Br or I,
  v) —COOR$^7$,
  vi) (C$_1$–C$_4$)-perfluoroalkyl,
  vii) (C$_3$–C$_7$)-cycloalkyl,
  viii) NR$^7$R$^{16}$,
  ix) SO$_2$NR$^7$R$^{16}$,
  x) hydroxy, or
  xi) 2,3-, or 3,4-methylenedioxy;
(d) —CONHSO$_2$—(C$_1$–C$_8$)-alkyl, wherein the alkyl group is unsubstituted or substituted as defined in R$^4$(b),
(e) —CONHSO$_2$—(C$_1$–C$_4$)-perfluoroalkyl,
(f) —CONHSO$_2$—(C$_3$–C$_7$)-cycloalkyl,
(g) —CONHSO$_2$—heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl, quinolinyl, or carbazolyl, unsubstituted or substituted with (C$_1$–C$_6$)-alkyl,
(h) -tetrazol-5-yl,
(i) —CONHSO$_2$NH-phenyl, wherein phenyl is unsubstituted or substituted with one or two substituents selected from the group consisting of:
  i) (C$_1$–C$_4$)-alkyl,
  ii) —O—(C$_1$–C$_4$)-alkyl,
  iii) —CONR$^7$R$^{16}$,
  iv) F, Cl, Br or I,
  v) —COOR$^7$,
  vi) (C$_1$–C$_4$)-perfluoroalkyl,
  vii) (C$_3$–C$_7$)-cycloalkyl,
  viii) NR$^7$R$^{16}$,
  ix) SO$_2$NR$^7$R$^{16}$,
  x) hydroxy, or
  xi) 2,3-, or 3,4-methylenedioxy;
(j) —CONHSO$_2$NH—(C$_1$–C$_8$)-alkyl, wherein the alkyl group is unsubstituted or substituted as defined in R$^4$(b),
(k) —CONHSO$_2$NH—(C$_1$–C$_4$)-perfluoroalkyl,
(l) —CONHSO$_2$NH—(C$_3$–C$_7$)-cycloalkyl,
(m) —CONHSO$_2$NH-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl, quinolinyl, or carbazolyl, unsubstituted or substituted with (C$_1$–C$_6$)-alkyl;
(n) —SO$_2$NHCO-phenyl, wherein phenyl is as defined in Z(c) above,
(o) —SO$_2$NHCO—(C$_1$–C$_8$)-alkyl, wherein the alkyl group is unsubstituted or substituted as defined in R$^4$(b),
(p) —SO$_2$NHCO—(C$_1$–C$_4$)-perfluoroalkyl,
(q) —SO$_2$NHCO-heteroaryl, wherein heteroaryl is as defined in Z(g) above,
(r) —SO$_2$NHCON(R$^{16}$)$_2$ wherein the R$^{16}$ groups are the same or different,
(r) —SO$_2$NHCOOR$^{16}$,
(o) —PO(OR$^7$)$_2$, wherein the R$^7$ groups are the same or different, or
(p) —PO(R$^{16}$)OR$^7$;

R$^{13}$ is:
(a) H,
(b) (C$_1$–C$_6$)-alkyl,
(c) CHR$^{14}$—O—COR$^{15}$,
(d) CH$_2$CH$_2$—N[(C$_1$–C$_2$)-alkyl]$_2$,
(e) CH$_2$CH$_2$—N[CH$_2$CH$_2$]$_2$O,
(f) (CH$_2$CH$_2$O)$_y$—O—[(C$_1$–C$_4$)-alkyl], wherein y is 1 or 2,
(g) phenyl, naphthyl, CH$_2$-phenyl or CH$_2$-naphthyl, where phenyl or naphthyl is substituted or unsubstituted with CO$_2$—(C$_1$–C$_6$)-alkyl,

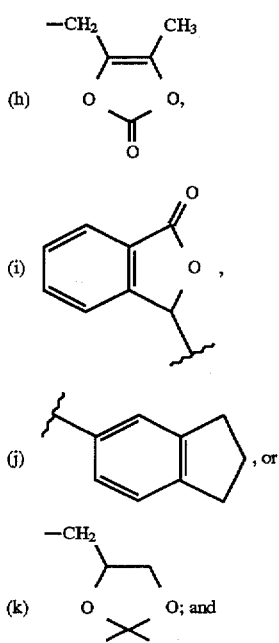

(h) —CH₂—C(CH₃)=C(O)—O—C(=O)—O—

(i) (phthalide-like structure)

(j) (indanyl structure), or (k) —CH₂—CH(O—C(=O)—O—C(CH₃)₂)

$R^{14}$ and $R^{15}$ independently are $(C_1-C_6)$-alkyl or phenyl; and $R^{16}$ is
(a) —$(C_1-C_6)$-alkyl,
(b) —$(C_1-C_4)$-perfluoroalkyl,
(c) —$(C_1-C_4)$-polyfluoroalkyl,
(d) -phenyl, unsubstituted or substituted with a substituent selected from the group consisting of:
  i) $(C_1-C_4)$-alkyl,
  ii) —O—$(C_1-C_4)$-alkyl,
  iii) —CONR$^7$R$^{16}$,
  iv) F, Cl, Br or I,
  v) —COOR$^7$,
(e) —$(C_1-C_4)$-alkyl-phenyl, wherein the phenyl is unsubstituted or substituted with a substituent selected from the group consisting of:
  i) $(C_1-C_4)$-alkyl,
  ii) —O—$(C_1-C_4)$-alkyl,
  iii) —CONR$^7$R$^{16}$,
  iv) F, Cl, Br or I,
  v) —COOR$^7$, or
(f) —$(C_3-C_7)$-cycloalkyl.

A subclass of this embodiment is the compound of structural Formula III:

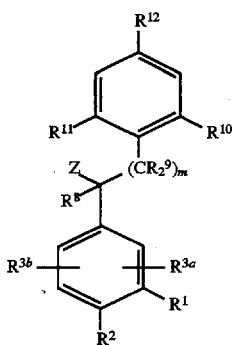

III or a pharmaceutically acceptable salt thereof, wherein:
$R^1$, $R^2$, $R^{3a}$ and $R^{3b}$ are independently:

(a) H,
(b) F, Cl, Br, or I,
(c) —NO₂,
(d) $(C_1-C_4)$-alkyl,
(e) —OR$^7$,
(f) —NHCO—$(C_1-C_4)$-alkyl,
(g) —NHCO—O$(C_1-C_4)$-alkyl,
(h) —O—(CH₂)$_x$—OR$^7$,
(i) —CONR$^7$R$^{16}$, or
(j) —COOR$^7$;

x is 2, 3, or 4;
m is: 0, 1
n is 0, 1 or 2;

$R^1$ and $R^2$ on adjacent carbon atoms can be joined together to form a ring structure:

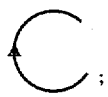

A represents:
a) —Y—C(R$^4$)=C(R$^5$)—,
b) —Y—C(R$^4$)=N—,
c) —Y—N=C(R$^4$)—,
d) —Y—[C(R$^6$)(R$^6$)]$_s$—Y—,
e) —Y—C(R$^6$)(R$^6$)—C(R$^6$)(R$^6$)—,
f) —C(R$^4$)=C(R$^5$)—Y—,
g) —N=C(R$^4$)—Y—,
h) —C(R$^6$)(R$^6$)—C(R$^6$)(R$^6$)—Y—, or
i) —C(R$^4$)=C(R$^5$)—C(R$^4$)=C(R$^5$)—;

s is 1 or 2,
Y is —O—, —S— and NR$^7$
$R^4$ and $R^5$ are independently:
(a) H,
(b) $(C_1-C_6)$-alkyl,
(c) $(C_3-C_7)$-cycloalkyl,
(d) F, Cl, Br, I,
(e) —NR$^7$COOR$^{16}$,
(f) —SO₂NR$^7$R$^{16}$,
(g) —O—$(C_1-C_4)$-alkyl,
(h) —S(O)$_n$—$(C_1-C_4)$-alkyl, or
(i) —NHSO₂R$^{16}$;

$R^6$ is:
(a) H,
(b) F, or
(c) $(C_1-C_4)$-alkyl;

$R^7$ is:
(a) H,
(b) $(C_1-C_6)$-alkyl,
(c) phenyl, or
(d) benzyl;

$R^8$ is:
(a) H,
(b) $(C_1-C_6)$-alkyl, or
(c) phenyl;

$R^9$ is:
(a) H,
(b) $(C_1-C_6)$-alkyl, unsubstituted or substituted with a substituent selected from the group consisting of:
  i) -phenyl,
  ii) —$(C_3-C_7)$-cycloalkyl,
  iii) —OH, or
  iv) —O—$(C_1-C_4)$-alkyl;
(c) F, Cl, Br, I, (d) —COOR$^7$,
(e) —O—(CH$_2$)$_x$—OR$^7$, or
(f) —S(O)$_n$—(C$_1$–C$_4$)-alkyl;

R$^{10}$ and R$^{11}$ are independently:
(a) H,
(b) (C$_1$–C$_6$)-alkyl, unsubstituted or substituted with (C$_3$–C$_7$)-cycloalkyl,
(c) Cl, Br, F, I,
(d) (C$_1$–C$_6$)-alkoxy,
(e) hydroxy-(C$_1$–C$_6$)-alkyl, or
(f) —CO$_2$R$^7$, R$^{12}$ is
(a) H,
(b) (C$_1$–C$_6$)-alkyl, wherein alkyl is defined as unsubstituted or substituted with one or two substituents selected from the group consisting of:
 i) —OH,
 ii) —O—(C$_1$–C$_4$)-alkyl,
 iii) —S(O)$_n$—(C$_1$–C$_4$)-alkyl,
 iv) —NR$^7$R$^{16}$,
 v) —COOR$^7$,
 vi) —CONHR$^7$, or
 vii) —OCOR$^{16}$,
(c) —COOR$^{13}$,
(d) —CONR$^7$R$^{16}$,
(e) —C(R$^6$)(OH)—C(R$^6$)(R$^7$)(OH),
(f) —CONHSO$_2$R$^{16}$,
(g) NO$_2$,
(h) NH$_2$,
(i) OR$^7$, or
(j) perfluoro-(C$_1$–C$_4$)-alkyl;

Z is:
(a) —CO$_2$R$^{13}$,
(b) —CONH-(tetrazol-5-yl),
(c) —CONHSO$_2$-phenyl, wherein phenyl is unsubstituted or substituted with one or two substituents selected from the group consisting of:
 i) (C$_1$–C$_4$)-alkyl,
 ii) —O—(C$_1$–C$_4$)-alkyl,
 iii) —CONR$^7$R$^{16}$,
 iv) F, Cl, Br or I,
 v) —COOR$^7$,
 vi) (C$_1$–C$_4$)-perfluoroalkyl,
 vii) (C$_3$–C$_7$)-cycloalkyl,
 viii) NR$^7$R$^{16}$,
 ix) SO$_2$NR$^7$R$^{16}$,
 x) hydroxy,
 xi) 2,3-, or 3,4-methylenedioxy;
(d) —CONHSO$_2$—(C$_1$–C$_8$)-alkyl, wherein alkyl is unsubstituted or substituted as defined in R$^4$(b),
(e) —CONHSO$_2$—(C$_1$–C$_4$)-perfluoroalkyl,
(f) —CONHSO$_2$—(C$_3$–C$_7$)-cycloalkyl,
(g) —CONHSO$_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl, or
(h) —CONHSO$_2$NH-phenyl, wherein phenyl is unsubstituted or substituted with one or two substituents selected from the group consisting of:
 i) (C$_1$–C$_4$)-alkyl,
 ii) —O—(C$_1$–C$_4$)-alkyl,
 iii) —CONR$^7$R$^{16}$,
 iv) F, Cl, Br or I,
 v) —COOR$^7$,
 vi) (C$_1$–C$_4$)-perfluoroalkyl,
 vii) (C$_3$–C$_7$)-cycloalkyl,
 viii) NR$^7$R$^{16}$,
 ix) SO$_2$NR$^7$R$^{16}$,
 x) hydroxy, or
 xi) 2,3-, or 3,4-methylenedioxy;
(i) —SO$_2$NHCO-phenyl, wherein phenyl is as defined in Z(c) above,
(j) -tetrazol-5-yl; and R$^{16}$ is
(a) (C$_1$–C$_6$)-alkyl,
(b) phenyl,
(c) —(C$_1$–C$_4$)-alkyl-phenyl, or
(d) (C$_3$–C$_7$)-cycloalkyl.

Table II further exemplifies the scope of the invention described by Formula III$_a$:

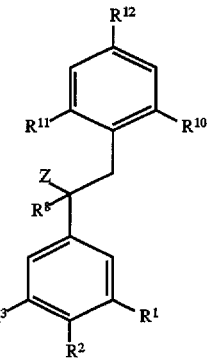

III$_a$ wherein the substituents are as defined in the table below:

| R$^1$ | R$^2$ | R$^3$ | R$^8$ | R$^{10}$ | R$^{12}$ | Z |
|---|---|---|---|---|---|---|
| 3-OCH$_3$ | 4-OCH$_3$ | H | H | n-Pr | CO$_2$H | 4-i-Pr-PhenylSO$_2$NHCO— |
| 3-OCH$_3$ | 4-OCH$_3$ | H | H | i-Bu | CO$_2$H | 4-i-Pr-PhenylSO$_2$NHCO— |
| 3-OCH$_3$ | 4-OCH$_3$ | 5-Cl | H | n-Pr | CO$_2$H | 4-i-Pr-PhenylSO$_2$NHCO— |
| 3-OCH$_3$ | 4-OCH$_3$ | 5-Cl | H | i-Bu | CO$_2$H | 4-i-Pr-PhenylSO$_2$NHCO— |
| 3-OCH$_3$ | 4-OCH$_3$ | H | CH$_3$ | n-Pr | CO$_2$H | 4-i-Pr-PhenylSO$_2$NHCO— |
| 3-OCH$_3$ | 4-OCH$_3$ | H | CH$_3$ | i-Bu | CO$_2$H | 4-i-Pr-PhenylSO$_2$NHCO— |
| 3-OCH$_3$ | 4-OCH$_3$ | 5-Cl | CH$_3$ | n-Pr | CO$_2$H | 4-i-Pr-PhenylSO$_2$NHCO— |
| 3-OCH$_3$ | 4-OCH$_3$ | 5-Cl | CH$_3$ | i-Bu | CO$_2$H | 4-i-Pr-PhenylSO$_2$NHCO— |
| 3-Cl | 4-Cl | H | H | n-Pr | CO$_2$H | 4-i-Pr-PhenylSO$_2$NHCO— |
| 3-Cl | 4-Cl | H | H | i-Bu | CO$_2$H | 4-i-Pr-PhenylSO$_2$NHCO— |
| 3-Cl | 4-Cl | H | CH$_3$ | n-Pr | CO$_2$H | 4-i-Pr-PhenylSO$_2$NHCO— |
| 3-Cl | 4-Cl | H | CH$_3$ | i-Bu | CO$_2$H | 4-i-Pr-PhenylSO$_2$NHCO— | and Formula III$_b$:

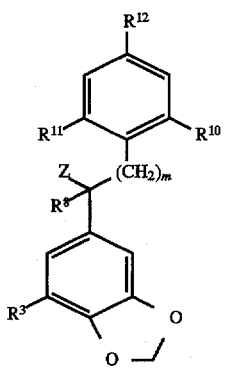

wherein the substituents are as defined in the table below:

| $R^3$ | $R^8$ | m | $R^{10}$ | $R^{11}$ | $R^{12}$ | Z |
|---|---|---|---|---|---|---|
| H | H | 1 | H | H | H | $CO_2H$ |
| H | H | 1 | H | H | H | 4-i-Pr-PhenylSO$_2$NHCO— |
| H | H | 2 | H | H | H | $CO_2H$ |
| H | H | 2 | H | H | H | 4-i-Pr-PhenylSO$_2$NHCO— |
| H | H | 1 | n-Pr | H | H | $CO_2H$ |
| H | H | 1 | n-Pr | H | H | 4-i-Pr-PhenylSO$_2$NHCO— |
| H | H | 1 | n-Pr | n-Pr | H | $CO_2H$ |
| H | H | 1 | n-Pr | n-Pr | H | 4-i-Pr-PhenylSO$_2$NHCO— |
| H | H | 1 | H | H | $CO_2H$ | $CO_2H$ |
| H | H | 1 | H | H | $CO_2H$ | 4-i-Pr-PhenylSO$_2$NHCO— |
| H | H | 1 | n-Pr | H | $CO_2H$ | $CO_2H$ |
| H | H | 1 | n-Pr | H | $CO_2H$ | 4-i-Pr-PhenylSO$_2$NHCO— |
| H | H | 1 | n-Pr | n-Pr | $CO_2H$ | $CO_2H$ |
| H | H | 1 | n-Pr | n-Pr | $CO_2H$ | 4-i-Pr-PhenylSO$_2$NHCO— |
| H | $CH_3$ | 1 | H | H | H | $CO_2H$ |
| H | $CH_3$ | 1 | H | H | H | 4-i-Pr-PhenylSO$_2$NHCO— |
| H | $CH_3$ | 1 | n-Pr | H | H | $CO_2H$ |
| H | $CH_3$ | 1 | n-Pr | H | H | 4-i-Pr-PhenylSO$_2$NHCO— |
| H | $CH_3$ | 1 | n-Pr | n-Pr | H | $CO_2H$ |
| H | $CH_3$ | 1 | n-Pr | n-Pr | H | 4-i-Pr-PhenylSO$_2$NHCO— |
| H | $CH_3$ | 1 | H | H | $CO_2H$ | $CO_2H$ |
| H | $CH_3$ | 1 | H | H | $CO_2H$ | 4-i-Pr-PhenylSO$_2$NHCO— |
| H | $CH_3$ | 1 | n-Pr | H | $CO_2H$ | $CO_2H$ |
| H | $CH_3$ | 1 | n-Pr | H | $CO_2H$ | 4-i-Pr-PhenylSO$_2$NHCO— |
| H | $CH_3$ | 1 | n-Pr | n-Pr | $CO_2H$ | $CO_2H$ |
| H | $CH_3$ | 1 | n-Pr | n-Pr | $CO_2H$ | 4-i-Pr-PhenylSO$_2$NHCO— |
| H | H | 1 | n-Pr | H | $CO_2H$ | PhenylSO$_2$NHCO— |
| H | H | 1 | n-Pr | H | $CO_2H$ | 4-t-Bu-PhenylSO$_2$NHCO— |
| H | H | 1 | n-Pr | H | $CO_2H$ | 4-Br-PhenylSO$_2$NHCO— |
| H | H | 1 | n-Pr | H | $CO_2H$ | 4-CF$_3$-PhenylSO$_2$NHCO— |
| H | H | 1 | n-Pr | H | $CO_2H$ | 2-($CO_2H$)-PhSO$_2$NHCO— |
| H | H | 1 | n-Pr | H | $CO_2H$ | Tetrazol-5-yl |
| H | H | 1 | n-Pr | H | $CO_2H$ | Tetrazol-5-ylNHCO— |
| H | H | 1 | n-Pr | H | $CO_2H$ | i-PrSO$_2$NHCO— |
| H | H | 1 | n-Pr | H | $CO_2H$ | CH$_3$SO$_2$NHCO— |
| H | H | 1 | H | H | CF$_3$ | 4-i-Pr-PhenylSO$_2$NHCO— |
| H | H | 1 | H | H | CH$_2$OH | 4-i-Pr-PhenylSO$_2$NHCO— |

-continued

| | $R^3$ | $R^8$ | m | $R^{10}$ | $R^{11}$ | $R^{12}$ | Z |
|---|---|---|---|---|---|---|---|
| III$_b$ | H | H | 1 | H | H | OCH$_3$ | 4-i-Pr-PhenylSO$_2$NHCO— |
| | H | H | 1 | H | H | Cl | 4-i-Pr-PhenylSO$_2$NHCO— |
| | H | H | 1 | H | H | CO$_2$CH$_3$ | 4-i-Pr-PhenylSO$_2$NHCO— |
| | H | H | 1 | n-Pr | H | CF$_3$ | 4-i-Pr-PhenylSO$_2$NHCO— |
| | H | H | 1 | n-Pr | H | CH$_2$OH | 4-i-Pr-PhenylSO$_2$NHCO— |
| | H | H | 1 | n-Pr | H | OCH$_3$ | 4-i-Pr-PhenylSO$_2$NHCO— |
| | H | H | 1 | n-Pr | H | Cl | 4-i-Pr-PhenylSO$_2$NHCO— |
| | H | H | 1 | n-Pr | H | CO$_2$CH$_3$ | 4-i-Pr-PhenylSO$_2$NHCO— |
| | H | CH$_3$ | 1 | n-Pr | H | CF$_3$ | 4-i-Pr-PhenylSO$_2$NHCO— |
| | H | CH$_3$ | 1 | n-Pr | H | CH$_2$OH | 4-i-Pr-PhenylSO$_2$NHCO— |
| | H | CH$_3$ | 1 | n-Pr | H | OCH$_3$ | 4-i-Pr-PhenylSO$_2$NHCO— |
| | H | CH$_3$ | 1 | n-Pr | H | Cl | 4-i-Pr-PhenylSO$_2$NHCO— |
| | H | CH$_3$ | 1 | n-Pr | H | CO$_2$CH$_3$ | 4-i-Pr-PhenylSO$_2$NHCO— |
| | 5-OCH$_3$ | H | 1 | n-Pr | H | CO$_2$H | 4-i-Pr-PhenylSO$_2$NHCO— |
| | 5-OCH$_3$ | H | 1 | i-Bu | H | CO$_2$H | 4-i-Pr-PhenylSO$_2$NHCO— |
| | 5-Cl | H | 1 | n-Pr | H | CO$_2$H | 4-i-Pr-PhenylSO$_2$NHCO— |
| | 5-Cl | H | 1 | i-Bu | H | CO$_2$H | 4-i-Pr-PhenylSO$_2$NHCO— |
| | 5-Br | H | 1 | n-Pr | H | CO$_2$H | 4-i-Pr-PhenylSO$_2$NHCO— |
| | 5-Br | H | 1 | i-Bu | H | CO$_2$H | 4-i-Pr-PhenylSO$_2$NHCO— |
| | 5-F | H | 1 | n-Pr | H | CO$_2$H | 4-i-Pr-PhenylSO$_2$NHCO— |
| | 5-F | H | 1 | i-Bu | H | CO$_2$H | 4-i-Pr-PhenylSO$_2$NHCO— |
| | 5-OCH$_3$ | CH$_3$ | 1 | i-Pr | H | CO$_2$H | 4-i-Pr-PhenylSO$_2$NHCO— |
| | 5-OCH$_3$ | CH$_3$ | 1 | i-Bu | H | CO$_2$H | 4-i-Pr-PhenylSO$_2$NHCO— |
| | 5-Cl | CH$_3$ | 1 | n-Pr | H | CO$_2$H | 4-i-Pr-PhenylSO$_2$NHCO— |
| | 5-Cl | CH$_3$ | 1 | i-Bu | H | CO$_2$H | 4-i-Pr-PhenylSO$_2$NHCO— |
| | H | H | 1 | n-Pr | H | CO$_2$H | 4-i-Pr-PhenylCONHSO$_2$— |
| | H | H | 1 | n-Pr | H | CO$_2$H | 4-t-Pr-PhenylCONHSO$_2$— |
| | H | H | 1 | n-Pr | H | CO$_2$H | PhenylCONHSO$_2$— |

Another subclass of compounds of Formula IV is:

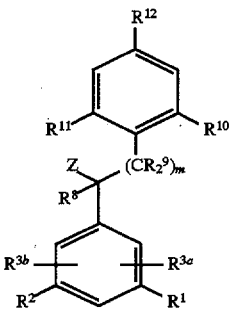

or a pharmaceutically acceptable salt thereof, wherein:
$R^1$, $R^2$, $R^{3a}$ and $R^{3b}$ are independently:
  (a) H,
  (b) F, Cl, Br, or I, (c) —NO$_2$,
(d) (C$_1$–C$_4$)-alkyl,
(e) —OR$^7$,
(f) —NHCO—(C$_1$–C$_4$)-alkyl,
(g) —NHCO—O(C$_1$–C$_4$)-alkyl,
(h) —O—(CH$_2$)$_x$—OR$^7$,
(i) —CONR$^7$R$^{16}$, or
(j) —COOR$^7$;

m is: 1 or 2;

x is 2, 3 or 4;

n is 0, 1 or 2;

R$^4$ and R$^5$ are independently:
(a) H,
(b) (C$_1$–C$_6$)-alkyl,
(c) (C$_3$–C$_7$)-cycloalkyl,
(d) F, Cl, Br, I,
(e) —NR$^7$COOR$^{16}$,
(f) —SO$_2$NR$^7$R$^{16}$,
(g) —O—(C$_1$–C$_4$)-alkyl,
(h) —S(O)$_n$—(C$_1$–C$_4$)-alkyl, or
—NHSO$_2$R$^{16}$;

R$^6$ is:
(a) H,
(b) F, or
(c) (C$_1$–C$_4$)-alkyl;

R$^7$ is:
(a) H,
(b) (C$_1$–C$_6$)-alkyl,
(c) phenyl, or
(d) benzyl;

R$^8$ is:
(a) H,
(b) (C$_1$–C$_6$)-alkyl, or
(c) phenyl;

R$^9$ is:
(a) H,
(b) (C$_1$–C$_6$)-alkyl, unsubstituted or substituted with a substituent selected from the group consisting of:
  i) -phenyl,
  ii) —(C$_3$–C$_7$)-cycloalkyl,
  iii) —OH, or
  iv) —O—(C$_1$–C$_4$)-alkyl;
(c) F, Cl, Br, I,
(d) —COOR$^7$,
(e) —O—(CH$_2$)$_x$—OR$^7$, or
(f) —S(O)$_n$—(C$_1$–C$_4$)-alkyl;

R$^{10}$ and R$^{11}$ are independently:
(a) H,
(b) (C$_1$–C$_6$)-alkyl, unsubstituted or substituted with (C$_3$–C$_7$)-cycloalkyl,
(c) Cl, Br, F, I,
(d) (C$_1$–C$_6$)-alkoxy, or
(e) hydroxy-(C$_1$–C$_6$)-alkyl;
(f) —CO$_2$R$^7$, R$^{12}$ is
(a) H,
(b) (C$_1$–C$_6$)-alkyl, wherein alkyl is defined as unsubstituted or substituted with one or two substituents selected from the group consisting of:
  i) —OH,
  ii) —O—(C$_1$–C$_4$)-alkyl,
  iii) —S(O)$_n$—(C$_1$–C$_4$)-alkyl,
  iv) —NR$^7$R$^{16}$,
  v) —COOR$^7$,
  vi) —CONHR$^7$, or
  vii) —OCOR$^{16}$,
(c) —COOR$^{13}$,
(d) —CONR$^7$R$^{16}$,
(e) —C(R$^6$)(OH)—C(R$^6$)(R$^7$)(OH),
(f) —CONHSO$_2$R$^{16}$,
(g) NO$_2$,
(h) NH$_2$,
(i) OR$^7$, or
(j) perfluoro-(C$_1$–C$_4$)-alkyl;

Z is:
(a) CO$_2$R$^{13}$,
(b) —CONH-(tetrazol-5-yl),
(c) —CONHSO$_2$-phenyl, wherein phenyl is unsubstituted or substituted with one or two substituents selected from the group consisting of:
  i) (C$_1$–C$_4$)-alkyl,
  ii) —O—(C$_1$–C$_4$)-alkyl,
  iii) —CONR$^7$R$^{16}$,
  iv) F, Cl, Br or I,
  v) —COOR$^7$,
  vi) (C$_1$–C$_4$)-perfluoroalkyl,
  vii) (C$_3$–C$_7$)-cycloalkyl,
  viii) NR$^7$R$^{16}$,
  ix) SO$_2$NR$^7$R$^{16}$,
  x) hydroxy,
  xi) 2,3-, or 3,4-methylenedioxy;
(d) —CONHSO$_2$—(C$_1$–C$_8$)-alkyl, wherein alkyl is unsubstituted or substituted as defined in R$^4$(b),
(e) —CONHSO$_2$—(C$_1$–C$_4$)-perfluoroalkyl,
(f) —CONHSO$_2$—(C$_3$–C$_7$)-cycloalkyl,
(g) —CONHSO$_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl, or
(h) -tetrazol-5-yl; and R$^{16}$ is
(a) (C$_1$–C$_6$)-alkyl,
(b) phenyl,
(c) —(C$_1$–C$_4$)-alkyl-phenyl, or
(d) (C$_3$–C$_7$)-cycloalkyl.

Table I further exemplifies the scope of the invention described by Formula IV:

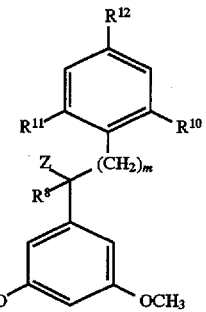

IV wherein the substituents are as defined in the table below:

| R$^8$ | m | R$^{10}$ | R$^{11}$ | R$^{12}$ | Z |
|---|---|---|---|---|---|
| H | 1 | H | H | H | CO$_2$H |
| H | 1 | H | H | H | 4-i-Pr-PhenylSO$_2$NHCO— |
| H | 2 | H | H | H | CO$_2$H |
| H | 2 | H | H | H | 4-i-Pr-PhenylSO$_2$NHCO— |
| H | 1 | n-Pr | H | H | CO$_2$H |

-continued

| R⁸ | m | R¹⁰ | R¹¹ | R¹² | Z |
|---|---|---|---|---|---|
| H | 1 | n-Pr | H | H | 4-i-Pr-PhenylSO₂NHCO— |
| H | 1 | n-Pr | n-Pr | H | CO₂H |
| H | 1 | n-Pr | n-Pr | H | 4-i-Pr-PhenylSO₂NHCO— |
| H | 1 | H | H | CO₂H | CO₂H |
| H | 1 | H | H | CO₂H | 4-i-Pr-PhenylSO₂NHCO— |
| H | 1 | n-Pr | H | CO₂H | CO₂H |
| H | 1 | n-Pr | H | CO₂H | 4-i-Pr-PhenylSO₂NHCO— |
| H | 1 | n-Pr | n-Pr | CO₂H | CO₂H |
| H | 1 | n-Pr | n-Pr | CO₂H | 4-i-Pr-PhenylSO₂NHCO— |
| CH₃ | 1 | H | H | H | CO₂H |
| CH₃ | 1 | H | H | H | 4-i-Pr-PhenylSO₂NHCO— |
| CH₃ | 1 | n-Pr | H | H | CO₂H |
| CH₃ | 1 | n-Pr | H | H | 4-i-Pr-PhenylSO₂NHCO— |
| CH₃ | 1 | n-Pr | n-Pr | H | CO₂H |
| CH₃ | 1 | n-Pr | n-Pr | H | 4-i-Pr-PhenylSO₂NHCO— |
| CH₃ | 1 | H | H | CO₂H | CO₂H |
| CH₃ | 1 | H | H | CO₂H | 4-i-Pr-PhenylSO₂NHCO— |
| CH₃ | 1 | n-Pr | H | CO₂H | CO₂H |
| CH₃ | 1 | n-Pr | H | CO₂H | 4-i-Pr-PhenylSO₂NHCO— |
| CH₃ | 1 | n-Pr | n-Pr | CO₂H | CO₂H |
| CH₃ | 1 | n-Pr | n-Pr | CO₂H | 4-i-Pr-PhenylSO₂NHCO— |
| H | 1 | n-Pr | H | CO₂H | PhenylSO₂NHCO— |
| H | 1 | n-Pr | H | CO₂H | 4-t-Bu-PhenylSO₂NHCO— |
| H | 1 | n-Pr | H | CO₂H | 4-Br-PhenylSO₂NHCO— |
| H | 1 | n-Pr | H | CO₂H | 4-CF₃-PhenylSO₂NHCO— |
| H | 1 | n-Pr | H | CO₂H | 2-(CO₂H)-PhenylSO₂NHCO— |
| H | 1 | n-Pr | H | CO₂H | Tetrazol-5-yl |
| H | 1 | n-Pr | H | CO₂H | Tetrazol-5-ylNHCO— |
| H | 1 | n-Pr | H | CO₂H | i-PrSO₂NHCO— |
| H | 1 | n-Pr | H | CO₂H | CH₃SO₂NHCO— |
| H | 1 | H | H | CF₃ | 4-i-Pr-PhenylSO₂NHCO— |
| H | 1 | H | H | CH₂OH | 4-i-Pr-PhenylSO₂NHCO— |
| H | 1 | H | H | OCH₃ | 4-i-Pr-PhenylSO₂NHCO— |
| H | 1 | H | H | Cl | 4-i-Pr-PhenylSO₂NHCO— |
| H | 1 | H | H | CO₂CH₃ | 4-i-Pr-PhenylSO₂NHCO— |
| H | 1 | n-Pr | H | CF₃ | 4-i-Pr-PhenylSO₂NHCO— |
| H | 1 | n-Pr | H | CH₂OH | 4-i-Pr-PhenylSO₂NHCO— |
| H | 1 | n-Pr | H | OCH₃ | 4-i-Pr-PhenylSO₂NHCO— |
| H | 1 | n-Pr | H | Cl | 4-i-Pr-PhenylSO₂NHCO— |
| H | 1 | n-Pr | H | CO₂CH₃ | 4-i-Pr-PhenylSO₂NHCO— |
| CH₃ | 1 | n-Pr | H | CF₃ | 4-i-Pr-PhenylSO₂NHCO— |
| CH₃ | 1 | n-Pr | H | CH₂OH | 4-i-Pr-PhenylSO₂NHCO— |
| CH₃ | 1 | n-Pr | H | OCH₃ | 4-i-Pr-PhenylSO₂NHCO— |
| CH₃ | 1 | n-Pr | H | Cl | 4-i-Pr-PhenylSO₂NHCO— |
| CH₃ | 1 | n-Pr | H | CO₂CH₃ | 4-i-Pr-PhenylSO₂NHCO—. |

A third subclass of this embodiment are the compounds of structural Formula V

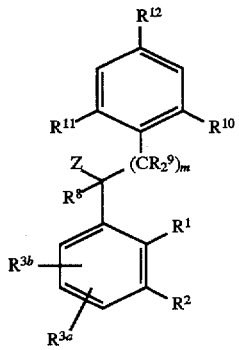

V or a pharmaceutically acceptable salt thereof, wherein:
$R^1$ and $R^2$ are represented by the following ring structure:

A represents:
a) —Y—C($R^4$)=C($R^5$)—,
b) —Y—C($R^4$)=N—,
c) —Y—N=C($R^4$)—,
d) —O—[C($R^6$)($R^6$)]$_s$—O—,
e) —Y—C($R^6$)($R^6$)—C($R^6$)($R^6$)—,
f) —C($R^4$)=C($R^5$)—Y—,
g) —N=C($R^4$)—Y—,
h) —C($R^6$)($R^6$)—C($R^6$)($R^6$)—Y—, or
i) —C($R^4$)=C($R^5$)—C($R^4$)=C($R^5$)—;

s is 1 or 2,

Y is —O—, —S— and $NR^7$;

$R^{3a}$ and $R^{3b}$ are independently:
 (a) H,
 (b) F, Cl, Br, or I,
 (c) —NO₂,
 (d) ($C_1$–$C_4$)-alkyl,
 (e) —$OR^7$,
 (f) —NHCO—($C_1$–$C_4$)-alkyl,
 (g) —NHCO—O($C_1$–$C_4$)-alkyl,
 (h) —O—(CH₂)$_x$—$OR^7$,
 (i) —$CONR^7R^{16}$, or
 (j) —$COOR^7$;

x is 2, 3 or 4, m is: 1 or 2;

n is 0, 1 or 2, $R^4$ and $R^5$ are independently:
 (a) H,
 (b) ($C_1$–$C_6$)-alkyl,
 (c) ($C_3$–$C_7$)-cycloalkyl,
 (d) F, Cl, Br, I,
 (e) —$NR^7COOR^{16}$,
 (f) —$SO_2NR^7R^{16}$,
 (g) —O—($C_1$–$C_4$)-alkyl,
 (h) —S(O)$_n$—($C_1$–$C_4$)-alkyl, or
 (i) —$NHSO_2R^{16}$;

$R^6$ is:
 (a) H,
 (b) F, or
 (c) ($C_1$–$C_4$)-alkyl;

$R^7$ is:
 (a) H,
 (b) ($C_1$–$C_6$)-alkyl,
 (c) phenyl, or
 (d) benzyl;

$R^8$ is:
 (a) H,
 (b) ($C_1$–$C_6$)-alkyl, or
 (c) phenyl;

$R^9$ is:
 (a) H,
 (b) ($C_1$–$C_6$)-alkyl, unsubstituted or substituted with a substituent selected from the group consisting of:
  i) -phenyl,
  ii) —($C_3$–$C_7$)-cycloalkyl,
  iii) —OH, or
  iv) —O—($C_1$–$C_4$)-alkyl;
 (c) F, Cl, Br, I,
 (d) —$COOR^7$,
 (e) —O—(CH₂)$_x$—$OR^7$, or
 (f) —S(O)$_n$—($C_1$–$C_4$)-alkyl;

$R^{10}$ and $R^{11}$ are independently:
 (a) H,
 (b) ($C_1$–$C_6$)-alkyl, unsubstituted or substituted with ($C_3$–$C_7$)-cycloalkyl,
 (c) Cl, Br, F, I,
 (d) ($C_1$–$C_6$)-alkoxy, or (e) hydroxy-$(C_1-C_6)$-alkyl;

(f) —$CO_2R^7$, $R^{12}$ is (a) H, (b) $(C_1-C_6)$-alkyl, wherein alkyl is defined as unsubstituted or substituted with one or two substituents selected from the group consisting of:

i) —OH, ii) —O—$(C_1-C_4)$-alkyl, iii) —$S(O)_n$—$(C_1-C_4)$-alkyl, iv) —$NR^7R^{16}$, v) —$COOR^7$, vi) —$CONHR^7$, or vii) —$OCOR^{16}$, (c) —$COOR^{13}$, (d) —$CONR^7R^{16}$, (e) —$C(R^6)(OH)$—$C(R^6)(R^7)(OH)$, (f) —$CONHSO_2R^{16}$, (g) $NO_2$, (h) $NH_2$, (i) $OR^7$, or (j) perfluoro-$(C_1-C_4)$-alkyl;

Z is:

(a) —$CO_2R^{13}$, (b) —CONH-(tetrazol-5-yl), (c) —$CONHSO_2$-phenyl, wherein phenyl is unsubstituted or substituted with one or two substituents selected from the group consisting of:

i) $(C_1-C_4)$-alkyl, ii) —O—$(C_1-C_4)$-alkyl, iii) —$CONR^7R^{16}$, iv) F, Cl, Br or I, v) —$COOR^7$, vi) $(C_1-C_4)$-perfluoroalkyl, vii) $(C_3-C_7)$-cycloalkyl, viii) $NR^7R^{16}$, ix) $SO_2NR^7R^{16}$, x) hydroxy, xi) 2,3-, or 3,4-methylenedioxy;

(d) —$CONHSO_2$—$(C_1-C_8)$-alkyl, wherein alkyl is unsubstituted or substituted as defined in $R^4$(b), (e) —$CONHSO_2$—$(C_1-C_4)$-perfluoroalkyl, (f) —$CONHSO_2$—$(C_3-C_7)$-cycloalkyl, (g) —$CONHSO_2$-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl, or (h) -tetrazol-5-yl; and $R^{16}$ is (a) $(C_1-C_6)$-alkyl, (b) phenyl, (c) —$(C_1-C_4)$-alkyl-phenyl, or (d) $(C_3-C_7)$-cycloalkyl.

Table III further exemplifies the scope of the invention described by Formula V:

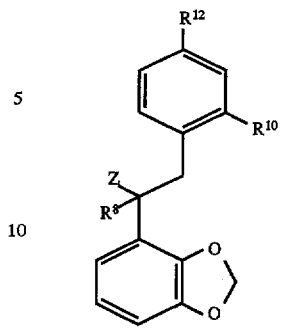

wherein the substituents are as defined in the table below:

| $R^8$ | $R^{10}$ | $R^{12}$ | Z |
|---|---|---|---|
| H | n-Pr | H | $CO_2H$ |
| H | n-Pr | H | 4-i-Pr-PhenylSO$_2$NHCO— |
| H | H | $CO_2H$ | $CO_2H$ |
| H | H | $CO_2H$ | 4-i-Pr-PhenylSO$_2$NHCO— |
| H | n-Pr | $CO_2H$ | $CO_2H$ |
| H | n-Pr | $CO_2H$ | 4-i-Pr-PhenylSO$_2$NHCO— |
| $CH_3$ | H | H | $CO_2H$ |
| $CH_3$ | H | H | 4-i-Pr-PhenylSO$_2$NHCO— |
| $CH_3$ | n-Pr | H | $CO_2H$ |
| $CH_3$ | n-Pr | H | 4-i-Pr-PhenylSO$_2$NHCO— |
| $CH_3$ | H | $CO_2H$ | $CO_2H$ |
| $CH_3$ | H | $CO_2H$ | 4-i-Pr-PhenylSO$_2$NHCO— |
| $CH_3$ | n-Pr | $CO_2H$ | $CO_2H$ |
| $CH_3$ | n-Pr | $CO_2H$ | 4-i-Pr-PhenylSO$_2$NHCO— |
| H | n-Pr | $CO_2H$ | PhenylSO$_2$NHCO— |
| H | n-Pr | $CO_2H$ | 4-t-Bu-PhenylSO$_2$NHCO— |
| H | n-Pr | $CO_2H$ | 4-Br-PhenylSO$_2$NHCO— |
| H | n-Pr | $CO_2H$ | 4-CF$_3$-PhenylSO$_2$NHCO— |
| H | n-Pr | $CO_2H$ | 2-(CO$_2$H)-PhenylSO$_2$NHCO— |
| H | n-Pr | $CO_2H$ | Tetrazol-5-ylNHCO— |
| H | n-Pr | $CO_2H$ | i-PrSO$_2$NHCO— |
| H | n-Pr | $CO_2H$ | CH$_3$SO$_2$NHCO— |
| H | H | $CF_3$ | 4-i-Pr-PhenylSO$_2$NHCO— |
| H | H | $CH_2OH$ | 4-i-Pr-PhenylSO$_2$NHCO— |
| H | H | $OCH_3$ | 4-i-Pr-PhenylSO$_2$NHCO— |
| H | H | Cl | 4-i-Pr-PhenylSO$_2$NHCO— |
| H | H | $CO_2CH_3$ | 4-i-Pr-PhenylSO$_2$NHCO— |
| H | n-Pr | $CF_3$ | 4-i-Pr-PhenylSO$_2$NHCO— |
| H | n-Pr | $CH_2OH$ | 4-i-Pr-PhenylSO$_2$NHCO— |
| H | n-Pr | $OCH_3$ | 4-i-Pr-PhenylSO$_2$NHCO— |
| H | n-Pr | Cl | 4-i-Pr-PhenylSO$_2$NHCO— |
| H | n-Pr | $CO_2CH_3$ | 4-i-Pr-PhenylSO$_2$NHCO— |

The alkyl substituents recited above denote straight and branched chain hydrocarbons of the length specified such as methyl, ethyl, isopropyl, isobutyl, neopentyl, isopentyl, etc.

The alkenyl substituents denote alkyl groups as described above which are modified so that each contains a carbon to carbon double bond such as vinyl, allyl and 2-butenyl.

Cycloalkyl denotes rings composed of 3 to 8 methylene groups, each of which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl or carbazolyl.

Although the reaction schemes described below are reasonably general, it will be understood by those skilled in the art of organic synthesis that one or more functional groups present in a given compound of Formula I may render the molecule incompatible with a particular synthetic sequence.

In such a case an alternative synthetic route, an altered order of steps, or a strategy of functional group protection (see: Greene T. W. *Protective Groups in Organic Synthesis*; John Wiley & Sons; New York, 1981) and deprotection may be employed. In all cases the particular reaction conditions, including reagents, solvent, temperature and time, should be chosen so that they are consistent with the nature of the functionality present in the molecule.

The compounds of Formulas I–V can be synthesized using the reactions and techniques illustrated in the following schemes and described below. Some of the reaction schemes described here have been generalized for simplicity, and it is to be understood that in these generalized schemes, unless specified more narrowly in the text, the alkyl and aryl groups represent unfunctionalized or functionalized derivatives as described before.

One general method for the synthesis of compounds of Formulas I–V is outlined in Scheme 1. A substituted toluene derivative of Formula 1 which bears an electron withdrawing substituent $Z^1$ is deprotonated at the active methylene group with a suitable base and the resulting anion is alkylated with a compound of Formula 2 bearing the leaving group Q and m equals 1 or 2. The leaving group Q present in the alkylating agent 2 can be any suitable leaving group such as chloride, bromide, iodide, methanesulfonate (OMs), p-toluenesulfonate (OTs), or triflate (OTf). In structure 1 the substituent $Z^1$ may be any of the substituents defined previously for Z, or $Z^1$ may represent a functional group that may be converted in a subsequent reaction to one of the substituents defined for Z. Alkylation of the anion derived from compound 1 occurs at the carbon atom bearing the substituent $Z^1$ and compound 3 is the product. In a separate step the group $Z^1$ is then converted to one of the substituents defined previously for Z and a compound of Formula I is produced.

The alkylation reaction shown in Scheme 1 may be conducted under a variety of conditions which are consistent with the choice of substituents on compounds 1 and 2. Selection of the base used for the deprotonation of 1 is based upon consideration of the nature of the electron withdrawing group $Z^1$ and the other substituents present. Typically, the alkylation reaction is accomplished by deprotonation of 1 with a strong base such as an alkali metal hydride, alkoxide or amide in an aprotic solvent such as ether, tetrahydrofuran (THF), dimethylformamide (DMF), dimethylsulfoxide (DMSO) or the like. When sensitive functional groups are present, the deprotonation and alkylation reactions are preferably conducted at low temperatures and under an inert atmosphere using techniques known to those skilled in organic synthesis.

Scheme 1

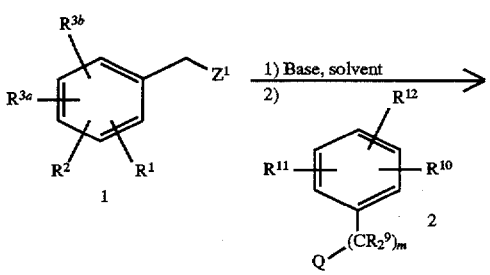

-continued
Scheme 1

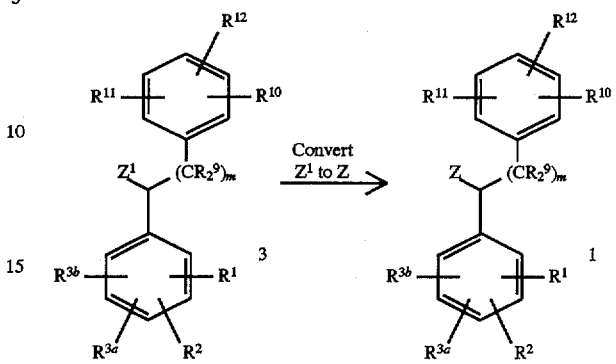

$Z^1$ = a precursor to Z
m = 1 or 2
Q = Cl, Br, I, OMs, OTs, OTf, etc.

Scheme 2 illustrates a more specific example of this process. Structure 4 represents a compound of general Formula I where $Z^1$ is an ester group. In order to simplify the structures of Scheme 2 and in some of the following examples, compound 5 will be used to illustrate an alkylating agent of general Formula 2 where m equals 1 and Q is bromine. It will be recognized however, that in these transformations m may equal 1 or 2 and the leaving group Q may be any suitable leaving group as previously defined. Deprotonation of 4 with a strong base such as lithium bis(trimethylsilylamide) in THF yields the enolate of a phenylacetic ester. When this enolate anion is reacted with an akylating agent of general Formula 2 such as 5, compound 6 is the product and this structure corresponds to a compound of general Formula 3 wherein m=1 and $Z^1$ is an ester. The ester substituent in structure 5 may be subsequently converted to one of the substituents defined previously for Z. For instance, $Z^1$ may be hydrolyzed to form 7, a compound of general Formula I where m=1 and Z is a carboxylic acid.

Scheme 2

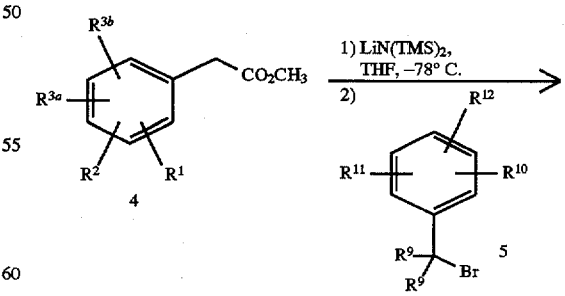

-continued
Scheme 2

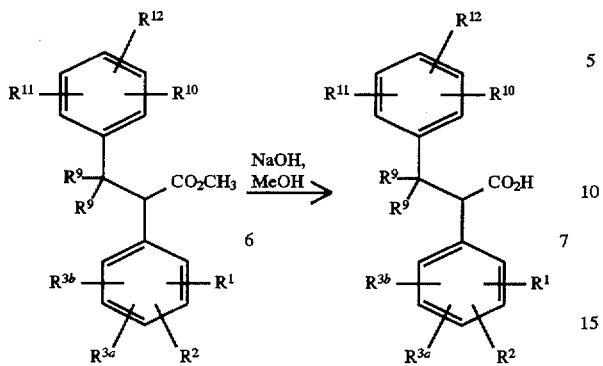

Carboxylic acids of Formula 7 are asymmetric and when prepared as shown in Scheme 2 the compounds are racemic mixtures. When it is desired to prepare optically active enantiomers of carboxylic acids 7 this may be accomplished as shown in Scheme 3. A substituted phenylacetic acid is first converted to an enantiomerically pure acyloxazolidinone using either (S)-(−)-4-benzyl-2-oxazolidinone (shown for 8 and 9 in Scheme 3) or (4R,5S)-(+)-4-methyl-5-phenyl-2-oxazolidinone according to established methodology (see: Evans, D. A. *Aldrichimica Acta* 1982, 15, 23 and references cited therein). The enolate anions derived from such acyloxazolidinones may be alkylated with 5 stereospecifically, and compounds of Formula 9 are obtained. The oxazolidinone group is then removed (Evans, D. A.; Britton, T. C.; Ellman, J. A. *Tetrahedron Lett.* 1987, 6141.) with basic hydrogen peroxide to afford enantiomerically pure compounds of Formula 7. The two oxazolidinones recited above are both readily available, and the choice of which one is used for the preparation of the acyloxazolidinone (i.e. 8) determines the absolute configuration of the product (7).

Scheme 3

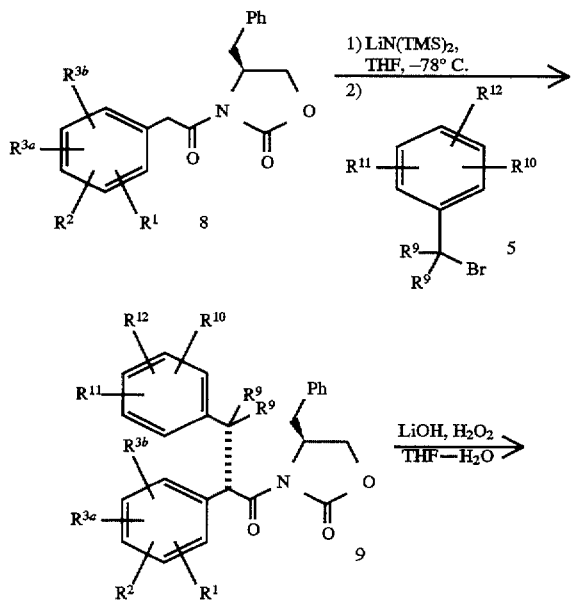

-continued
Scheme 3

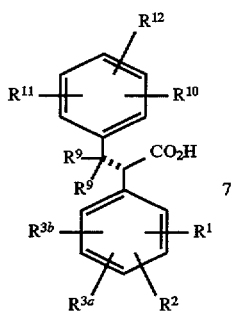

The carboxylic acids of general Formula I (Z=CO$_2$H) are useful intermediates for the preparation of other compounds of general Formula 1 which are within the scope of this invention. Thus, in equation 1 in Scheme 4, compound 9 of general Formula 1 where Z=—CONH-(tetrazol-5-yl) may be prepared by reaction of carboxylic acid 7 with 1,1'-carbonyldiimidazole (CDI) in DMF followed by addition of 5-aminotetrazole. Similarly, as shown in equation 2 of Scheme 4, reaction of carboxylic acids like 7 with 1,1'-carbonyldiimidazole in THF followed by addition of either an alkylsulfonamide, a phenylsulfonamide (illustrated in Scheme 4) or a heteroarylsulfonamide provides compounds (10) of general Formulas I–V where Z is an acylsulfonamide such as Z=—CONHSO$_2$—(C$_1$-C$_8$)-alkyl, Z=—CONHSO$_2$-phenyl, or Z=—CONHSO$_2$-heteroaryl and the alkyl, phenyl or heteroaryl groups may be substituted as previously defined.

Scheme 4

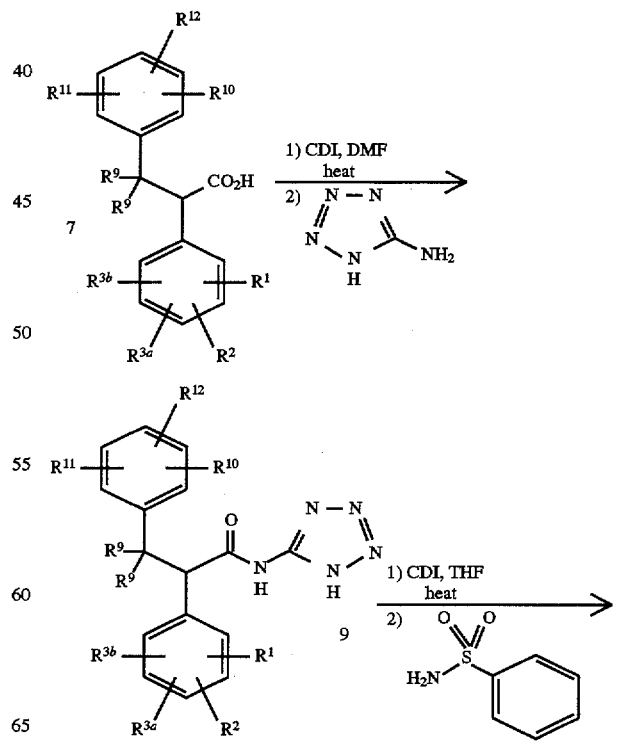

Scheme 4 -continued

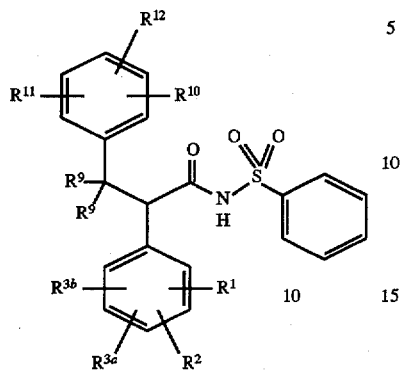

The group $Z^1$ may also be converted to other appropriate functional groups as defined for Z using standard synthetic transformations known to practitioners of organic synthesis. For example in Scheme 5, ester 6 is converted to a primary amide using ammonia in a suitable solvent like methanol at elevated temperature to give 11 ($Z^1$=—$CONH_2$). Dehydration of amides related to 11 may be accomplished under mild conditions using trichloroacetyl chloride and triethylamine (see: Saednya, A. *Synthesis*, 1985, 184) to provide a nitrile (12, $Z^1$=—CN). Then nitrile 12 may be converted to compound 13 of general Formulas I–V where Z is a tetrazole group using trimethyltin azide in toluene at elevated temperature.

Scheme 5

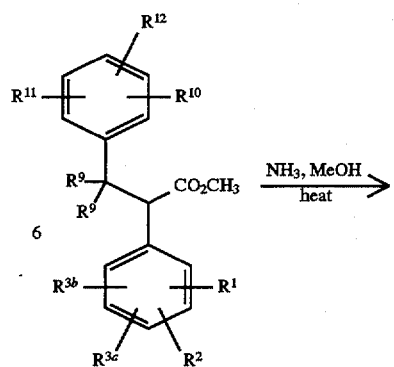

Scheme 5 -continued

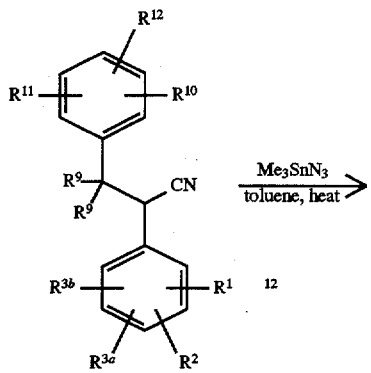

The strategy of deprotonation and alkylation at the active methylene group may be repeated on compounds of general Formula 3 when it is desired to prepare compounds of general Formulas I–V in which the substituent $R^8$ is a substituted ($C_1$–$C_6$)-alkyl group as defined above. Scheme 6 illustrates this process starting with an ester 6. Deprotonation of 6 with a strong base followed by reaction with an alkylating agent $R^8$—Q where Q is a leaving group as previously defined, produces compounds of Formula 14. Subsequent hydrolysis of ester 14 then affords compounds (15) of general Formulas I–V bearing an $R^8$ substituent and having Z equal to a carboxylic acid.

Scheme 6

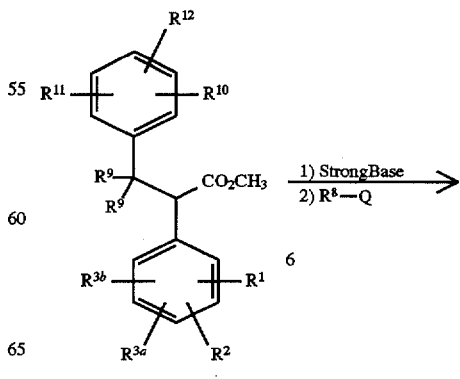

Scheme 6
-continued

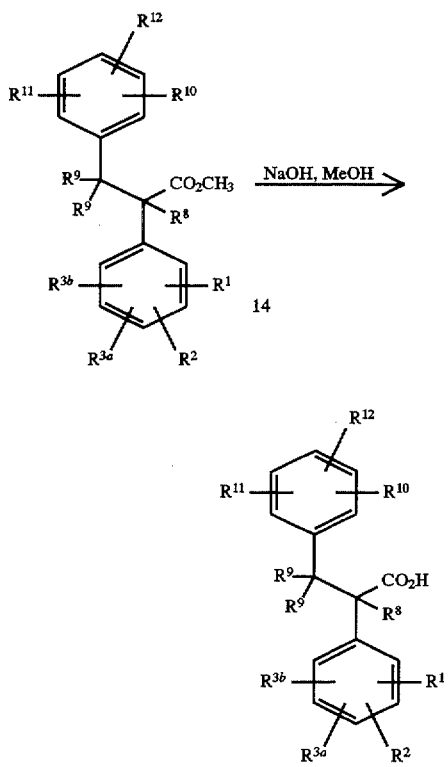

Q = Cl, Br, I, OMs, OTs, OTf, etc.

Q=Cl, Br, I, OMs, OTs, OTf, etc.

The alkylation reaction of an enolate derived from an active methylene compound 1 and the generalized alkylating agent (2) bearing a leaving group Q which is shown in Scheme 1 may also be conducted when $Z^1$ is an acylsulfonamide group such as 16 where $Z^1$=—CONHSO$_2$—R or 18 $Z^1$=—SO$_2$NHCO—R and R is either an alkyl, phenyl or heteroaryl group as previously defined. In equation 1 of Scheme 7, compound 16 is deprotonated with two equivalents of a strong base to provide a dianionic intermediate. One equivalent of the base removes the more acidic hydrogen from the acyl sulfonamide group first, then the second equivalent of base deprotonates the more weakly acidic active methylene group to form a dianion. These reactions are performed in an anhydrous aprotic solvent such as THF, dioxane or DMSO usually at low temperature and using a strong base such as a lithium, sodium or potassium dialkylamide. Alternatively, one can employ one equivalent of a weaker base such as an alkali metal hydride or alkoxide to deprotonate the acylsulfonamide group, then add a second equivalent of a strong base to form the dianion. Dianionic intermediates derived from compounds of Formula 16 are then reacted with the alkylating agent (5) and alkylation occurs at the anionic site derived from the weakly acidic active methylene group to provide compound 17 of general Formulas I–V where Z=—CONHSO$_2$—R, and R is either an alkyl, phenyl or heteroaryl group as previously defined.

Scheme 7

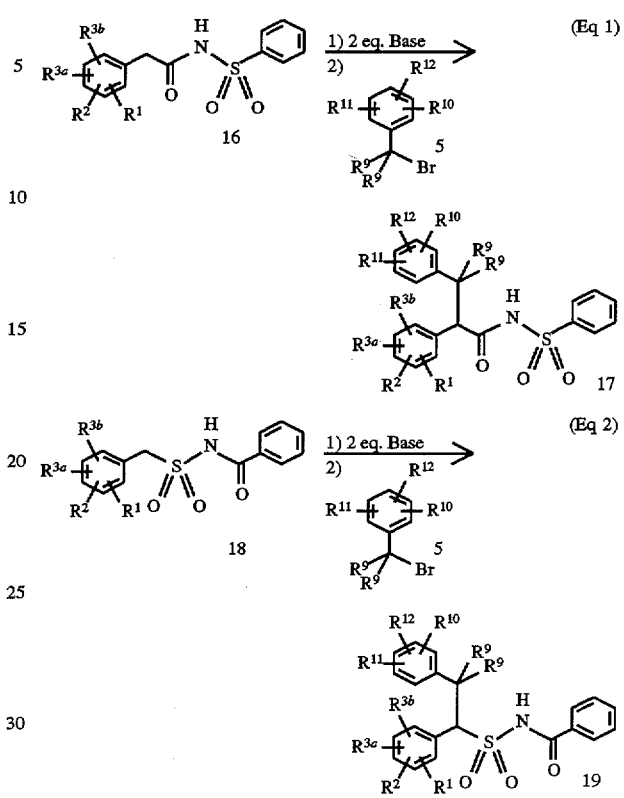

Equation 2 of Scheme 7 shows a similar strategy of acylsulfonamide dianion alkylation when it is desired to prepare compounds of general Formulas I–V wherein Z=—SO$_2$NHCO—R. In this example, initial deprotonation of 18 with the first equivalent of a base occurs at the more acidic acylsulfonamide group. A second equivalent of a strong base such as an alkyl lithium, or a lithium dialkylamide then deprotonates at the active methylene adjacent to the sulfonyl group to form a dianionic intermediate. When the alkylating agent 5 is reacted with this dianion, compound 19 of general Formulas I–V where Z=—SO$_2$NHCO—R is the product.

A second general strategy for the synthesis of the novel compounds of Formulas I–V disclosed in this invention is presented in Scheme 8. In this approach, a substituted toluene derivative of Formula 1 which bears an electron withdrawing group $Z^1$ is deprotonated in a manner similar to that described in the discussion of Scheme 1. The anion derived from 1 is then reacted with a substituted benzaldehyde derivative of Formula 20. Typically, a mixture of E and Z isomers of α,β-unsaturated compound (21) are produced. In some instances an aldol-type compound may be produced (i.e. when $Z^1$=ester), however these compounds are readily dehydrated to afford compounds of Formula 21 by reaction under acidic or basic conditions. Compounds of Formula 21 may be reduced with hydrogen in the presence of a suitable hydrogenation catalyst like palladium on carbon and compounds of general Formula 3 are formed. If necessary, the substituent $Z^1$ is then converted to one of the substituents defined previously for Z and a compound of general Formulas I–V is produced. The diastereomeric olefins (21) may be hydrogenated as a mixture to afford compounds of Formula 3. Alternatively, these isomers may be separated chromatographically or by crystallization and then hydrogenated. When it is desired to prepare optically active compounds of general Formulas I–V using this route, the individual isomers E-21 and Z-21 may be hydrogenated using an asymmetric hydrogenation catalyst such as rhodium or palladium salts in the presence of a chiral ligand.

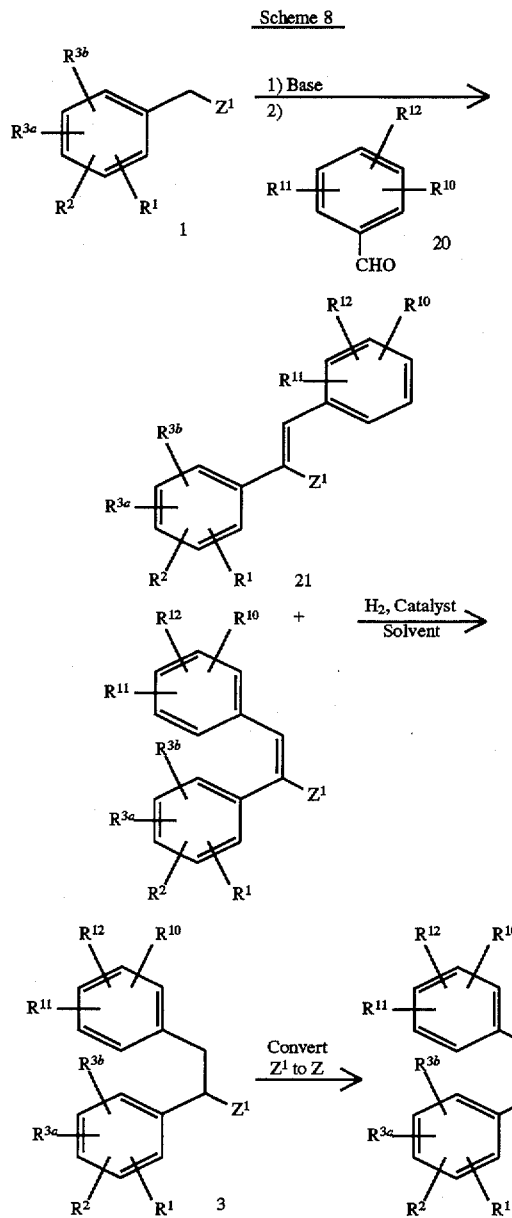

Scheme 8

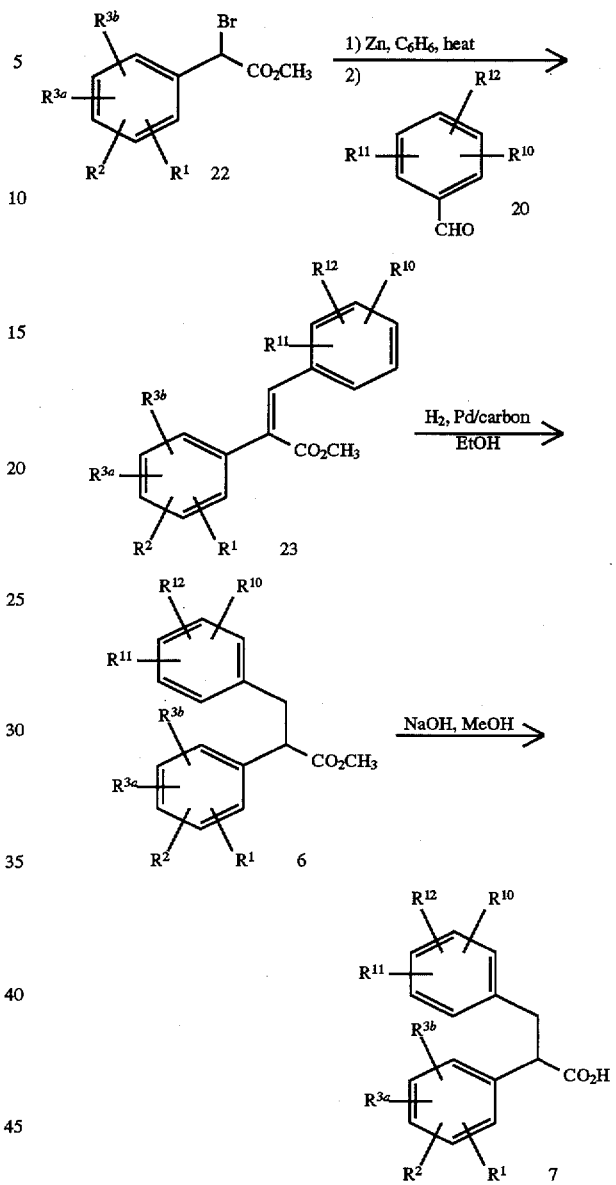

Scheme 9

Scheme 9 illustrates a more specific example using a Reformatsky reaction which is related to the process outlined above. The α-bromoarylacetic ester 22 may be reacted with zinc in a solvent like benzene or toluene at elevated temperature and the resulting bromozinc enolate condenses with the substituted benzaldehyde of Formula 20 to form the α,β-unsaturated ester 23. For the sake of simplicity, only one olefin isomer for 23 is shown here. Ester 23 is then hydrogenated in ethanol using a palladium on carbon catalyst to give 6, and hydrolysis of the ester group of 6 affords substituted acid 7 corresponding to general formulas I–V (Z=CO$_2$H).

The substituted α-bromoarylacetic esters used in this sequence may be readily prepared using the methods and techniques outlined in Scheme 10 and described in U.S. Pat. No. 5,177,095 (Merck & Co). In general, α-bromoarylacetic esters 22 are prepared from substituted arylacetic acids 24 as outlined at the top of Scheme 10. The substituted arylacetic acid 24 is first converted to the corresponding ester either by refluxing the acid in an appropriate alcohol in the presence of a catalytic amount of a strong acid such as concentrated sulfuric acid, or using other conventional methods of esterification. The resulting ester is then refluxed in carbon tetrachloride with N-bromosuccinimide and a catalytic amount of a radical initiator (i.e., AIBN or benzoylperoxide) to provide the α-bromoarylacetic acid ester 22. In some instances it is preferable to prepare the ester 22 from substituted aryl aldehydes (25). Aldehydes such as 25 can be reacted with trimethylsilyl cyanide and catalytic amounts of KCN and 18-crown-6 to provide the corresponding trimethylsilyl cyanohydrin 26, which upon further treatment with gaseous HCl and an alcohol affords the α-hydroxy ester 27. The ester 27 is then treated with triphenylphosphine and carbon tetrabromide in methylene chloride to give the 2-bromoarylacetate derivatives 22. Furthermore, substituted α-hydroxyarylacetic esters like 27 may be reduced with samarium iodide (Kasuda, K.; Inanaga, J.; Yamaguchi, M. *Tetrahedron Lett.* 1989, 2945) or iodotrimethylsilane (Sakai, T. *Bull. Chem. Soc. Jpn.* 1989, 62, 3537) to afford the compounds of general Formula 1 (Z=$CO_2Et$) employed in Schemes 1 and 8 when it is convenient to prepare these compounds from aryl-aldehydes.

2 and 20 are chosen based upon the desired substituents ($R^{9-12}$), and then the synthetic route for converting the starting materials to compounds of Formula 2 or 20 are devised using synthetic analysis familiar to those skilled in organic synthesis.

For instance, a preferred embodiment for a novel compound of Formula III disclosed in this invention is exemplified by compound 29 illustrated in Equation 1 of Scheme 11. In this example, $R^9$, $R^{10}$ and $R^{11}$ are absent, m=1, and $R^{12}$ is a trifluoromethyl group. The synthesis of compound 29 is readily accomplished using the methodology described

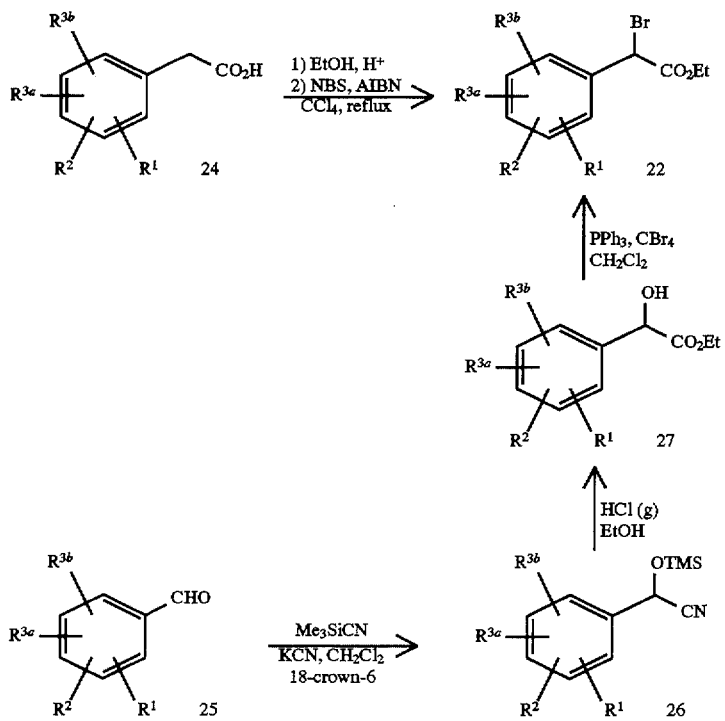

Scheme 10

The alkylating agents of general Formula 2 (Scheme 1) where m=1 or 2 and the substituted benzaldehydes of general Formula 20 (Scheme 8) may be readily available or they can be prepared in a variety of ways. The methods of preparation of 2 or 20 which are preferred are based upon consideration of which substituents ($R^9$, $R^{10}$, $R^{11}$ and $R^{12}$) are desired in the novel compounds of general Formulas I–V disclosed in this invention. Readily available starting materials for the preparation of compounds of general Formulas previously in Scheme 7 and following the procedures in Example 3. Deprotonation of the acylsulfonamide 28 of general Formula 16 with two equivalents of lithium bis(trimethylsilylamide) in THF-DMSO followed by reaction of the resulting dianion with commercially available α'-bromo-α,α,α-trifluoro-p-xylene affords 29 as shown in Equation 1 of Scheme 11.

Scheme 11

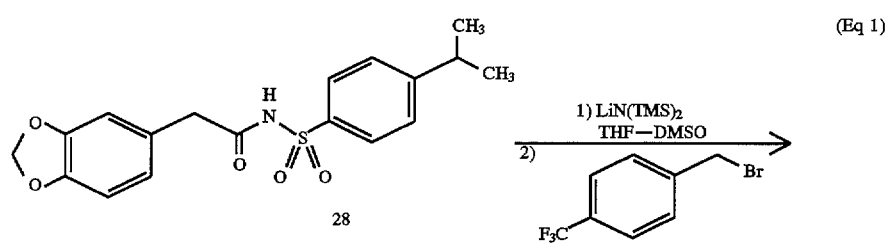

(Eq 1)

-continued
Scheme 11

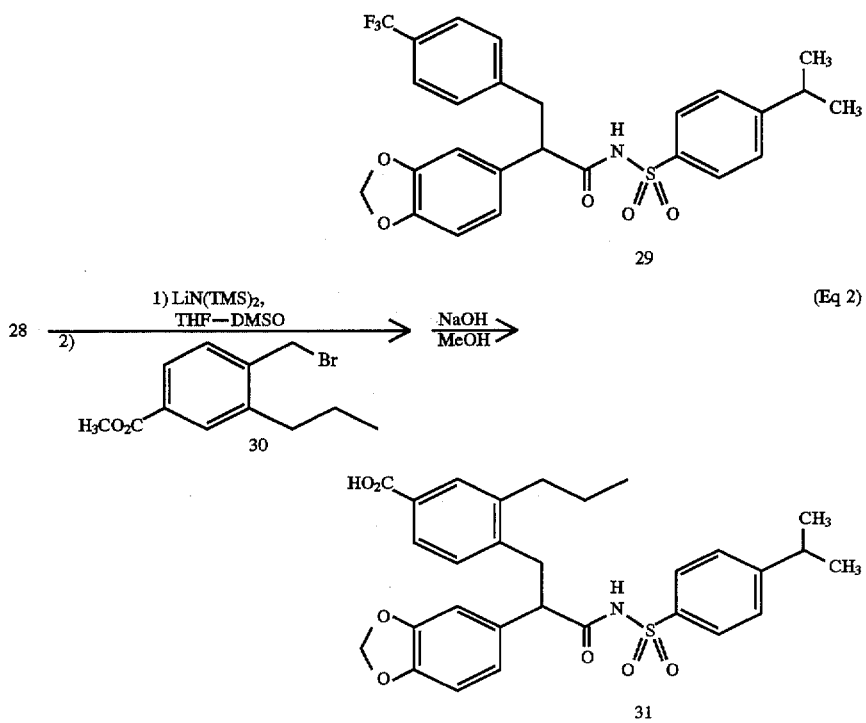

(Eq 2)

Another preferred embodiment of the novel compounds of general Formula III is exemplified by structures like 31 shown as the product of equation 2 in Scheme 11. In this case $R^{12}$ is —$CO_2H$, and $R^{10}$ is an n-propyl group, m=1, and $R^9$ and $R^{11}$ are absent. Alkylation of acysulfonamide 28 with the alkylating agent 30 (Example 5) using conditions similar to those shown in Equation 1 followed by hydrolysis of the resulting ester using sodium hydroxide in methanol affords 31.

Numerous substituted 4-hydroxybenzoic acids and their esters (i.e. 32 Scheme 12) are commercially available or are described in the chemical literature and these can serve as starting materials for the synthesis of alkylating agents of general Formula 30 when it is desired that $R^{12}$=—$CO_2H$, and that $R^{10}$ and/or $R^{11}$ be either a substituted alkyl or alkenyl group or an alkyl group optionally substituted with —($C_3$–$C_7$)-cycloalkyl groups. Furthermore, the synthesis of a number of substituted 4-hydroxybenzoic esters are described in patent application WO 91/11999 (Merck & Co.; Aug. 22, 1991) and in U.S. Pat. No. 5,177,095 (Merck & Co.; Jan. 5, 1993). Scheme 12 provides one general strategy for incorporation of a variety of such $R^{10}$ and/or $R^{11}$ substituents into 4-hydroxybenzoic esters and Scheme 13 illustrates the synthesis of alkylating agents corresponding to general Formula 30 from such substituted 4-hydroxybenzoic esters.

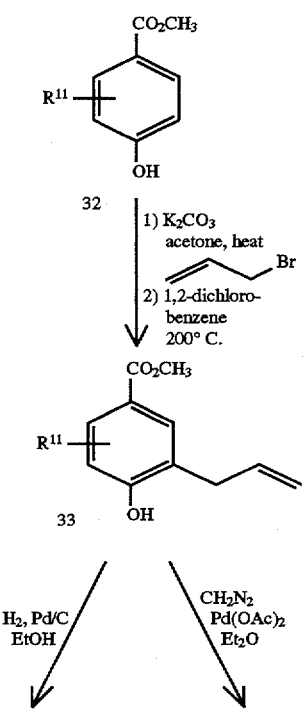

-continued
Scheme 12

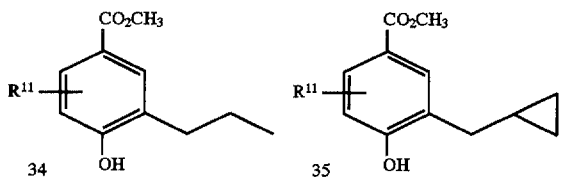

In scheme 12, compounds of Formula 32 are O-allylated with allyl bromide (shown) or a substituted allyl bromide and subjected to Claisen rearrangement at elevated temperature to afford compounds of Formula 33. The allyl substituent ($R^{10}$) may then be reduced by catalytic hydrogenation to provide 34, or alternatively olefins like 33 may be readily cyclopropanated using diazomethane in the presence of a catalytic amount of palladium acetate to afford compounds of Formula 35.

Scheme 13 illustrates a preferred synthetic route for conversion of compounds of general Formulas 32–35 to generalized alkylating agents 37 and 39. A substituted 4-hydroxybenzoic ester (32–35) is deprotonated with a suitable base and then converted to the corresponding aryl triflate using either trifluoromethanesulfonic anhydride or N-phenyltrifluoromethanesulfonimide. The aryl triflate is then converted to a styrene derivative 36 via a palladium catalyzed cross-coupling reaction with a substituted vinyl-tributylstannane. The palladium catalyzed cross coupling reactions of aryl triflates and vinylstannanes (see: Echavarren, A. M.; Stille, J. K. *J. Amer. Chem. Soc.* 1987, 109, 5478) are generally conducted in aprotic solvents such as THF, dioxane, DMF, or the like, and in the presence of a suitable palladium catalyst such as tetrakis (triphenylphosphine)palladium(0) or bis (triphenylphosphine)palladium(II) chloride. Olefin 36 may be hydroborated and the resulting primary alcohol converted to a leaving group to afford alkylating agent 37 corresponding to general Formula 2 where m=2. Alternatively, ozonolysis of the olefin 36 at low temperature in methanol or methylene chloride followed by addition of methylsulfide provides a carbonyl compound 38. If the vinylstannane used in the above palladium catalyzed cross-coupling is vinyltributyltin, then after the ozonolysis reaction a benzaldehyde (38 $R^9$=H) derivative corresponding to general Formula 20 (Scheme 8) is the product. If however, the $R^9$ group in the starting stannane is an alkyl group, then after the ozonolysis reaction an arylketone (38 $R^7$=alkyl) is the product. The last step in the preparation of compounds of Formula 39 is reduction of the carbonyl group of 38 under standard conditions with a reducing agent such as sodium borohydride, followed by conversion under standard conditions to any useful leaving group (halide, mesylate, tosylate etc.) to afford a compound of Formula 39.

Scheme 13

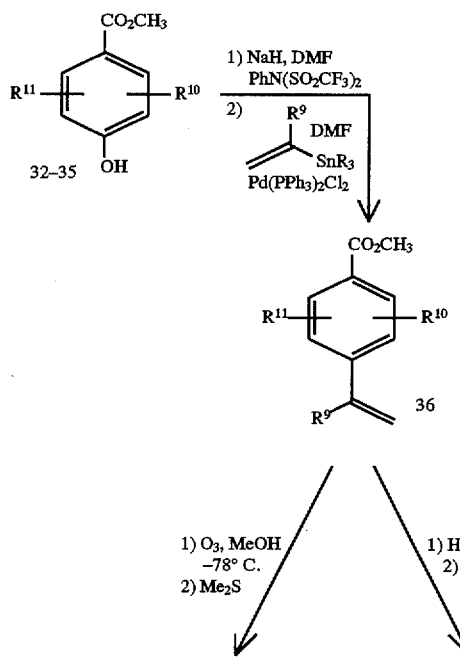

-continued
Scheme 13

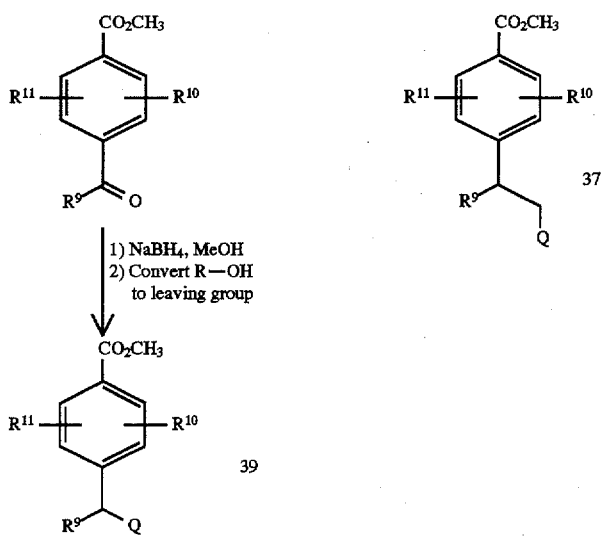

Another general method for the preparation of the substituted benzaldehydes 20 and alkylating agents of general Formula 2 (m=1) which are required for the synthesis of the novel compounds of Formulas I–V disclosed in this invention is illustrated in Scheme 14. The directed ortho-metallation and alkylation of α-aminoalkoxides derived from benzaldehydes which has recently been introduced by Comins (Comins, D. L.; Brown, J. D. *J. Org. Chem.* 1984, 49, 1078) offers flexible methodology for the synthesis of a variety of compounds of general Formula 41 as shown (Scheme 14). Reaction of the benzaldehyde derivative 40 with lithiated N,N,N'-trimethylethylenediamine provides an α-aminoalkoxide intermediate which is subsequently metallated at the ortho-position. Reaction of this ortho-metallated intermediate with the alkylating agent $R^{10}$—Q affords the more highly substituted aldehyde 41. Again, aldehydes such as 41 may be used as shown in Scheme 8 or they may be reduced to give benzyl alcohols which are then converted to alkylating agents (42) corresponding to compounds of general Formula 2.

Scheme 14

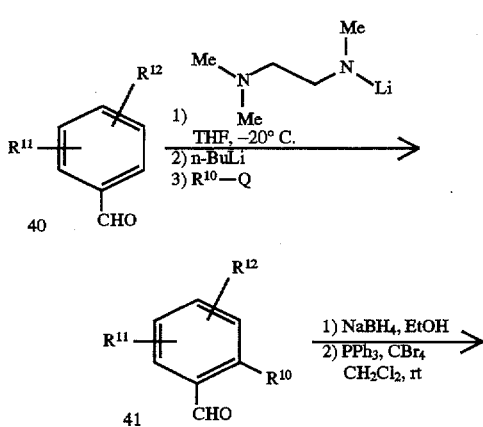

-continued
Scheme 14

The reactions described in the preceding section are performed in solvents appropriate to the reagents and materials employed and suitable for the transformation being effected. It is understood by those skilled in the art of organic synthesis that the functionality present in the substrate and in the reagents being employed should be consistent with the chemical transformations being conducted. Depending upon the reactions and techniques employed, optimal yields may require changing the order of synthetic steps or use of protecting groups followed by deprotection.

The novel compounds of general Formulas I–V described here which are useful in the treatment of diseases caused by or associated with the peptide hormone endothelin form salts with various inorganic and organic acids and bases and these salts are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be appreciated that the compounds of general Formulas I–V in this invention may be derivatised at functional groups to provide prodrug derivatives which are capable of conversion back to the parent compounds in vivo. The concept of prodrug administration has been extensively reviewed (e.g. A. A. Sinkula in Annual Reports in Medicinal Chemistry, Vol 10, R. V. Heinzelman, Ed., Academic Press, New York, 1975, Ch. 31, pp. 306–326, H. Ferres *Drugs of Today*, 1983,19, 499 and *J. Med. Chem.*, 1975, 18, 172). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formulas I–V, similar to the metabolically labile esters, which are capable of producing the parent compounds of general Formulas I–V in vivo, are within the scope of this invention.

It will be further appreciated that the majority of compounds of general Formulas I–V claimed herein are asymmetric and unless otherwise stated, are produced as racemic mixtures of enantiomers and that both the racemic compounds and the resolved individual enantiomers are considered to be in the scope of this invention. The racemic compounds of this invention may be resolved to provide individual enantiomers utilizing methods known to those skilled in the art of organic synthesis. For example, diastereoisomeric salts, esters or imides may be obtained from a racemic compound of general Formulas I–V and a suitable optically active amine, amino acid, alcohol or the like. The diastereoisomeric salts, esters or imides are separated and purified, the optically active enantiomers are regenerated and the preferred enantiomer is the more potent isomer. The resolved enantiomers of the compounds of general Formulas I–V, their pharmaceutically acceptable salts and their prodrug forms are also included within the scope of this invention.

The novel compounds of Formulas I–V disclosed in this invention which are synthesized according to the methods and techniques described in the preceding Schemes, are potent receptor antagonists of the peptide hormone endothelin. Thus, these compounds have therapeutic usefulness in preventing, decreasing or modulating the various physiological effects of endothelin discussed above, by wholly or partially blocking access of endothelin to its receptor.

The biological activity of the novel compounds of Formulas I–V disclosed in this invention may be demonstrated using the following assay protocols.

Endothelin Receptor Binding Assays

The binding of the novel compounds of this invention to the endothelin receptor was determined in accordance with the assay described in detail immediately below. It is similar to the assay described in Ambar et al., (1989) *Biochem. Biophys. Res. Commun.* 158, 195–201; and Khoog et al. (1989) *FEBS Letters.* 253, 199–202.

The endothelins (ETs) have a number of potent effects on a variety of cells, and exert their action by interacting with specific receptors present on cell membranes. The compounds described in the present invention act as antagonists of ET at the receptors. In order to identify ET antagonists and determine their efficacy in vitro, the following three ligand receptor assays were established.

Receptor binding assay using cow aorta membrane preparation:

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 mg/mL leupeptin and 7 mg/mL pepstatin A. Tissue was homogenized twice and then centrifuged for 10 minutes at 750×g at 4° C. The supernatant was filtered through cheesecloth and centrifuged again for 30 minutes at 48,000×g at 4° C. The pellet thus obtained was resuspended in the buffer solution described above (including the protease inhibitors), and aliquots were quick-frozen and stored at −70° C. until use. Membranes were diluted into 50 mM KPi, 5 mM EDTA pH 7.5 containing 0.01% human serum albumin. Assays were done in triplicate. Test compounds and 100 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1[Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration ($IC_{50}$) which gives 50% displacement of the total specifically bound [$^{125}$I]-endothelin-1 was presented as a measure of the efficacy of such compounds as ET antagonists.

Receptor binding assay using rat hippocampal membrane preparation:

Rat hippocampi were obtained from freshly sacrificed male Sprague-Dawley rats and placed in ice cold 0.25M sucrose, 5 mM tris-HCl, pH 7.4 containing 0.5 mg/mL leupeptin, 7 mg/mL pepstatin A. Hippocampi were weighed and placed in a Dounce homogenizer with 25 volumes (wet weight to volume) ice-cold sucrose buffer in the presence of protease inhibitors. Hippocampi were homogenized using a Dounce (glass-glass) homogenizer with type A pestle, with homogenizer in ice. Tissue homogenate was centrifuged at 750×g for 10 min at 4° C. Supernatant was filtered through dampened cheesecloth, and centrifuged again at 48,000×g for 30 min at 4° C. Pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000–2200 Ci/mmole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 is measured in the presence of 100 nM unlabelled endothelin-1[Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration ($IC_{50}$) which gives 50% displacement of the total specifically bound [$^{125}$I]-endothelin-1 was presented as a measure of the efficacy of such compounds as endothelin antagonists.

Receptor binding assay using cloned human ET receptors expressed in Chinese Hamster Ovary Cells:

Both endothelin receptor subtypes were cloned from a human cDNA library and were individually expressed in Chinese Hamster Ovary cells. Cells were harvested by addition of 126 mM NaCl, 5 mM KCl, 2 mM EDTA, 1 mM NaH$_2$PO$_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25–100 pM [$^{125}$I]-endothelin-1 (2000–2200 Ci/mmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pads and washed with 150 mM NaCl, 0.1% BSA.

The filters were assayed for $^{125}$I radioactivity in a gamma counter. Nondisplaceable binding of [$^{125}$I]-endothelin-1 is measured in the presence of 100 nM unlabelled endothelin-1[Endothelin-1 (ET-1) was purchased from Peptides International (Louisville, Ky.). $^{125}$I-ET-1 (2000 Ci/mMol) was purchased from Amersham (Arlington Heights, Ill.)]. Specific binding is total binding minus nondisplaceable binding. The inhibitory concentration (IC$_{50}$) which gives 50% displacement of the total specifically bound [$^{125}$I]-endothelin-1 was presented as a measure of the efficacy of such compounds as endothelin antagonists.

The binding assays described above were used to evaluate the potency of interaction of representative compounds of the invention with endothelin receptors. To determine whether these compounds were endothelin antagonists, assays which measure the ability of the compounds to inhibit endothelin-stimulated phosphatidylinositol hydrolysis were established. Rat uterus contains predominantly one of the known endothelin receptor subtypes (ET$_A$).

Phosphatidylinositol hydrolysis assays using rat uterine slices:

Diethylstilbestrol primed female Sprague-Dawley rats were sacrificed and their uteri were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 mM myo-[$^3$H]-inositol (Amersham) was added. The mince was incubated 90 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 nM endothelin-1 with and without test compounds was added to start the assay. Assays were done in quadruplicate. Samples were incubated at 37° C. under blowing O$_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Sarafotoxin S6c is a member of the endothelin family which binds preferentially to one of the known endothelin receptor subtypes (ET$_B$).

Phosphatidylinositol hydrolysis assays using rat lung slices:

Male Sprague-Dawley rats were sacrificed and their lungs were collected, dissected of fat and connective tissue and minced. Minced tissue was added to oxygenated (95% O$_2$, 5% CO$_2$) 127 mM NaCl, 25 mM NaHCO$_3$, 10 mM glucose, 2.5 mM KCl, 1.2 mM KH$_2$PO$_4$, 1.2 mM MgSO$_4$, 1.8 mM CaCl$_2$. To the tissue mince, 1.2 µM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and 3 nM sarafotoxin S6c with and without test compounds was added to start the assay. Assays were done in quadruplicate. Samples were incubated at 37° C. under blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of sarafotoxin minus the values in the absence of sarafotoxin (basal). Test sample values are the values in the presence of sarafotoxin and test sample minus basal. Inhibitory concentration (IC$_{50}$) is the concentration of test compound required to give a sample activity of 50% of control value.

Phosphatidylinositol hydrolysis assays using cloned human endothelin receptors expressed in Chinese Hamster Ovary cells:

Endothelin receptors of both receptor subtypes were cloned from a human cDNA library and were individually expressed in Chinese Hamster Ovary cells. Cells were loaded overnight by the addition of 1.2 µM myo-[$^3$H]-inositol to their growth medium. Cells were harvested by addition of 126 mM NaCl, 5 mM KCl, 2 mM EDTA, 1 mM NaH$_2$PO$_4$, 15 mM glucose, 10 mM tris/HEPES pH 7.4. Cells were washed five times by centrifugation at 250×g for 5 minutes to remove excess radiolabelled inositol. The supernatant was aspirated off, and the cells were resuspended in the same oxygenated (95% $O_2$, 5% $CO_2$) buffer containing 10 mM LiCl, aliquotted into tubes, and 0.3 nM endothelin-1 with and without test compounds was added to start the assay. Assays were done in quadruplicate. Samples were incubated at 37° C. under blowing $O_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 mL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration ($IC_{50}$) is the concentration of test compound required to give a sample activity of 50% of control value.

Using the methodology described above, representative compounds of the invention were evaluated and found to exhibit $IC_{50}$ values of at least <50 µM thereby demonstrating and confirming the utility of the compounds of the invention as effective endothelin antagonists.

Methodology for determining whether an ET-1 selective antagonist could inhibit the ET-1 mediated prostatic urethral contractions in a mongrel dog model:

On separate days, two fasted male mongrel dogs (HRP, Inc.) weighing 11.0 and 12.4 kg, are anesthetized with Sodium Pentobarbital (Steris Laboratories, Inc.) at 35 mg/kg (i.v.) to effect, followed by 4 mg/kg/hr (i.v.) infusion. A cuffed endotracheal tube is inserted and each animal is ventilated with room air using a positive displacement large animal ventilator (Harvard Apparatus) at a rate of 18 breaths/minute and an average tidal volume of 18 ml/kg body weight. Body temperature is maintained with a heating pad and heat lamp using a temperature controller (YSI) and esophageal probe. Two catheters (PE 260) are placed in the aorta via the femoral arteries (one in each artery) for administration of endothelin or phenylephrine and for continuous direct monitoring of blood pressure and heart rate using a Statham blood pressure transducer (Spectramed) and a computer system (Modular Instruments, Inc.). Two other catheters (PE 260) are placed in the vena cava via the femoral veins (one catheter in each vein) for administration of pentobarbital and the test compound, for example the compound of Example 5. A supra-pubic incision approximately one-half inch lateral to the penis is made to expose the ureters, urinary bladder, prostate, and urethra. The dome of the bladder is retracted to facilitate dissection of the ureters. The ureters are canulated with PE 90 and tied off to the bladder. Umbilical tape is passed beneath the urethra at the bladder neck and another piece of tape is placed approximately 1–2 cm. distal to the prostate. The bladder dome is incised and a Micro-tip® catheter transducer (Millar Instruments, Inc.) is advanced into the urethra. The neck of the bladder is ligated with the umbilical tape to hold the transducer. The bladder incision is sutured with 3-0 silk (purse string suture). The transducer is withdrawn until it was positioned in the prostatic urethra. The position of the Micro-tip® catheter is verified by gently squeezing the prostate and noting the large change in urethral pressure prior to ligating the distal urethra.

Experimental Protocol:

Phenylephrine (PE) (10 µg/kg, intra-arterial) is administered and pressor effects on diastolic blood pressure (DBP) and intra-urethral pressure (IUP) are noted. When blood pressure returned to baseline, endothelin-1 (ET-1) (1 nmole/kg, intra-arterial) is administered. Changes in DBP and IUP are monitored for one hour and an ET-1 selective endothelin antagonist, such as the compound of Example 5 (30 mg/kg, intra-venous) is administered. Ten to fifteen minutes later when blood pressure has stabilized, ET-1 is administered again, and inhibition of ET-1 induced effects are noted. PE is administered at the end of the experiment to verify specificity for ET-1 blockade. The dogs are euthanized with an overdose of pentobarbital followed by saturated KCl.

The drugs utilized in the experiment described above are as follows:

1) Phenylephrine, HCl (PE) (Sigma Chemical, Co.) is given at a volume of 0.05 mL/kg;
2) Endothelin-1 (ET-1) (Human, Porcine, Canine, Rat, Mouse, Bovine) (Peninsula Laboratories, Inc.) is given at a volume of 0.05 mL/kg;
3) ET-1 selective antagonist of formula I, for example the compound of Example 5 is given at a volume of about 0.3 mL/kg.

All drugs were dissolved in isotonic saline solution.

Conclusions:

ET-1 causes constriction of the prostatic urethra, as well as a complex hemodynamic response comprised of an initial depressor and subsequent presser response in anesthetized dogs. The hemodynamic and prostatic urethral responses to ET-1 is specifically inhibited by an ET-1 selective endothelin receptor antagonist. The efficacy of the ET-1 selective endothelin receptor antagonist in inhibiting the prostatic urethral presser effect of ET-1 suggests that selective antagonists of ET-1 will be useful in the treatment of urinary obstruction in benign prostatic hyperplasia.

In Situ Rat Prostate:

Male Sprague-Dawley rats (Taconic Farms) weighing 300–400 grams are anesthetized with urethane (1.75 g/kg, ip), a tracheal cannula was inserted, and the femoral artery was cannulated. Core body temperature is maintained at 37°+0.5° C. A 4–5 cm midline abdominal incision is made to expose the bladder and prostate. The prostate is separated from the bladder and surrounding capsule by blunt dissection with a forcep. A length of surgical silk is gently secured around the anterior tips of the prostate lobes. A second length of surgical silk attached to an atraumatic needle is passed through and tied to the base of the prostate approximately 10–12 mm posterior to the first tie. The posterior ligature is secured to an anchor post whereas the anterior ligature was connected to a Grass FT03 transducer (Grass Instruments, Quincy, Mass.) and maintained at a tension of 1 g. Signals from the transducer are amplified and recorded on a polygraph (Hewlett-Packard 8805B amplifiers and 7758A recorder, Palo Alto, Calif.). After equilibrating for approximately 15 min, the rats are administered pretreatment drugs (atropine 1 mg/kg, (+) propranolol 1 mg/kg) 10 min apart through the intra-arterial (IA) cannula. Thirty minutes later, ET-1 (0.3 nmoles/kg) is injected intra-arterial every thirty minutes for a total of three times. Five minutes before the third injection of ET-1, vehicle with or without an endothelin antagonist is injected IA. The response of the prostate to ET-1 is quantified by measuring the change (Δ) from baseline tension to the peak of the response during the 5-minute period after the third ET-1 injection.

The in situ rat postate protocol is utilized to determine the antagonist activity and potency of compounds of this invention to block the direct contractile effects of ET-1 on the rat prostate in vivo. In this protocol, a compound of formula 1 is demonstrated to cause a specific inhibition of ET-1 to contract the prostate and will be useful in the treatment of urinary obstruction in benign prostatic hyperplasia.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to cardiovascular smooth muscle, neural and atrial sites, endothelin receptors may also be found in gastrointestinal, kidney, lung, urogenital, uteral and placental tissues. Endothelin is a potent vasoconstrictor peptide and thus plays a role in arterial pressure-volume homeostasis. Peripheral and coronary vascular resistance is increased by endothelin, cardiac output is decreased, and plasma renin activity is increased. Endothelin causes a reduction in renal blood flow and glomerular filtration rate, while levels of atrial natriuretic factor, vasopressin, and aldosterone become elevated.

Accordingly the novel compounds of the present invention are useful in human therapy for treating asthma, hypertension, renal failure particularly post-ischemic renal failure, cyclosporin nephrotoxicity, vasospasm, cerebral and cardiac ischemia, myocardial infarction, benign prostatic hyperlasia, complications of diabetes, migraine, bone resorption, or endotoxin shock caused by or associated with endothelin, by administration to a patient in need of such treatment of a therapeutically effective amount thereof.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the an will recognize, the dosage range will generally be about 0.5 mg to 1.0 g. per patient per day which can be administered in single or multiple doses. Preferably, the dosage range will be about 0.5 mg to 500 mg. per patient per day; more preferably about 0.5 mg to 200 mg. per patient per day.

It is also considered, in accordance with the present invention, that antagonists for the endothelin receptor may be useful in preventing or reducing restenosis subsequent to denudation following angioplasty. Denudation results in myointimal thickening following angioplasty, due to increased endothelin release. Endothelin acts as a growth factor with respect to smooth muscle and fibroblastic cells, and possibly other types of cells. Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

The present invention also relates to pharmaceutical compositions for treating asthma, hypertension, renal failure, particularly post-ischemic renal failure, the vascular consequences of diabetes such as glaucoma and neuropathy, cyclosporin nephrotoxicity, vasospasm, cerebral and cardiac ischemia, myocardial infarction, or endotoxin shock caused by or associated with endothelin, comprising a therapeutically effective amount of the novel compound of this invention together with a pharmaceutically acceptable carrier therefor.

About 0.5 mg to 1.0 g. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the preparation of the compounds of Formulas I–VI and their incorporation into pharmaceutical compositions and as such are not to be considered as limiting the invention set forth in the claims appended hereto.

EXAMPLE 1

N-(3,4-methylenedioxyphenylacetyl)-4-(i-propyl) benzenesulfonamide

Step A: Preparation of N-(3,4-methylenedioxyphenylacetyl)-4-(i-propyl) benzenesulfonamide.

An oven dried 500 mL three necked round bottom flask was equipped with a magnetic stir bar, a nitrogen inlet, a septum, and a stopper. The flask was purged with nitrogen then charged with a solution of 5.083 g (28.2 mmol) of 3,4-methylenedioxyphenylacetic acid and 220 mL of anhydrous tetrahydrofuran. The contents were stirred at −78° C. and 5.11 mL of triethylamine (36.7 mmol) and 3.82 mL (31.0 mmol) of trimethylacetyl chloride were successively added. The reaction mixture was stirred at −78° C. for 15 minutes, then at 0° C. for one hour. In a separate oven dried flask, a solution of 10.120 g (50.8 mmol) of 4-(i-propyl) benzenesulfonamide dissolved in 110 mL of tetrahydrofuran was treated with 20.31 mL of a 2.5N solution of n-butyllithium in hexane at −78° C. A heavy precipitate of the deprotonated sulfonamide formed during the addition which prevented stirring. The flask and its contents were then warmed to room temperature and 60 mL of dimethylsulfoxide were added which effected solution of the lithiated sulfonamide. The solution of the lithiated sulfonamide was then transferred via cannula to the stirred 0° C. reaction mixture containing the mixed anhydride. After the addition was complete, the reaction mixture was stirred an additional 3 hours, then it was quenched by addition of excess 10% aqueous NaHSO$_4$. The majority of the THF was next removed in vacuo, and the remainder of the mixture was partitioned between EtOAc and saturated brine. The organic layer was extracted, separated, dried (MgSO$_4$), filtered and evaporated. The residue was purified on a silica gel flash chromatography column eluted with 2.5% MeOH—CHCl$_3$. The purified fractions were combined, evaporated and then recrystallized from methylene chloride-hexane to afford 6.623 g (65%) of the title compound as an off-white crystalline solid which had: mp=262°–3° C.

$^1$H NMR (400 MHz, CD$_3$OD, ppm): δ 1.24 (d, J=6.80 Hz, 6H), 2.94 (septet, J=6.80 Hz, 1H), 3.36 (s, 2H), 5.86 (s, 2H), 6.65 (s, 2H), 6.71 (s, 1H), 7.30 (d, J=8.40 Hz, 2H), 7.76 (d, J=8.40 Hz, 2H).

FAB-MS: m/e 362 (M+1).

EXAMPLE 2

N-[2-3,4-methylenedioxyphenyl)-3-phenylpropanoyl]-4-(i-propyl)benzenesulfonamide Step A: Preparation of N-[2-(3,4-methylenedioxyphenyl)-3-phenylpropanoyl]-4-(i-propyl)benzenesulfonamide.

A solution of 0.228 g (0.63 mmol) of the product of Example 1 was dissolved in 0.5 mL of anhydrous THF in an oven dried 25 mL round bottom flask and was magnetically stirred at −78° C. under a nitrogen atmosphere. A solution of lithium bis(trimethylsilyl)amide (1.89 mL; 1.0M; 1.89 mmol) was slowly added and the resulting yellow solution was stirred at −78° C. for 1 hour. At this point 150 μL (1.26 mmol) of benzyl bromide was added via syringe, the dry ice-acetone bath was removed, the reaction mixture was allowed to warm to room temperature and was stirred an additional 2 hours. The mixture was then partitioned between EtOAc and 10% aqueous NaHSO$_4$ and extracted. The organic layer was separated, washed once with water, once with saturated brine, dried (MgSO$_4$), filtered and evaporated. The residue was purified on a silica gel flash chromatography column eluted with CHCl$_3$-MeOH—NH$_4$OH (92:8:0.5). Evaporation of the purified fractions and drying in vacuo afforded 0.183 g (64%) of the title compound.

$^1$H NMR (400 MHz, CD$_3$OD, ppm): δ 1.29 (d, J=7.00 Hz, 3H), 1.30 (d, J=7.00 Hz, 3H), 2.76 (dd, J=6.00, 13.60 Hz, 1H), 3.01 (septet, J=7.00 Hz, 1H), 3.19 (dd, J=9.20, 13.60 Hz, 1H), 3.66 (d, J=6.00, 9.40 Hz, 1H), 5.90 (s, 2H), 6.62 (dd, J=1.60, 7.80 Hz, 1H), 6.66 (s, 1H), 6.67 (d, J=7.80 Hz, 1H), 6.93–6.98 (m, 2H), 7.07–7.12 (m, 3H), 7.36 (d, J=8.40 H, 2H), 7.69 (d, J=8.40 Hz, 2H).

FAB-MS: m/e 452 (M+1).

EXAMPLE 3

N-[2-(3,4-methylenedioxyphenyl)-3-(4-trifluoromethylphenyl)propanoyl]-4-(i-propyl)benzenesulfonamide Step A: Preparation of N-[2-(3,4-methylenedioxyphenyl)-3-(4-trifluoromethylphenyl)propanoyl]-4-(i-propyl)benzenesulfonamide.

To a suspension of 0.992 g (0.27 mmol) of the product of Example 1 in 0.5 mL of anhydrous THF was added 825 μL (0.82 mmol) of a 1.0M solution of lithium bis(trimethylsilyl)amide in THF at −78° C. under a nitrogen atmosphere. After stirring at −78° C. for 10 minutes, the starting material had not fully dissolved. The reaction mixture was then warmed to 0° C. (ice-water bath) and 300 μL of DMSO was added which resulted in a clear yellow solution, then 0.131 g (0.55 mmol) of α'-bromo-α,α,α-trifluoro-p-xylene was added as a solid. Stirring was maintained for 1 hour, then the reaction mixture was partitioned between EtOAc and water and extracted. The organic layer was washed with saturated brine, dried (MgSO$_4$), filtered and evaporated. The residue was purified on a silica gel flash chromatography column eluted with 2.5% MeOH—CHCl$_3$. Evaporation of the product fractions and drying in vacuo afforded 0.040 g (28%) of the title compound.

$^1$H NMR (400 MHz, CD$_3$OD, ppm): δ 1.29 (d, J=6.80 Hz, 6H), 2.86 (dd, J=6.00, 13.40 Hz, 1H), 3.01 (septet, J=6.80 Hz, 1H), 3.27 (dd, J=9.60, 13.60 Hz, 1H), 3.68 (dd, J=6.00, 9.40 Hz, 1H), 5.91 (s, 2H), 6.63 (dd, J=1.60, 7.80 Hz, 1H), 6.68 (s, 1H), 6.69 (d, J=7.80 Hz, 1H), 7.15 (d, J=7.60 Hz, 2H), 7.36 (d, J=8.80 Hz, 2H), 7.37 (d, J=7.60 Hz, 2H), 7.71 (d, J=8.40 Hz, 2H).

High Res FAB-MS Calc'd: m/e 520.1405 (M+1); Found: 520.1409.

EXAMPLE 4

N-[2-(3,4-methylenedioxyphenyl)-3-(4-carbomethoxy-2-propylphenyl)propanoyl]-4-(i-propyl)benzenesulfonamide Step A: Preparation of methyl 3-propyl-4-(trifluoromethanesulfonyloxy)benzoate.

To a solution of 5.278 g (27.2 mmol) of methyl 4-hydroxy-3-propylbenzoate in 100 mL of anhydrous DMF was added 1.630 g (40.8 mmol) of a 60% oil dispersion of sodium hydride and the reaction mixture was stirred at room temperature under a nitrogen atmosphere. After hydrogen evolution had ceased, 14.562 g (40.8 mmol) of N-phenyltrifluoromethanesulfonimide was rapidly added as a solid into the opened flask. The mixture was stirred an additional 12 hours at room temperature, then was partitioned between EtOAc and 10% aqueous NaHSO$_4$. The organic layer was separated, washed twice with water, then twice with saturated brine, dried (MgSO$_4$), filtered and evaporated. The residue was purified on a silica gel flash chromatography column eluted with 5% EtOAc-hexane. Evaporation of the purified fractions and drying in vacuo afforded 11.438 g (86%) of the title compound as a clear oil.

$^1$H NMR (400 MHz, CDCl$_3$, ppm): δ 0.96 (t, J=7.20 Hz, 3H), 1.67 (m, 2H), 2.69 (t, J=7.60 Hz, 2H), 3.90 (s, 3H), 7.30 (d, J=8.40 Hz, 1H), 7.92 (dd, J=2.00, 8.60 Hz, 1H), 8.00 (d, J=2.00 Hz, 1H).

Step B: Preparation of methyl 3-propyl-4-vinylbenzoate.

To a solution of 8.053 g (24.7 mmol) of the product of Step A and 8.136 g (25.7 mmol) of vinyltributyltin in 50 mL of anhydrous DMF was added 0.520 g (0.74 mmol) of bis(triphenylphosphine)palladium(II) chloride, the mixture was freed of air by alternate vacuum and nitrogen flush cycles, and the reaction mixture was magnetically stirred at 60° C. for 6 hours. The reaction mixture was then cooled to room temperature, partitioned between EtOAc and saturated brine, and extracted. The organic layer was washed three times with brine, separated, dried (MgSO$_4$), filtered and evaporated. The residue was purified on a silica gel flash chromatography column eluted with 3% EtOAc in hexane. Evaporation of the purified fractions and drying in vacuo afforded 3.176 g (63%) of the title compound as a clear oil.

$^1$H NMR (400 MHz, CDCl$_3$, ppm): δ 0.94 (t, J=7.20 Hz, 3H), 1.59 (m, 2H), 2.66 (t, J=7.60 Hz, 2H), 3.88 (s, 3H), 5.37 (dd, J=1.20, 11.20 Hz, 1H), 5.72 (dd, J=1.40, 17.40 Hz, 1H), 6.97 (dd, J=10.80, 17.40 Hz, 1H), 7.52 (d, J=8.40 Hz, 1H), 7.81 (s, 1H), 7.82 (dd, J=1.60, 8.40 Hz, 1H).

EI-MS: m/e 204 (M$^+$).

Step C: Preparation of methyl 4-formyl-3-propylbenzoate.

To a magnetically stirred solution of 2.796 g (14.0 mmol) of the product of Step B dissolved in a mixture of 15 mL methanol and 5 mL methylene chloride was introduced a slow stream of ozone at −78° C. After 15 minutes a persistent blue color of excess ozone was observed and the flow of ozone was stopped. Excess methylsulfide (2 mL) was added via syringe, the reaction mixture was allowed to warm to room temperature, and stirring was continued for 12 hours. The reaction mixture was then concentrated on a rotary evaporator and then purified on a silica gel flash chromatography column eluted with 5% EtOAc-hexane. Evaporation of the purified fractions and drying in vacuo afforded 1.677 g (59%) of the title compound as a clear oil.

$^1$H NMR (400 MHz, CDCl$_3$, ppm): δ 0.96 (t, J=7.20 Hz, 3H), 1.64 (m, 2H), 3.01 (t, J=7.60 Hz, 2H), 3.92 (s, 3H), 7.86 (d, J=8.00 Hz, 1H), 7.91 (d, J=1.60 Hz, 1H), 7.95 (dd, J=1.60, 8.00 Hz, 1H), 10.33 (s, 1H).

EI-MS: m/e 206 (M$^+$).

Step D: Preparation of methyl 4-hydroxymethyl-3-propylbenzoate.

To a solution of 0.609 g (2.96 mmol) of the product of Step C dissolved in 10 mL of methanol was added 0.056 g (1.48 mmol) of sodium borohydride in small portions as the reaction mixture was stirred at room temperature under a nitrogen atmosphere. After stirring for 30 minutes the excess sodium borohydride was quenched by addition of 10% aqueous NaHSO$_4$. The methanol was removed in vacuo, and the residue was partitioned between EtOAc and water. The organic layer was separated, dried (MgSO$_4$), filtered and evaporated. The residue was then purified on a silica gel flash chromatography column eluted with 20% EtOAc-hexane; evaporation of the purified fractions and drying in vacuo afforded 0.408 g (66%) of the title compound.

$^1$H NMR (400 MHz, CDCl$_3$, ppm): δ 0.96 (t, J=7.20 Hz, 3H), 1.61 (m, 2H), 1.85 (br s, 1H), 2.62 (t, J=7.60 Hz, 2H), 3.88 (s, 3H), 4.75 (s, 2H), 7.47 (d, J=8.00 Hz, 1H), 7.83 (s, 1H), 7.84 (dd, J=2.00, 8.00 Hz, 1H).

Step E: Preparation of methyl 4-bromomethyl-3-propylbenzoate.

To a magnetically stirred solution of 0.405 g (1.94 mmol) of the product of Step D dissolved in 5.0 mL of methylene chloride was added 0.638 g (2.43 mmol) of triphenylphosphine followed by 0.806 g (2.43 mmol) of carbon tetrabromide at room temperature. The reaction mixture was stirred for 30 minutes at room temperature, then the magnetic stir bar was removed and the methylene chloride was evaporated in vacuo. The residue was purified on a silica gel flash chromatography column eluted with 10% EtOAc-hexane, and evaporation of the purified fractions and solvent removal in vacuo afforded 0.496 g (94%) of the title compound.

$^1$H NMR (400 MHz, CDCl$_3$, ppm): δ 1.00 (t, J=7.60 Hz, 3H), 1.70 (m, 2H), 2.72 (t, J=8.00 Hz, 2H), 3.89 (s, 3H), 4.51 (s, 2H), 7.37 (d, J=8.00 Hz, 1H), 7.81 (dd, J=1.60, 8.00 Hz, 1H), 7.86 (d, J=1.60 Hz, 1H).

Step F: Preparation of N-[2-(3,4-methylenedioxyphenyl)-3-(4-carbomethoxy-2-propylphenyl)propanoyl]-4-(i-propyl) benzenesulfonamide.

To a magnetically stirred solution of 0.531 g (1.47 mmol) of the product of Example 1 dissolved in 2.0 mL of DMSO was added 4.40 mL of a 1.0M solution of lithium bis (trimethylsilyl)amide in THF under a nitrogen atmosphere at a temperature just warm enough to prevent the DMSO from solidifying (approximately 18° C.). During the addition of the base, the reaction mixture was further cooled to 0°–50° C. with an ice-water bath. When the addition was complete, the reaction mixture was stirred for 1 hour at 0°–5° C., then a solution of 0.496 g (1.84 mmol) of the product of Step E dissolved in 2.0 mL of THF was added via syringe. The ice-water bath was then removed and the reaction mixture was stirred at room temperature for an additional hour. The mixture was next partitioned between EtOAc and 10% aqueous NaHSO$_4$, and extracted. The organic layer was separated, washed with saturated brine, dried (MgSO$_4$), filtered, and evaporated. The residue was partially purified on a silica gel flash chromatography column eluted with 1% MeOH—CHCl$_3$. After evaporation of the product containing fractions the residue was rechromatographed on a silica gel flash chromatography column eluted with 5% EtOAc—CHCl$_3$. Evaporation of the product containing fractions and drying in vacuo afforded 0.284 (36%) of the title compound as an amorphous white solid.

$^1$H NMR (400 MHz, CD$_3$OD, ppm): δ 0.91 (t, J=7.20 Hz, 3H), 1.31 (d, J=6.80 Hz, 3H), 1.31 (d, J=6.80 Hz, 3H), 1.50 (m, 2H), 2.39–2.47 (m, 1H), 2.53–2.61 (m, 1H), 2.84 (dd, J=5.20, 14.00 Hz, 1H), 3.02 (septet, 1H), 3.28 (dd, J=9.60, 14.00 Hz, 1H), 3.70 (dd, J=5.20, 9.60 Hz, 1H), 3.89 (s, 3H), 5.92 (s, 2H), 6.64 (dd, J=1.60, 8.00 Hz, 1H), 6.68 (d, J=1.60 Hz, 1H), 6.70 (d, J=8.00 Hz, 1H), 6.95 (d, J=8.00 Hz, 1H), 7.35 (d, J=8.40 Hz, 2H), 7.51 (dd, J=1.60, 7.80 Hz, 1H), 7.67 (d, J=8.40 Hz, 2H), 7.68 (br s, 1H).

High Res FAB-MS Calc'd: m/e 552.2055 (M+1); Found: 552.2082.

EXAMPLE 5

N-[2-(3,4-methylenedioxyphenyl)-3-(4-carboxy-2-propylphenyl)propanoyl]-4-(i-propyl) benzenesulfonamide Step A: Preparation of N-[2-(3,4-methylenedioxyphenyl)-3-(4-carboxy-2-propylphenyl)propanoyl]-4-(i-propyl) benzenesulfonamide.

To a solution of 0.264 g (0.48 mmol) of the product of Example 4 in 5.0 mL of methanol was added 2.0 mL of a 5.0N solution of sodium hydroxide and the reaction mixture was stirred at room temperature under a nitrogen atmosphere for 2 hours. At the end of this period TLC analysis (CHCl$_3$-MeOH—NH$_4$OH; 80:15:1) indicated complete hydrolysis of the ester. The reaction mixture was adjusted to pH=6.0 by dropwise addition of concentrated hydrochloric acid at which point the product crystallized from the reaction mixture. The solid was collected by vacuum filtration, washed with water, and dried in vacuo to afford 0.214 g (83%) of the title compound.

$^1$H NMR (500 MHz, CD$_3$OD, ppm): δ 0.91 (t, J=7.20 Hz, 3H), 1.31 (d, J=7.00 Hz, 3H), 7.00 Hz, 3H), 1.51 (m, 2H), 2.38–2.45 (m, 1H), 2.52–2.59 (m, 1H), 2.84 (dd, J=5.50, 14.00 Hz, 1H), 3.02 (septet, J=7.00 Hz, 1H), 3.29 (dd, J=10.00, 14.00 Hz, 1H), 3.72 (dd, J=5.50, 10.00 Hz, 1H), 5.93 (s, 2H), 6.66 (dd, J=2.00, 8.00 Hz, 1H), 6.70 (d, J=2.00 Hz, 1H), 6.71 (d, J=8.00 Hz, 1H), 6.95 (d, J=8.00 Hz, 1H), 7.36 (d, J=8.50 Hz, 2H), 7.52 (dd, J=1.50, 8.00 Hz, 1H), 7.66 (d, J=8.50 Hz, 2H), 7.69 (d, J=1.50 Hz, 1H).

High Res FAB-MS Calc'd: m/e 538.1899 (M+1); Found: 538.1907. Analysis for C$_{29}$H$_{31}$NSO$_7$ Calc'd: C=64.79, H=5.81, N=2.61; Found: C=64.63, H=5.85, N=2.54.

General Procedure for dianion alkylation using butyllithium and HPLC purification is as described in Example 6:

EXAMPLE 6

N-[2-(3,4-methylenedioxyphenyl)-3-(3-methoxyphenyl)propanoyl]-4-(i-propyl) benzenesulfonamide potassium salt To a stirred solution of 0.527 g (1.46 mmol) of the product of Example 1 in 5.0 mL of anhydrous THF and 0.5 mL of anhydrous methylsulfoxide was added 1.17 mL of a 2.5M solution of n-butyllithium in hexane at −20° C. under a nitrogen atmosphere. The reaction mixture was allowed to stir and warm to 0° C. during a 90 minute period at which point 233 µL (1.60 mmol) of 3-methoxybenzyl chloride was added as a neat liquid. The reaction mixture was allowed to stir an additional two hours while warming to room temperature, then was quenched by partitioning between 10% aqueous $NaHSO_4$ and ethyl acetate. The organic layer was separated, washed with saturated NaCl, dried ($MgSO_4$), filtered and evaporated. The residue was purified by silica gel flash chromatography eluted with $CHCl_3$-MeOH—$NH_4OH$ (85:15:1), the purified fractions were combined and evaporated in vacuo. The residue (0.480 g) was dissolved in 3.0 mL of methanol and treated with 1.25 mL of a 1.0N solution of potassium hydroxide in methanol. The reaction mixture was then diluted with water (15 mL) and filtered through a 0.45 micron filter. The mixture was then desalted and purified on a Waters Millipore Delta Prep 4000 liquid chromatograph equipped with an M1000 Prep-Pak module containing a 47×300 mm Delta-Pak C18 15 µm 100 Å column cartridge. Two solvent reservoirs were employed: solvent system A (95-5 water-acetonitrile), and solvent system B (5-95 water-acetonitrile), and the column effluent was monitored simultaneously at 210 and 280 nm with a Waters model 490 UV-visible detector. The sample was pump-injected onto the column and desalted by elution (50 mL/min) with several column volumes of solvent system A. A gradient elution was then begun which had as initial conditions 100% solvent system A-0% solvent system B and reached after 30 minutes 50% solvent system A-50% solvent system B, and the fractions were collected with an ISCO Foxy 200 fraction collector. The purified fractions were combined in round bottom flasks, frozen in a −78° C. dry ice-acetone bath, and lyophilized. Combination of the purified product afforded 0.481 g (63%) of the title compound as a white lyophilized powder.

$^1$H NMR (400 MHz, $CD_3OD$, ppm): δ 1.24 (d, J=6.80 Hz, 6H), 2.74 (dd, J=6.80, 13.60 Hz, 1H), 2.92 (septet, J=6.80 Hz, 1H), 3.19 (dd, J=8.80, 14.00 Hz, 1H), 3.65–3.69 (m, 1H), 3.68 (s, 3H), 5.86 (s, 2H), 6.62–6.66 (m, 4H), 6.70 (dd, J=1.60, 8.00 Hz, 1H), 6.81 (d, J=2.00 Hz, 1H), 7.02 (dd, J=7.00, 9.20 Hz, 1H), 7.19 (d, J=8.00 Hz, 2H), 7.57 (d, J=8.00 Hz, 2H).

CI-MS: m/e 520 (M+1).

EXAMPLE 7

N-[2-(3,4-methylenedioxyphenyl)-3-(3,5-dimethoxyphenyl)propanoyl]-4-g(i-propyl) benzenesulfonamide potassium salt Using the general procedure described in Example 6 the dianion derived from the product of Example 1 (0.350 g; 0.97 mmol) was alkylated with 3,5-dimethoxybenzyl chloride. HPLC purification of the potassium salt and lyophilization afforded 0.235 g (46%) of the title compound.

$^1$H NMR (400 MHz, $CD_3OD$, ppm): δ 1.23 (d, J=7.20 Hz, 6H), 2.72 (dd, J=6.80, 13.60 Hz, 1H), 2.91 (septet, J=7.20 Hz, 1H), 3.16 (dd, J=8.80, 13.60 Hz, 1H), 3.65–3.70 (m, 1H), 3.67 (s, 6H), 5.86 (s, 2H), 6.22–6.23 (m, 1H), 6.28–6.29 (m, 2H), 6.63 (d, J=8.00 Hz, 1H), 6.72 (dd, J=1.60, 8.00 Hz, 1H), 6.82 (d, J=1.60 Hz, 1H), 7.18 (d, J=8.00 Hz, 2H), 7.55 (d, J=8.00 Hz, 2H).

ESI-MS: m/e 549 ($M^+$).

EXAMPLE 8

N-[2-(3,4-methylenedioxyphenyl)-3-(4-nitrophenyl)propanoyl]-4-(i-propyl)benzenesulfonamide potassium salt Using the general procedure described in Example 6 the dianion derived from the product of Example 1 (0.350 g; 0.97 mmol) was alkylated with 4-nitrobenzyl chloride. HPLC purification of the potassium salt and lyophilization afforded 0.341 g (66%) of the title compound.

$^1$H NMR (400 MHz, $CD_3OD$, ppm): δ 1.25 (d, J=6.80 Hz, 6H), 2.87 (dd, J=6.20, 13.60, 1H), 2.93 (septet, J=6.80 Hz, 1H), 3.28–3.34 (m, 1H), 3.67 (dd, J=6.00, 9.60 Hz, 1H), 5.88 (s, 2H), 6.66 (d, J=8.00 Hz, 1H), 6.74 (dd, J=1.60, 8.00 Hz, 1H), 6.86 (d, J=1.60 Hz, 1H), 7.19 (d, J=8.00 Hz, 2H), 7.25 (d, J=8.80 Hz, 2H), 7.59 (d, J=8.00 Hz, 2H), 7.94 (d, J=8.80 Hz, 2H).

FAB-MS: m/e 535 (M+1).

EXAMPLE 9

N-[2-(3,4-methylenedioxyphenyl)-3-(4-aminophenyl)propanoyl]-4-(i-propyl) benzenesulfonamide trifluoroacetic acid salt To a solution of 0.324 g (0.65 mmol) of the product of Example 8 dissolved in 20 mL of ethanol was added 15 mg of a 10% palladium on carbon catalyst. The mixture was shaken under a hydrogen atmosphere (50 psig) in a Parr apparatus for 12 hours at which point TLC analysis indicated complete reduction ($CHCl_3$-MeOH—$NH_4OH$; 80:15:1). The reaction mixture was then filtered through celite and evaporated. The residue was purified on a Waters Millipore Delta Prep 4000 liquid chromatograph equipped with an M1000 Prep-Pak module containing a 47×300 mm Delta-Pak C18 15 µm 100 Å column cartridge. Two solvent reservoirs were employed: solvent system A (95-5 water-acetonitrile, 0.1% trifluoroacetic acid), and solvent system B (5-95 water-acetonitrile, 0.1% trifluoroacetic acid), and the column eluent was monitored simultaneously at 210 and 280 nm with a Waters model 490 UV-visible detector. The sample was pump-injected onto the column and eluted (50 mL/min) with several column volumes of solvent system A. The solvent composition was then changed to 50% A and 50% B and the eluted fractions were collected with an ISCO Foxy 200 fraction collector. The purified fractions were combined in round bottom flasks, frozen in a −78° C. dry ice-acetone bath, and lyophilized. Combination of the purified product afforded 0.190 g (50%) of the title compound as a white lyophilized powder.

$^1$H NMR (400 MHz, $CD_3OD$, ppm): δ 1.28 (d, J=6.80 Hz, 6H), 2.84 (dd, J=6.80, 13.60 Hz, 1H), 3.00 (septet, J=6.80 Hz, 1H), 3.21 (dd, J=8.80, 13.60 Hz, 1H), 3.64 (dd, J=6.80, 3.64 Hz, 1H), 5.89 (s, 2H), 6.51 (dd, J=1.60, 8.00 Hz, 1H), 6.54 (d, J=1.60 Hz, 1H), 6.62 (d, J=8.00 Hz, 1H), 7.15–7.20 (m, 4H), 7.37 (d, J=8.40 Hz, 2H), 7.72 (d, J=8.40 Hz, 2H).

FAB-MS: m/e 466 ($M^+$-$CF_3CO_2H$).

EXAMPLE 10

N-[2-(3,4-methylenedioxyphenyl)-3-(2-ethoxyphenyl)propanoyl]-4-(i-propyl) benzenesulfonamide potassium salt Using the general procedure described in Example 6 the dianion derived from the product of Example 1 (0.35 g; 0.97 mmol) was alkylated with 2-ethoxybenzyl chloride. HPLC purification of the potassium salt and lyophilization afforded 0.277 g (54%) of the title compound.

$^1$H NMR (400 MHz, CD$_3$OD, ppm): δ 1.25 (d, J=6.80 Hz, 6H), 1.40 (t, J=6.80 Hz, 3H), 2.85 (dd, J=6.40, 13.20 Hz, 1H), 2.93 (septet, J=6.80 Hz, 1H), 3.08 (dd, J=8.40, 13.60 Hz, 1H), 3.76 (dd, J=6.40, 8.40 Hz, 1H), 3.95–4.04 (m, 2H), 5.85 (s, 2H), 6.58–6.66 (m, 3H), 6.77 (d, J=1.60 Hz, 1H), 6.79 (d, J=7.20 Hz, 1H), 6.86 (dd, J=1.60, 7.60 Hz, 1H), 7.01–7.60 (m, 1H), 7.21 (d, J=8.40 Hz, 2H), 7.60 (d, J=8.40 Hz, 2H).

FAB-MS: m/e 534 (M+1).

EXAMPLE 11

N-[2-(3,4-methylenedioxyphenyl)-3-(3,4-methylenedioxyphenyl)propanoyl]-4-(i-propyl)benzenesulfonamide potassium salt Using the general procedure described in Example 6 the dianion derived from the product of Example 1 (0.350 g; 0.97 mmol) was alkylated with 3,4-methylenedioxybenzyl chloride. HPLC purification of the potassium salt and lyophilization afforded 0.403 g (78%) of the title compound.

$^1$H NMR (400 MHz, CD$_3$OD, ppm): δ 1.24 (d, J=7.20 Hz, 6H), 2.67 (dd, J=6.80, 13.80 Hz, 1H), 2.92 (septet, J=7.20 Hz, 1H), 3.12 (dd, J=8.80, 13.80 Hz, 1H), 3.61 (dd, J=6.80, 8.80 Hz, 1H), 5.84–5.86 (m, 4H), 6.49 (dd, J=2.00, 8.00 Hz, 1H), 6.55 (d, J=8.40 Hz, 1H), 6.56 (d, J=2.00 Hz, 1H), 6.63 (d, J=8.00 Hz, 1H), 6.70 (dd, J=1.60, 8.00 Hz, 1H), 6.81 (d, J=1.60 Hz, 1H), 7.21 (d, J=8.00 Hz, 2H), 7.59 (d, J=8.00 Hz, 2H).

ESI-MS: m/e 533 (M+1).

EXAMPLE 12

N-[2-(3,4-methylenedioxyphenyl)-3-(3-n-propyloxyphenyl)propanoyl]-4-(i-propyl)benzenesulfonamide potassium salt Using the general procedure described in Example 6 the dianion derived from the product of Example 1 was alkylated with 3-n-propoxybenzyl chloride. HPLC purification of the potassium salt and lyophilization afforded 0.380 g (69%) of the title compound.

$^1$H NMR (400 MHz, CD$_3$OD, ppm): δ 1.01 (t, J=7.20 Hz, 3H), 1.24 (d, J=7.20 Hz, 6H), 1.69–1.78 (m, 2H), 2.75 (dd, J=7.00, 13.60 Hz, 1H), 2.91 (septet, J=7.20 Hz, 1H), 3.18 (dd, J=8.80, 13.60 Hz, 1H), 3.67 (dd, J=7.00, 8.80 Hz, 1H), 3.80–3.88 (m, 2H), 5.86 (s, 2H), 6.60–6.65 (m, 4H), 6.69)dd, J=2.00, 8.00 Hz, 1H), 6.80 (d, J=1.60 Hz, 1H), 7.01 (dd, J=7.60, 8.80 Hz, 1H), 7.19 (d, J=8.40 Hz, 2H), 7.57 (d, J=8.40 Hz, 2H).

FAB-MS: m/e 548 (M+1).

EXAMPLE 13

N-[2-(3,4-methylenedioxyphenyl)-3-(4-carbomethoxyphenyl)propanoyl]-4-(i-propyl)benzenesulfonamide Using the general procedure described in Example 6 the dianion derived from the product of Example 1 (2.503 g; 6.93 mmol) was alkylated with methyl 4-bromomethylbenzoate. The crude reaction mixture was partitioned between EtOAc and 10% aqueous NaHSO$_4$, separated dried and evaporated. The residue was purified on a silica gel flash chromatography eluted with CHCl$_3$-MeOH—NH$_4$OH (80:15:1). Evaporation of the purified fractions and drying in vacuo afforded 2.987 g (84%) of the title compound.

$^1$H NMR (400 MHz, CD$_3$OD, ppm): δ 1.30 (d, J=6.80 Hz, 3H), 1.30 (d, J=6.80 Hz, 3H), 2.83 (dd, J=6.00, 13.40 Hz, 1H), 3.01 (septet, J=6.80 Hz, 1H), 3.24 (dd, J=9.60, 13.40 Hz, 1H), 3.68 (dd, J=6.00, 9.60 Hz, 1H), 3.88 (s, 3H), 5.91 (s, 2H), 6.64 (dd, J=1.60, 8.00 Hz, 1H), 6.69 (d, J=8.00 Hz, 1H), 6.70 (d, J=1.60 Hz, 1H), 7.06 (d, J=8.00 Hz, 2H), 7.34 (d, J=8.40 Hz, 2H), 7.68 (d, J=8.40 Hz, 2H), 7.72 (d, J=8.00 Hz, 2H).

EXAMPLE 14

N-[2-(3,4-methylenedioxyphenyl)-3-(4-carboxyphenyl)propanoyl]-4-(i-propyl)benzenesulfonamide dipotassium salt To a solution of 0.527 g of the product of Example 13 dissolved in 1 mL of methanol was added 2 mL of a 1.0N solution of potassium hydroxide in methanol and the resulting mixture was stirred and heated at 60° C. for 3 hours. At the end of this period TLC analysis indicated complete reaction (CHCl$_3$-MeOH—NH$_4$OH, 80:15:1). The mixture was cooled to room temperature diluted with 10 mL water and filtered through a 0.45 micron filter. The mixture was then desalted and purified using the HPLC system described in Example 6 which afforded after lyophilization, 0.382 g (67%) of the title compound.

$^1$H NMR (400 MHz, CD$_3$OD, ppm): δ 1.25 (d, J=6.80 Hz, 6H), 2.81 (dd, J=6.80, 13.60 Hz, 1H), 2.94 (septet, J=6.80 Hz, 1H), 3.24 (dd, J=8.00, 13.60 Hz, 1H), 3.68 (dd, J=7.20, 8.00 Hz, 1H), 5.86 (s, 2H), 6.61 (d, J=8.40 Hz, 1H), 6.68 (d, J=8.40 Hz, 1H), 6.79 (s, 1H), 7.03 (d, J=8.00 Hz, 2H), 7.22 (d, J=8.40 Hz, 2H), 7.58 (d, J=8.40 Hz, 2H), 7.75 (d, J=8.00 Hz, 2H).

FAB-MS: m/e 572 (M+1).

EXAMPLE 15

N-[2-(3,4-methylenedioxyphenyl)-3-(4-(2-carboxylphenyl)phenyl)propanoyl]-4-(i-propyl)benzenesulfonamide dipotassium salt Step A: Preparation of N-[2-(3,4-methylenedioxyphenyl)-3-(4-(2-tert-butyloxycarbonylphenyl)phenyl)propanoyl]-4-(i-propyl)benzenesulfonamide Using the general procedure described in Example 6 the dianion derived from the product of Example 1 (0.419 g; 1.16 mmol) was alkylated with tert-butyl 2-(4-bromomethylphenyl)benzoate. The crude reaction mixture was partitioned between EtOAc and 10% aqueous NaHSO$_4$, separated dried and evaporated. The residue was purified on a silica gel flash chromatography eluted with CHCl$_3$-MeOH—NH$_4$OH (80:15:1). Evaporation of the purified fractions and drying in vacuo afforded 0.501 g (69%) of the title compound.

$^1$H NMR (400 MHz, CD$_3$OD, ppm): δ 1.20 (s, 9H), 1.21 (d, J=6.80 Hz, 6H), 2.85 (dd, J=6.40, 13.60 Hz, 1H), 2.92 (septet, J=6.80 Hz, 1H), 3.25 (dd, J=8.80, 13.60 Hz, 1H), 3.72 (dd, J=6.40, 8.80 Hz, 1H), 5.91 (s, 2H), 6.67 (br s, 2H), 6.70 (br s, 1H), 7.03 (d, J=8.40 Hz, 2H), 7.06 (d, J=8.40 Hz, 2H), 7.28 (dd, J=1.20, 7.60 Hz, 1H), 7.31 (d, J=8.40 Hz, 2H), 7.40 (dt, J=1.20, 7.60 Hz, 1H), 7.52 (dt, J=1.20, 7.60 Hz, 1H), 7.66 (dd, J=1.20, 7.60 Hz, 1H), 7.71 (d, J=8.40 Hz, 2H).

CI-MS: m/e 645 (M+NH$_4^+$).

Step B: Preparation of N-[2-(3,4-methylenedioxyphenyl)-3-(4-(2-carboxylphenyl)phenyl)propanoyl]-4-(i-propyl)benzenesulfonamide dipotassium salt To a solution of 0.501 g of the product of Step A dissolved in 4 mL of methylene chloride was added 1.0 mL of anisole and 1.0 mL of trifluoroacetic acid. The reaction mixture was stirred at room temperature for 16 hours at which point TLC analysis indicated complete reaction ($CHCl_3$-MeOH—$NH_4OH$, 80:15:1). The mixture was diluted with EtOAc, washed with saturated $NaHCO_3$, saturated NaCl, dried ($MgSO_4$), filtered and evaporated. The residue was dissolved in 2 mL of methanol and treated with 2.0 mL of a 1.0N solution of potassium hydroxide in methanol. The mixture was then desalted and purified using the HPLC system described in Example 6 which afforded after lyophilization, 0.371 g (72%) of the title compound.

$^1$H NMR (400 MHz, $CD_3OD$, ppm): δ 1.22 (d, J=6.80 Hz, 6H), 2.82 (dd, J=6.80, 13.60 Hz, 1H), 2.90 (septet, J=6.80 Hz, 1H), 3.22 (dd, J=8.80, 13.60 Hz, 1H), 3.74 (dd, J=6.80, 8.80 Hz, 1H), 5.87 (s, 2H), 6.64 (d, J=8.00 Hz, 1H), 6.73 (dd, J=1.60, 8.00 Hz, 1H), 6.83 (d, J=1.60 Hz, 1H), 7.09 (d, J=8.00 Hz, 2H), 7.21 (d, J=8.40 Hz, 2H), 7.23–7.31 (m, 3H), 7.34 (d, J=8.00 Hz, 2H), 7.45 (d, J=6.80 Hz, 1H), 7.60 (d, J=8.40 Hz, 2H).

ESI-MS: m/e 648 (M+1).

EXAMPLE 16

N-[2-(3,4-methylenedioxyphenyl)-3-(4-methylsulfonylphenyl)propanoyl]-4-(i-propyl) benzenesulfonamide potassium salt Using the general procedure described in Example 6 the dianion derived from the product of Example 1 (0.256 g; 0.71 mmol) was alkylated with 4-methylsulfonylbenzyl chloride. HPLC purification of the potassium salt and lyophilization afforded 0.212 g (52%) of the title compound.

$^1$H NMR (400 MHz, $CD_3OD$, ppm): δ 1.26 (d, J=6.80 Hz, 6H), 2.87 (dd, J=6.00, 13.60 Hz, 1H), 2.94 (septet, J=6.80 Hz, 1H), 3.06 (s, 3H), 3.33 (dd, J=9.60, 13.60 Hz, 1H), 3.67 (dd, J=6.00, 9.60 Hz, 1H), 5.87 (s, 2H), 6.65 (d, J=7.60 Hz, 1H), 6.73 (dd, J=1.60, 8.00 Hz, 1H), 6.84 (d, J=1.60 Hz, 1H), 7.23 (d, J=8.40 Hz, 2H), 7.30 (d, J=8.40 Hz, 2H), 7.58 (d, J=8.40 Hz, 2H), 7.68 (d, J=8.40 Hz, 2H).

FAB-MS: m/e 568 (M+1).

EXAMPLE 17

N-[2-(3,4-methylenedioxyphenyl)-3-(2-naphthyl) propanoyl]-4-(i-propyl)benzenesulfonamide potassium salt Using the general procedure described in Example 6 the dianion derived from the product of Example 1 (0.259 g; 0.72 mmol) was alkylated with 2-naphthylmethyl bromide. HPLC purification of the potassium salt and lyophilization afforded 0.310 g (80%) of the title compound.

$^1$H NMR (400 MHz, $CD_3OD$, ppm): δ 1.17 (d, J=6.80 Hz, 6H), 2.82 (septet, J=6.80 Hz, 1H), 2.94 (dd, J=6.00, 13.60 Hz, 1H), 3.39 (dd, J=9.60, 13.60 Hz, 1H), 3.86 (dd, J=6.00, 9.60 Hz, 1H), 5.86 (d, J=1.00 Hz, 1H), 5.87 (d, J=1.00 Hz, 1H), 6.62 (d, J=7.60 Hz, 1H), 6.79 (dd, J=1.60, 8.00 Hz, 1H), 6.91 (d, J=1.60 Hz, 1H), 6.92 (d, J=8.40 Hz, 2H), 7.28 (dd, J=1.60, 8.40 Hz, 1H), 7.38–7.42 (m, 4H), 7.55 (s, 1H), 7.63–7.69 (m, 2H), 7.76–7.82 (m, 1H).

FAB-MS: m/e 501 ($M^+$-K).

EXAMPLE 18

N-[2-(3,4-methylenedioxyphenyl)-3-(4-hydroxymethyl-2-propylphenyl)propanoyl]-4-(i-propyl)benzenesulfonamide Step A: Preparation of methyl 4-tert-butyldimethylsilyloxybenzoate.

To a solution of 16.618 g (0.100 mol) of methyl 4-hydroxymethylbenzoate and 12.828 g (0.105 mol) of 4-dimethylaminopyridine in $^{125}$ mL of methylene chloride was added 15.827 g (0.105 mol) of tert-butyldimethylchlorosilane and the reaction mixture was stirred at room temperature for 16 hours. The reaction mixture was then partitioned between methylene chloride and water and extracted. The organic layer was washed with 1.0N hydrochloric acid, water, then separated, dried ($MgSO_4$), filtered and evaporated. The residue was used directly in the next step without further purification or characterization.

Step B: Preparation of 4-tert-butyldimethylsilyloxybenzyl alcohol.

To a solution of the crude product from Step A dissolved in 150 mL of anhydrous THF was added 50 mL of a 1.0M solution of lithium aluminum hydride in THF at 0° C. under a nitrogen atmosphere. The reaction mixture was allowed to warm to room temperature and was stirred for 2 hours. The reaction was then quenched by sequential addition of 1.90 mL of water, 1.90 mL of 15% aqueous sodium hydroxide, and 5.70 mL water. The granular aluminum salts were separated from the reaction mixture by vacuum filtration through Celite, then the filtrate was evaporated in vacuo. The residue was redissolved in methylene chloride, dried ($MgSO_4$), filtered, and evaporated. Removal of the residual solvent in vacuo afforded 20.290 g (80% two steps) of the title compound as a colorless oil.

Step C: Preparation of 4-tert-butyldimethylsilyloxybenzaldehyde.

A mixture of 150 mL of methylene chloride and 11.223 g (0.088 mol) of oxalyl chloride was placed in a flame dried 500 mL three necked round bottom flask equipped with a stopper, septum, nitrogen inlet, and a magnetic stir bar. The flask and its contents were chilled to −55° C. and a solution of 13.816 g (0.177 mol) of DMSO in 35 mL methylene chloride was added with stirring under nitrogen. Two to three minutes after the addition was complete, a solution of 20.290 g (0.080 mol) of the product of Step B dissolved in 80 mL of methylene chloride was added and the reaction mixture was stirred an additional 15 minutes at −55° C. Triethylamine (40.668 g; 0.402 mol) was then is added, the reaction was stirred an additional 5 minutes at −55° C. then allowed to warm to room temperature. The mixture was then partitioned between water and methylene chloride, and extracted. The organic layer was washed with 2.0N hydrochloric acid, water, dried ($MgSO_4$), filtered, and evaporated. The residual oil was purified on a silica gel flash chromatography column fluted with 5% EtOAc-hexane. Evaporation of the purified fractions and drying in vacuo afforded 17.489 g (87%) of the title compound.

$^1$H NMR (400 MHz, $CDCl_3$, ppm): ∂ 0.09 (s, 6H), 0.93 (s, 9H), 4.79 (s, 2H), 7.46 (d, J=8.40 Hz, 2H), 7.83 (d, J=8.40 Hz, 2H), 9.97 (s, 1H).

Step D: Preparation of 4-tert-butyldimethylsilyloxy-2-propylbenzaldehyde.

To a solution of 1.226 g (0.012 mol) of N,N,N'-trimethylethylenediamine in 25 mL of anhydrous THF was added 4.40 mL of a 2.5M solution of n-butyllithium in THF at −20° C. under a nitrogen atmosphere. After 15–20 minutes, 2.501 g (0.010 mol) of the product of Step C dissolved in 5.0 mL of THF was added and the reaction mixture was stirred at −20° C. for an additional 15–20 minutes. Next, 12.0 mL of a 2.5M solution of n-butyllithium in THF was added to the reaction, the cooling bath was removed and the mixture was stirred at room temperature for 3.5 hours. At the end of this period, the reaction mixture was cooled to −40° C. and 5.85 mL of 1-iodopropane was added via syringe. The reaction mixture was then allowed to slowly warm to room temperature and was stirred for 16 hours. The mixture was then partitioned between diethylether and 10% aqueous NaHSO$_4$ and extracted. The organic layer was separated, dried (MgSO$_4$), filtered, and evaporated. The residue was partially purified on a silica gel flash chromatography column eluted with 5% EtOAc-hexane. The semi-purified fractions were combined and evaporated, then rechromatographed on a silica gel flash chromatography column eluted with 50% CHCl$_3$-hexane. Evaporation of the purified fractions and solvent removal in vacuo afforded 0.386 g (13%) of the title compound.

$^1$H NMR (400 MHz, CDCl$_3$, ppm): ∂ 0.09 (s, 6H), 0.93 (s, 9H), 0.96 (t, J=7.20 Hz, 3H), 1.59–1.67 (m, 2H), 2.98 (t, J=7.60 Hz, 2H), 4.75 (s, 3H), 7.20 (s, 1H), 7.28 (d, J=8.00 Hz, 1H), 7.78 (d, J=8.00 Hz, 1H), 10.23 (s, 1H).

EI-MS: m/e 292 (M$^+$).

Step E: Preparation of 4-tert-butyldimethylsilyloxy-2-propylbenzyl alcohol.

To a solution of 0.386 g (1.32 mmol) of the product of Step D dissolved in 4.0 mL of ethanol was added 0.025 g (0.66 mmol) of sodium borohydride and the reaction mixture was stirred at room temperature for 30 minutes. The excess reducing agent was then quenched with 10% aqueous NaHSO$_4$ and the methanol was removed in vacuo. The residue was partitioned between EtOAc and water and extracted, the organic layer was separated, dried (MgSO$_4$), filtered and evaporated. The residue was purified on a silica gel flash chromatography column eluted with 15% EtOAc-hexane. Evaporation of the purified fractions and solvent removal in vacuo afforded 0.246 g (63%) of the title compound.

$^1$H NMR (400 MHz, CDCl$_3$, ppm): ∂ 0.08 (s, 6H), 0.92 (s, 9H), 0.96 (t, J=7.20 Hz, 3H), 1.55 (br s, 1H), 1.55–1.67 (m, 2H), 2.63 (t, J=7.60 Hz, 2H), 4.69 (d, J=8.80 Hz, 2H), 7.14–7.15 (m, 2H), 7.28–7.32 (m, 1H).

Step F: Preparation of 4-tert-butyldimethylsilyloxy-2-propylbenzyl bromide.

Using the procedure described in Step E of Example 4 the product of Step E is converted to the title compound.

Step G: Preparation of N-[2-(3,4-methylenedioxyphenyl)-3-(4-tert-butyldimethylsilyloxymethyl-2-propylphenyl)propanoyl]-4-(i-propyl)benzenesulfonamide.

Using the procedure described in Step F of Example 4, N-(3,4-methylenedioxyphenylacetyl)-4-(i-propyl)benzenesulfonamide (Example 1) is reacted with the product of Step F to provide the title compound.

Step H: Preparation of N-[2-(3,4-methylenedioxyphenyl)-3-(4-hydroxymethyl-2-propylphenyl)propanoyl]-4-(i-propyl)benzenesulfonamide.

Reaction of the product of Step G with one equivalent of tetra-n-butylammonium fluoride in a suitable solvent such as THF followed by a standard workup and chromatographic purification provides the title compound.

EXAMPLES 19–21

Following the procedures, described above and in the schemes and description preceding the Examples the following can be prepared:

N-(4-benzoyl)-[1-(3,4-methylenedioxyphenyl)-2-(4-carboxy-2-propylphenyl)ethane]sulfonamide, N-(4-(i-propyl)benzoyl)-[1-(3,4-methylenedioxyphenyl)-2-(4-carboxy-2-propylphenyl)ethane]sulfonamide, and N-(4-(t-butyl)benzoyl)-[1-(3,4-methylenedioxyphenyl)-2-(4-carboxy-2-propylphenyl)ethane]sulfonamide.

What is claimed is:

1. A compound of structural Formula I:

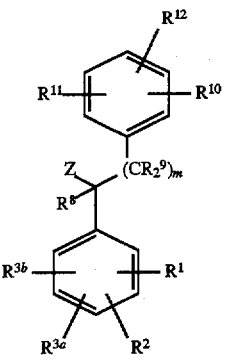

or a pharmaceutically acceptable salt thereof, wherein:

R$^1$ and R$^2$ on adjacent carbon atoms are joined together to form a heterocyclic oxygen containing ring structure containing the following group —O—[C(R$^6$)(R$^6$)]—O—;

R$^{3a}$ and R$^{3b}$ are independently:
 (a) H,
 (b) F, Cl, Br, or I,
 (c) —NO$_2$,
 (d) —NH$_2$,
 (e) —NH(C$_1$–C$_4$)-alkyl,
 (f) —N[(C$_1$–C$_4$)-alkyl]$_2$,
 (g) —SO$_2$NHR$^7$,
 (h) —CF$_3$,
 (i) (C$_1$–C$_4$)-alkyl,
 (j) —OR$^7$,
 (k) —S(O)$_n$—(C$_1$–C$_4$)-alkyl,
 (l) —NHCO—(C$_1$–C$_4$)-alkyl,
 (m) —NHCO—O(C$_1$–C$_4$)-alkyl,
 (n) —CH$_2$O—(C$_1$–C$_4$)-alkyl,
 (o) —O—(CH$_2$)$_x$—OR$^7$,
 (p) —CONR$^7$R$^{16}$, or
 (q) —COOR$^7$;

m is: 1 or 2;
n is: 0, 1 or 2;
x is: 2, 3 or 4;
R$^6$ is:
 (a) H,
 (b) F, or
 (c) (C$_1$–C$_4$)-alkyl unsubstituted or substituted with one of the following substituents:
  i) —OH,
  ii) —NR$^7$R$^{16}$,
  iii) —COOR$^7$,
  iv) —CONHR$^7$, or
  v) —CONR$^7$R$^6$;

R$^7$ is:
 (a) H,
 (b) (C$_1$–C$_6$)-alkyl,
 (c) phenyl;
 (d) benzyl, or
 (e) (C$_3$–C$_7$)-cycloalkyl;

R$^8$ is:
 (a) H,
 (b) (C$_1$–C$_6$)-alkyl, unsubstituted or substituted with a substituent selected from the group consisting of:
  i) -phenyl,
  ii) —(C$_3$–C$_7$)-cycloalkyl,
  iii) —NR$^7$R$^{16}$, iv) -morpholin-4-yl,
v) —OH,
vi) —CO$_2$R$^7$, or
vii) —CON(R$^7$)$_2$,
(c) phenyl, unsubstituted or substituted with a substituent selected from the group consisting of:
i) (C$_1$-C$_4$)-alkyl
ii) —O—(C$_1$-C$_4$)-alkyl
iii) —CONR$^7$R$^{16}$,
iv) F, Cl, Br or I,
v) —COOR$^7$, or
vi) 2,3-, or 3,4-methylenedioxy;

R$^9$ is:
(a) H,
(b) (C$_1$-C$_6$)-alkyl, unsubstituted or substituted with a substituent selected from the group consisting of:
i) -phenyl,
ii) —(C$_3$-C$_7$)-cycloalkyl,
iii) —NR$^7$R$^{16}$,
iv) —OH,
v) —O—(C$_1$-C$_4$)-alkyl,
vi) —CF$_3$,
vii) —COOR$^7$,
viii) —S(O)$_n$—(C$_1$-C$_4$)-alkyl, or
ix) —CON(R$^7$)$_2$;
(c) (C$_3$-C$_7$)-cycloalkyl,
(d) F, Cl, Br, I,
(e) —COOR$^7$,
(f) —CON(R$^7$)$_2$,
(g) -perfluoro-(C$_1$-C$_4$)-alkyl,
(h) —O—(CH$_2$)$_x$—OR$^7$, or
(i) —S(O)$_n$—(C$_1$-C$_4$)-alkyl;

R$^{10}$ and R$^{11}$ are independently:
(a) H,
(b) (C$_1$-C$_6$)-alkyl, unsubstituted or substituted with (C$_3$-C$_7$)-cycloalkyl,
(c) (C$_2$-C$_6$)-alkenyl,
(d) (C$_2$-C$_6$)-alkynyl,
(e) Cl, Br, F, I,
(f) (C$_1$-C$_6$)-alkoxy,
(g) when R$^{10}$ and R$^{11}$ are on adjacent carbons, they can be joined to form a phenyl ring,
(h) perfluoro-(C$_1$-C$_6$)-alkyl,
(i) (C$_3$-C$_7$)-cycloalkyl, unsubstituted or substituted with (C$_1$-C$_6$)-alkyl,
(j) phenyl,
(k) (C$_1$-C$_6$)-alkyl-S(O)$_n$—(CH$_2$)$_n$—,
(l) hydroxy-(C$_1$-C$_6$)-alkyl,
(m) —CF$_3$,
(n) —CO$_2$R$^7$,
(o) —OH,
(p) —NR$^7$R$^{16}$,
(q) —[(C$_1$-C$_6$)-alkyl]NR$^7$R$^{16}$,
(r) —NO$_2$,
(s) —(CH$_2$)$_n$—SO$_2$—N(R$^7$)$_2$,
(t) —NR$^7$CO—(C$_1$-C$_4$)-alkyl,
(u) —CON(R$^7$)$_2$, or
(v) when R$^{10}$ and R$^{11}$ are on adjacent carbons, they can join together to form a ring, where R$^{10}$ and R$^{11}$ are represented by —O—CH$_2$—O—;

R$^{12}$ is:
(a) H
(b) (C$_1$-C$_6$)-alkyl, unsubstituted or substituted with one or two substituents selected from the group consisting of:
i) —OH,
ii) —O—(C$_1$-C$_4$)-alkyl,
iii) —O—(C$_1$-C$_4$)-cycloalkyl,
iv) —S(O)$_n$—(C$_1$-C$_4$)-alkyl,
iv) —NR$^7$—(C$_1$-C$_4$)-alkyl,
v) —N$^7$R$^{16}$,
vi) —COOR$^7$,
vii) —CONHR$^7$,
viii) —OCOR$^{16}$,
ix) —CONR$^7$R$^{16}$,
x) —NR$^7$CONR$^7$R$^{16}$,
xi) —NR$^7$COOR$^{16}$,
xii) —C(R$^6$)(OH)—C(R$^6$)(R$^7$)(OH), or
xiii) —SO$_2$NR$^7$R$^{16}$,
(c) (C$_3$-C$_7$)-cycloalkyl,
(d) —C(R$^6$)(OH)—C(R$^6$)(R$^7$)(OH),
(e) -perfluoro-(C$_1$-C$_4$)-alkyl,
(f) —OR$^7$,
(g) —COOR$^{13}$,
(h) —COR$^{16}$,
(i) —CONR$^7$R$^{16}$,
(j) —CONHSO$_2$R$^{16}$;
(k) —NO$_2$,
(l) —NH$_2$,
(m) —NR$^7$R$^{16}$,
(n) —NR$^7$CONR$^7$R$^{16}$,
(o) —NR$^7$COOR$^{16}$,
(p) —NR$^7$COR$^{16}$,
(q) —NR$^7$CONHSO$_2$R$^{16}$,
(s) —NR$^7$SO$_2$NH$_6$,
(t) —NR$^7$SO$_2$NHR$^{16}$,
(u) —NR$^7$SO$_2$N(R$^{16}$)$_2$,
(v) —NR$^7$SO$_2$NHCOR$^{16}$,
(w) —SO$_2$NR$^7$R$^{16}$,
(x) —S(O)$_2$—NR$^7$COR$^{16}$,
(y) —S(O)$_2$—NR$^7$COOR$^{16}$,
(z) —S(O)$_2$—NR$^7$CONHR$^{16}$,
(aa) —S(O)$_2$—NR$^7$CONH$_2$, or
(ab) —S(O)$_n$—(C$_1$-C$_4$)-alkyl;

Z is:
(a) —CO$_2$R$^{13}$,
(b) CONH(tetrazol-5-yl),
(c) —CONHSO$_2$-phenyl, wherein phenyl is unsubstituted or substituted with one or two substituents selected from the group consisting of:
i) (C$_1$-C$_4$)-alkyl,
ii) —O—(C$_1$-C$_4$)-alkyl,
iii) —CONR$^7$R$^{16}$,
iv) F, Cl, Br or I,
v) —COOR$^7$,
vi) (C$_1$-C$_4$)-perfluoroalkyl,
vii) (C$_3$-C$_7$)-cycloalkyl,
viii) NR$^7$R$^{16}$,
ix) SO$_2$NR$^7$R$^{16}$,
x) hydroxy, or
xi) 2,3-, or 3,4-methylenedioxy;
(d) —CONHSO$_2$—(C$_1$-C$_8$)-alkyl, wherein the alkyl group is unsubstituted or substituted with one or two substituents selected from the group consisting of:
i) —OH,
ii) —O—(C$_1$-C$_4$)-alkyl,
iii) —S(O)$_n$—(C$_1$-C$_4$)-alkyl,
iv) —NR$^7$—(C$_1$-C$_4$)-alkyl,
v) —NHR$^7$,
vi) —COOR$^7$,
vii) —CONHR$^7$,
viii) —OCOR$^{16}$, or
ix) —CONR$^7$R$^{16}$,
(e) —CONHSO$_2$—(C$_1$-C$_4$)-perfluoroalkyl, (f) —CONHSO$_2$—(C$_3$–C$_7$)cycloalkyl, (g) —CONHSO$_2$-heteroaryl, wherein heteroaryl is defined as furyl, unsubstituted or substituted with (C$_1$–C$_6$)-alkyl, (h) -tetrazol-5-yl, (i) —CONHSO$_2$NH-phenyl, wherein phenyl is unsubstituted or substituted with one or two substituents selected from the group consisting of:
  i) (C$_1$–C$_4$)-alkyl,
  ii) —O—(C$_1$–C$_4$)-alkyl,
  iii) —CONR$^7$R$^{16}$,
  iv) F, Cl, Br or I,
  v) —COOR$^7$,
  vi) (C$_1$–C$_4$)-perfluoroalkyl,
  vii) (C$_3$–C$_7$)-cycloalkyl,
  viii) NR$^7$R$^{16}$,
  ix) SO$_2$NR$^7$R$^{16}$,
  x) hydroxy, or
  xi) 2,3-, or 3,4-methylenedioxy;

(j) —CONHSO$_2$NH—(C$_1$–C$_8$)-alkyl, wherein the alkyl group is unsubstituted or substituted as defined in Z(d), (k) —CONHSO$_2$NH—(C$_1$–C$_4$)-perfluoroalkyl, (l) —CONHSO$_2$NH—(C$_3$–C$_7$)-cycloalkyl, (m) —CONHSO$_2$NH-heteroaryl, wherein heteroaryl is defined as furyl, unsubstituted or substituted with (C$_1$–C$_6$)-alkyl;

(n) —SO$_2$NHCO phenyl, wherein phenyl is as defined in Z(c) above, (o) —SO$_2$NHCO—(C$_1$–C$_8$)-alkyl, wherein the alkyl group is unsubstituted or substituted as defined in Z(d), (p) —SO$_2$NHCO—(C$_1$–C$_4$)-perfluoroalkyl, (q) —SO$_2$NHCO-heteroaryl, wherein heteroaryl is as defined in Z(g) above, (r) —SO$_2$NHCON(R$^{16}$)$_2$ wherein the R$^{16}$ groups are the same or different, (s) —SO$_2$NHCOOR$^{16}$, (t) —PO(OR$^7$)$_2$, wherein the R$^7$ groups are the same or different, or (u) —PO(R$^{16}$)OR$^7$;

R$^{13}$ is:

(a) H, (b) (C$_1$–C$_6$)-alkyl, (c) CHR$^{14}$—O—COR$^{15}$, (d) CH$_2$CH$_2$—N[(C$_1$–C$_2$)-alkyl]$_2$, (e) CH$_2$CH$_2$—N[CH$_2$CH$_2$]$_2$O, (f) (CH$_2$CH$_2$O)$_y$—O—[(C$_1$–C$_4$)-alkyl], wherein y is 1 or 2, (g) phenyl, naphthyl, CH$_2$-phenyl or CH$_2$-naphthyl, where phenyl or naphthyl is substituted or unsubstituted with CO$_2$—(C$_1$–C$_6$)-alkyl,

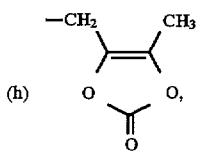

(h)

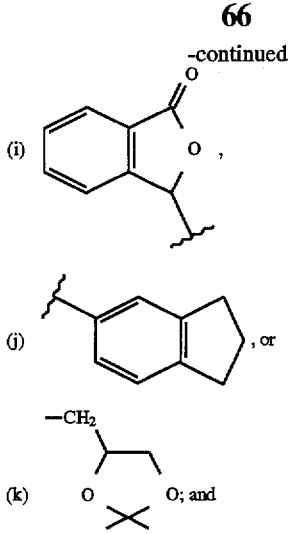

(i)

(j) , or (k) —CH$_2$

O   O; and

R$^{14}$ and R$^{15}$ independently are (C$_1$–C$_6$)-alkyl or phenyl; and

R$^{16}$ is
  (a) —(C$_1$–C$_6$)-alkyl,
  (b) —(C$_1$–C$_4$)-perfluoroalkyl,
  (c) —(C$_1$–C$_4$)-polyfluoroalkyl,
  (d) -phenyl, unsubstituted or substituted with a substituent selected from the group consisting of:
    i) (C$_1$–C$_4$)-alkyl,
    ii) —O—(C$_1$–C$_4$)-alkyl,
    iii) —CONR$^7$R$^{16}$,
    iv) F, Cl, Br or I,
    v) —COOR$^7$,
  (e) —(C$_1$–C$_4$)-alkyl-phenyl, wherein the phenyl is unsubstituted or substituted with a substituent selected from the group consisting of:
    i) (C$_1$–C$_4$)-alkyl,
    ii) —O—(C$_1$–C$_4$)-alkyl,
    iii) —CONR$^7$R$^{16}$,
    iv) F, Cl, Br or I,
    v) —COOR$^7$, or
  (f) —(C$_3$–C$_7$)-cycloalkyl.

2. A compound of structural formula III$_b$:

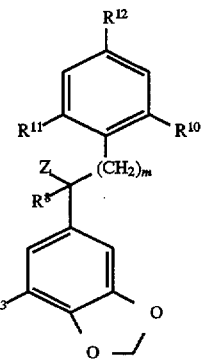

III$_b$ wherein the substituents are as defined in the table below:

| R$^3$ | R$^8$ | m | R$^{10}$ | R$^{11}$ | R$^{12}$ | Z |
|---|---|---|---|---|---|---|
| H | H | 1 | H | H | H | CO$_2$H |
| H | H | 1 | H | H | H | 4-i-Pr-PhenylSO$_2$NHCO— |
| H | H | 2 | H | H | H | CO$_2$H |

-continued

| $R^3$ | $R^8$ | m | $R^{10}$ | $R^{11}$ | $R^{12}$ | Z |
|---|---|---|---|---|---|---|
| H | H | 2 | H | H | H | 4-i-Pr-PhenylSO$_2$NHCO— |
| H | H | 1 | n-Pr | H | H | CO$_2$H |
| H | H | 1 | n-Pr | H | H | 4-i-Pr-PhenylSO$_2$NHCO— |
| H | H | 1 | n-Pr | n-Pr | H | CO$_2$H |
| H | H | 1 | n-Pr | n-Pr | H | 4-i-Pr-PhenylSO$_2$NHCO— |
| H | H | 1 | H | H | CO$_2$H | CO$_2$H |
| H | H | 1 | H | H | CO$_2$H | 4-i-Pr-PhenylSO$_2$NHCO— |
| H | H | 1 | n-Pr | H | CO$_2$H | CO$_2$H |
| H | H | 1 | n-Pr | H | CO$_2$H | 4-i-Pr-PhenylSO$_2$NHCO— |
| H | H | 1 | n-Pr | n-Pr | CO$_2$H | CO$_2$H |
| H | H | 1 | n-Pr | n-Pr | CO$_2$H | 4-i-Pr-PhenylSO$_2$NHCO— |
| H | CH$_3$ | 1 | H | H | H | CO$_2$H |
| H | CH$_3$ | 1 | H | H | H | 4-i-Pr-PhenylSO$_2$NHCO— |
| H | CH$_3$ | 1 | n-Pr | H | H | CO$_2$H |
| H | CH$_3$ | 1 | n-Pr | H | H | 4-i-Pr-PhenylSO$_2$NHCO— |
| H | CH$_3$ | 1 | n-Pr | n-Pr | H | CO$_2$H |
| H | CH$_3$ | 1 | n-Pr | n-Pr | H | 4-i-Pr-PhenylSO$_2$NHCO— |
| H | CH$_3$ | 1 | H | H | CO$_2$H | CO$_2$H |
| H | CH$_3$ | 1 | H | H | CO$_2$H | 4-i-Pr-PhenylSO$_2$NHCO— |
| H | CH$_3$ | 1 | n-Pr | H | CO$_2$H | CO$_2$H |
| H | CH$_3$ | 1 | n-Pr | H | CO$_2$H | 4-i-Pr-PhenylSO$_2$NHCO— |
| H | CH$_3$ | 1 | n-Pr | n-Pr | CO$_2$H | CO$_2$H |
| H | CH$_3$ | 1 | n-Pr | n-Pr | CO$_2$H | 4-i-Pr-PhenylSO$_2$NHCO— |
| H | H | 1 | n-Pr | H | CO$_2$H | PhenylSO$_2$NHCO— |
| H | H | 1 | n-Pr | H | CO$_2$H | 4-t-Bu-PhenylSO$_2$NHCO— |
| H | H | 1 | n-Pr | H | CO$_2$H | 4-Br-PhenylSO$_2$NHCO— |
| H | H | 1 | n-Pr | H | CO$_2$H | 4-CF$_3$-PhenylSO$_2$NHCO— |
| H | H | 1 | n-Pr | H | CO$_2$H | 2-(CO$_2$H)-PhSO$_2$NHCO— |
| H | H | 1 | n-Pr | H | CO$_2$H | Tetrazol-5-yl |
| H | H | 1 | n-Pr | H | CO$_2$H | Tetrazol-5-ylNHCO— |
| H | H | 1 | n-Pr | H | CO$_2$H | i-PrSO$_2$NHCO— |
| H | H | 1 | n-Pr | H | CO$_2$H | CH$_3$SO$_2$NHCO— |
| H | H | 1 | H | H | CF$_3$ | 4-i-Pr-PhenylSO$_2$NHCO— |
| H | H | 1 | H | H | CH$_2$OH | 4-i-Pr-PhenylSO$_2$NHCO— |
| H | H | 1 | H | H | OCH$_3$ | 4-i-Pr-PhenylSO$_2$NHCO— |
| H | H | 1 | H | H | Cl | 4-i-Pr-PhenylSO$_2$NHCO— |
| H | H | 1 | H | H | CO$_2$CH$_3$ | 4-i-Pr-PhenylSO$_2$NHCO— |
| H | H | 1 | n-Pr | H | CF$_3$ | 4-i-Pr-PhenylSO$_2$NHCO— |
| H | H | 1 | n-Pr | H | CH$_2$OH | 4-i-Pr-PhenylSO$_2$NHCO— |
| H | H | 1 | n-Pr | H | OCH$_3$ | 4-i-Pr-PhenylSO$_2$NHCO— |
| H | H | 1 | n-Pr | H | Cl | 4-i-Pr-PhenylSO$_2$NHCO— |
| H | H | 1 | n-Pr | H | CO$_2$CH$_3$ | 4-i-Pr-PhenylSO$_2$NHCO— |
| H | CH$_3$ | 1 | n-Pr | H | CF$_3$ | 4-i-Pr-PhenylSO$_2$NHCO— |
| H | CH$_3$ | 1 | n-Pr | H | CH$_2$OH | 4-i-Pr-PhenylSO$_2$NHCO— |
| H | CH$_3$ | 1 | n-Pr | H | OCH$_3$ | 4-i-Pr-PhenylSO$_2$NHCO— |
| H | CH$_3$ | 1 | n-Pr | H | Cl | 4-i-Pr-PhenylSO$_2$NHCO— |
| H | CH$_3$ | 1 | n-Pr | H | CO$_2$CH$_3$ | 4-i-Pr-PhenylSO$_2$NHCO— |
| 5-OCH$_3$ | H | 1 | n-Pr | H | CO$_2$H | 4-i-Pr-PhenylSO$_2$NHCO— |
| 5-OCH$_3$ | H | 1 | i-Bu | H | CO$_2$H | 4-i-Pr-PhenylSO$_2$NHCO— |
| 5-Cl | H | 1 | n-Pr | H | CO$_2$H | 4-i-Pr-PhenylSO$_2$NHCO— |
| 5-Cl | H | 1 | i-Bu | H | CO$_2$H | 4-i-Pr-PhenylSO$_2$NHCO— |
| 5-Br | H | 1 | n-Pr | H | CO$_2$H | 4-i-Pr-PhenylSO$_2$NHCO— |
| 5-Br | H | 1 | i-Bu | H | CO$_2$H | 4-i-Pr-PhenylSO$_2$NHCO— |
| 5-F | H | 1 | n-Pr | H | CO$_2$H | 4-i-Pr-PhenylSO$_2$NHCO— |
| 5-F | H | 1 | i-Bu | H | CO$_2$H | 4-i-Pr-PhenylSO$_2$NHCO— |
| 5-OCH$_3$ | CH$_3$ | 1 | n-Pr | H | CO$_2$H | 4-i-Pr-PhenylSO$_2$NHCO— |
| 5-OCH$_3$ | CH$_3$ | 1 | i-Bu | H | CO$_2$H | 4-i-Pr-PhenylSO$_2$NHCO— |
| 5-Cl | CH$_3$ | 1 | n-Pr | H | CO$_2$H | 4-i-Pr-PhenylSO$_2$NHCO— |
| 5-Cl | CH$_3$ | 1 | i-Bu | H | CO$_2$H | 4-i-Pr-PhenylSO$_2$NHCO— |
| H | H | 1 | n-Pr | H | CO$_2$H | 4-i-Pr-PhenylCONHSO$_2$— |
| H | H | 1 | n-Pr | H | CO$_2$H | 4-t-Pr-PhenylCONHSO$_2$— |
| H | H | 1 | n-Pr | H | CO$_2$H | PhenylCONHSO$_2$—. |

3. A compound of structural formula V:

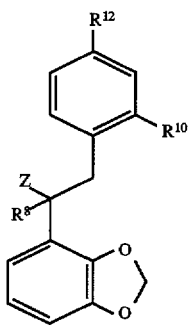

wherein the substituents are as defined in the table below:

| $R^8$ | $R^{10}$ | $R^{12}$ | Z |
|---|---|---|---|
| H | n-Pr | H | CO$_2$H |
| H | n-Pr | H | 4-i-Pr-PhenylSO$_2$NHCO— |
| H | H | CO$_2$H | CO$_2$H |
| H | H | CO$_2$H | 4-i-Pr-PhenylSO$_2$NHCO— |
| H | n-Pr | CO$_2$H | CO$_2$H |
| H | n-Pr | CO$_2$H | 4-i-Pr-PhenylSO$_2$NHCO— |
| CH$_3$ | H | H | CO$_2$H |
| CH$_3$ | H | H | 4-i-Pr-PhenylSO$_2$NHCO— |
| CH$_3$ | n-Pr | H | CO$_2$H |
| CH$_3$ | n-Pr | H | 4-i-Pr-PhenylSO$_2$NHCO— |
| CH$_3$ | H | CO$_2$H | CO$_2$H |
| CH$_3$ | H | CO$_2$H | 4-i-Pr-PhenylSO$_2$NHCO— |
| CH$_3$ | n-Pr | CO$_2$H | CO$_2$H |
| CH$_3$ | n-Pr | CO$_2$H | 4-i-Pr-PhenylSO$_2$NHCO— |
| H | n-Pr | CO$_2$H | PhenylSO$_2$NHCO— |
| H | n-Pr | CO$_2$H | 4-t-Bu-PhenylSO$_2$NHCO— |
| H | n-Pr | CO$_2$H | 4-Br-PhenylSO$_2$NHCO— |
| H | n-Pr | CO$_2$H | 4-CF$_3$-PhenylSO$_2$NHCO— |
| H | n-Pr | CO$_2$H | 2-(CO$_2$H)-PhenylSO$_2$NHCO— |
| H | n-Pr | CO$_2$H | Tetrazol-5-yl |
| H | n-Pr | CO$_2$H | Tetrazol-5-ylNHCO— |
| H | n-Pr | CO$_2$H | i-PrSO$_2$NHCO— |
| H | n-Pr | CO$_2$H | CH$_3$SO$_2$NHCO— |

-continued

| R⁸ | R¹⁰ | R¹² | Z |
|---|---|---|---|
| H | H | CF₃ | 4-i-Pr-PhenylSO₂NHCO— |
| H | H | CH₂OH | 4-i-Pr-PhenylSO₂NHCO— |
| H | H | OCH₃ | 4-i-Pr-PhenylSO₂NHCO— |
| H | H | Cl | 4-i-Pr-PhenylSO₂NHCO— |
| H | H | CO₂CH₃ | 4-i-Pr-PhenylSO₂NHCO— |
| H | n-Pr | CF₃ | 4-i-Pr-PhenylSO₂NHCO— |
| H | n-Pr | CH₂OH | 4-i-Pr-PhenylSO₂NHCO— |
| H | n-Pr | OCH₃ | 4-i-Pr-PhenylSO₂NHCO— |
| H | n-Pr | Cl | 4-i-Pr-PhenylSO₂NHCO— |
| H | n-Pr | CO₂CH₃ | 4-i-Pr-PhenylSO₂NHCO— |

4. A compound selected from the group consisting of:
N-[2-(3,4-methylenedioxyphenyl)-3-phenylpropanoyl]-4-(i-propyl)benzenesulfonamide;
N-[2-(3,4-methylenedioxyphenyl)-3-(4-trifluoromethylphenyl)-propanoyl]-4-(i-propyl)benzenesulfonamide;
N-[2-(3,4-methylenedioxyphenyl)-3-(4-carbomethoxy-2-propylphenyl)propanoyl]-4-(i-propyl)benzenesulfonamide;
N-[2-(3,4-methylenedioxyphenyl)-3-(4-carbomethoxy-2-propylphenyl)propanoyl]-4-(i-propyl)benzenesulfonamide;
N-[2-(3,4-methylenedioxyphenyl)-3-(4-carboxy-2-propylphenyl)-propanoyl]-4-(i-propyl)benzenesulfonamide;
N-[2-(3,4-methylenedioxyphenyl)-3-(3-methoxyphenyl)propanoyl]-4-(i-propyl)benzenesulfonamide potassium salt;
N-[2-(3,4-methylenedioxyphenyl)-3-(3,5-dimethoxyphenyl)propanoyl]-4-(i-propyl)benzenesulfonamide potassium salt;
N-[2-(3,4-methylenedioxyphenyl)-3-(4-nitrophenyl)propanoyl]-4-(i-propyl)benzenesulfonamide potassium salt;
N-[2-(3,4-methylenedioxyphenyl)-3-(4-aminophenyl)propanoyl]-4-(i-propyl)benzenesulfonamide trifluoroacetic acid salt;
N-[2-(3,4-methylenedioxyphenyl)-3-(2-ethoxyphenyl)propanoyl]-4-(i-propyl)benzenesulfonamide potassium salt;
N-[2-(3,4-methylenedioxyphenyl)-3-(3,4-methylenedioxyphenyl)-propanoyl]-4-(i-propyl)benzenesulfonamide potassium salt;
N-[2-(3,4-methylenedioxyphenyl)-3-(3-n-propyloxyphenyl)propanoyl]-4-(i-propyl)benzenesulfonamide potassium salt;
N-[2-(3,4-methylenedioxyphenyl)-3-(4-carbomethoxyphenyl)-propanoyl]-4-(i-propyl)benzenesulfonamide
N-[2-(3,4-methylenedioxyphenyl)-3-(4-carboxyphenyl)propanoyl]-4-(i-propyl)benzenesulfonamide dipotassium salt;
N-[2-(3,4-methylenedioxyphenyl)-3-(4-(2-carboxylphenyl)phenyl)-propanoyl]-4-(i-propyl)benzenesulfonamide dipotassium salt;
N-[2-(3,4-methylenedioxyphenyl)-3-(4-methylsulfonylphenyl)-propanoyl]-4-(i-propyl)benzenesulfonamide potassium salt;
N-[2-(3,4-methylenedioxyphenyl)-3-(2-naphthyl)propanoyl]-4-(i-propyl)benzenesulfonamide potassium salt; and
N-[2-(3,4-methylenedioxyphenyl)-3-(4-hydroxymethyl-2-propylphenyl)propanoyl]-4-(i-propyl)benzenesulfonamide;
N-(4-benzoyl)-[1-(3,4-methylenedioxyphenyl)-2-(4-carboxy-2-propylphenyl)ethane]sulfonamide;
N-(4-(i-propyl)benzoyl)-[1-(3,4-methylenedioxyphenyl)-2-(4-carboxy-2-propylphenyl)ethane]sulfonamide; and
N-(4-(t-butyl)benzoyl)-[1-(3,4-methylenedioxyphenyl)-2-(4-carboxy-2-propylphenyl)ethane]sulfonamide.

5. A compound which is: N-[2-(3,4-methylenedioxyphenyl)-3-(4-carboxy-2-propylphenyl)propanoyl]-4-(i-propyl)benzene-sulfonamide.

6. The compound of claim 1, of the structural Formula II:

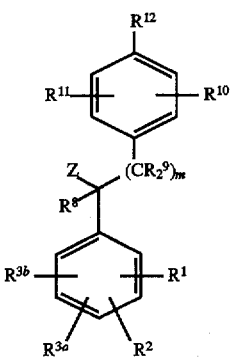

II or a pharmaceutically acceptable salt thereof, wherein:
R¹ and R² on adjacent carbon atoms are joined together to form a heterocyclic oxygen containing ring structure containing the following group —O—[C(R⁶)(R⁶)]—O—;

R³ᵃ and R³ᵇ are independently:
(a) H,
(b) F, Cl, Br, or I,
(c) —NO₂,
(d) —NH₂,
(e) —NH(C₁–C₄)-alkyl,
(f) —N[(C₁–C₄)-alkyl]₂,
(g) —SO₂NHR⁷,
(h) —CF₃,
(i) (C₁–C₄)-alkyl,
(j) —OR⁷,
(k) —S(O)ₙ—(C₁–C₄)-alkyl,
(l) —NHCO—(C₁–C₄)-alkyl,
(m) —NHCO—O(C₁–C₄)-alkyl,
(n) —CH₂O—(C₁–C₄)-alkyl,
(o) —O—(CH₂)ₓ—OR⁷,
(p) —CONR⁷R¹⁶, or
(q) —COOR⁷;

x is 2, 3 or 4,
n is 0, 1 or 2,
m is: 1 or 2;

R⁶ is:
(a) H,
(b) F, or
(c) (C₁–C₄)-alkyl unsubstituted or substituted with one or two substituents selected from the group consisting of:
i) —OH,
ii) —NR⁷R¹⁶,
iii) —COOR⁷,
iv) —CONHR⁷, or
v) —CONR⁷R¹⁶;

R⁷ is:
(a) H,
(b) (C₁–C₆)-alkyl,
(c) phenyl,
(d) benzyl, or
(e) (C₃–C₇)-cycloalkyl;

$R^8$ is:
(a) H,
(b) $(C_1-C_6)$-alkyl, unsubstituted or substituted with one or two substituents selected from the group consisting of:
  i) -phenyl,
  ii) $-(C_3-C_7)$-cycloalkyl,
  iii) $-NR^7R^{16}$,
  iv) -morpholin-4-yl,
  v) $-OH$,
  vi) $-CO_2R^7$, or
  vii) $-CON(R^7)_2$, or
(c) phenyl;

$R^9$ is:
(a) H,
(b) $(C_1-C_6)$-alkyl, unsubstituted or substituted with a substituent selected from the group consisting of:
  i) -phenyl,
  ii) $-(C_3-C_7)$-cycloalkyl,
  iii) $-NR^7R^{16}$,
  iv) $-OH$,
  v) $-O-(C_1-C_4)$-alkyl,
  vi) $-CF_3$,
  vii) $-COOR^7$,
  viii) $-S(O)_n-(C_1-C_4)$-alkyl, or
  ix) $-CON(R^7)_2$;
(c) $(C_3-C_7)$-cycloalkyl,
(d) F, Cl, Br, I,
(e) $-COOR^7$,
(f) $-CON(R^7)_2$,
(g) -perfluoro-$(C_1-C_4)$-alkyl,
(h) $-O-(CH_2)_x-OR^7$, or
(i) $-S(O)_n-(C_1-C_4)$-alkyl;

$R^{10}$ and $R^{11}$ are independently:
(a) H,
(b) $(C_1-C_6)$-alkyl, unsubstituted or substituted with $(C_3-C_7)$-cycloalkyl,
(c) $(C_2-C_6)$-alkenyl,
(d) $(C_2-C_6)$-alkynyl,
(e) Cl, Br, F, I,
(f) $(C_1-C_6)$-alkoxy,
(g) when $R^{10}$ and $R^{11}$ are on adjacent carbons, they can be joined to form a phenyl ring,
(h) perfluoro-$(C_1-C_6)$-alkyl,
(i) $(C_3-C_7)$-cycloalkyl, unsubstituted or substituted with $(C_1-C_6)$-alkyl,
(j) phenyl,
(k) $(C_1-C_6)$-alkyl-$S(O)_n-(CH_2)_n-$,
(l) hydroxy-$(C_1-C_6)$-alkyl,
(m) $-CF_3$,
(n) $-CO_2R^7$,
(o) $-OH$,
(p) $-NR^7R^{16}$,
(q) $-[(C_1-C_6)$-alkyl$]NR^7R^{16}$,
(r) $-NO_2$,
(s) $-(CH_2)_n-SO_2-N(R^7)_2$,
(t) $-NR^7CO-(C_1-C_4)$-alkyl,
(u) $-CON(R^7)_2$, or
(v) when $R^{10}$ and $R^{11}$ are on adjacent carbons, they can join together to form a ring, where $R^{10}$ and $R^{11}$ are represented by $-O-CH_2-O-$;

$R^{12}$ is:
(a) H
(b) $(C_1-C_6)$-alkyl, unsubstituted or substituted with one or two substituents selected from the group consisting of:
  i) $-OH$,
  ii) $-O-(C_1-C_4)$-alkyl,
  iii) $-O-(C_1-C_4)$-cycloalkyl,
  iv) $-S(O)_n-(C_1-C_4)$-alkyl,
  iv) $-NR^7-(C_1-C_4)$-alkyl,
  v) $-NR^7R^{16}$,
  vi) $-COOR^7$,
  vii) $-CONHR^7$,
  viii) $-OCOR^{16}$,
  ix) $-CONR^7R^{16}$,
  x) $-NR^7CONR^7R^{16}$,
  xi) $-NR^7COOR^{16}$,
  xii) $-C(R^6)(OH)-C(R^6)(R^7)(OH)$, or
  xiii) $-SO_2NR^7R^{16}$,
(c) $(C_3-C_7)$-cycloalkyl,
(d) $-C(R^6)(OH)-C(R^6)(R^7)(OH)$,
(e) -perfluoro-$(C_1-C_4)$-alkyl,
(f) $-OR^7$,
(g) $-COOR^{13}$,
(h) $-COR^{16}$,
(i) $-CONR^7R^{16}$,
(j) $-CONHSO_2R^{16}$;
(k) $-NO_2$,
(l) $-NH_2$,
(m) $-NR^7R^{16}$,
(n) $-NR^7CONR^7R^{16}$,
(o) $-NR^7COOR^{16}$,
(p) $-NR^7COR^{16}$,
(q) $-NR^7CONHSO_2R^{16}$,
(r) $-NR^7SO_2R^{16}$,
(s) $-NR^7SO_2NH_2$,
(t) $-NR^7SO_2NHR^{16}$,
(u) $-NR^7SO_2N(R^{16})_2$,
(v) $-NR^7SO_2NHCOR^{16}$,
(w) $-SO_2NR^7R^{16}$,
(x) $-S(O)_2-NR^7COR^{16}$,
(y) $-S(O)_2-NR^7COOR^{16}$,
(z) $-S(O)_2-NR^7CONHR^{16}$,
(aa) $-S(O)_2-NR^7CONH_2$, or
(ab) $-S(O)_n-(C_1-C_4)$-alkyl;

Z is:
(a) $-CO_2R^{13}$,
(b) $-CONH$-(tetrazol-5-yl),
(c) $-CONHSO_2$-phenyl, wherein phenyl is unsubstituted or substituted with one or two substituents selected from the group consisting of:
  i) $(C_1-C_4)$-alkyl,
  ii) $-O-(C_1-C_4)$-alkyl,
  iii) $-CONR^7R^{16}$,
  iv) F, Cl, Br or I,
  v) $-COOR^7$,
  vi) $(C_1-C_4)$-perfluoroalkyl,
  vii) $(C_3-C_7)$-cycloalkyl,
  viii) $NR^7R^{16}$,
  ix) $SO_2NR^7R^{16}$,
  x) hydroxy, or
  xi) 2,3-, or 3,4-methylenedioxy;
(d) $-CONHSO_2-(C_1-C_8)$-alkyl, wherein the alkyl group is unsubstituted or substituted with one or two substituents selected from the group consisting of:
  i) $-OH$,
  ii) $-O-(C_1-C_4)$-alkyl,
  iii) $-S(O)_n-(C_1-C_4)$-alkyl,
  iv) $-NR^7-(C_1-C_4)$-alkyl,
  v) $-NHR^7$,
  vi) $-COOR^7$,
  vii) $-CONHR^7$,
  viii) $-OCOR^{16}$, or ix) —CONR⁷R¹⁶,
(e) —CONHSO₂—(C₁-C₄)-perfluoroalkyl,
(f) —CONHSO₂—(C₃-C₇)-cycloalkyl,
(g) —CONHSO₂-heteroaryl, wherein heteroaryl is defined as furyl, unsubstituted or substituted with (C₁-C₆)-alkyl,
(h) -tetrazol-5-yl,
—CONHSO₂NH-phenyl, wherein phenyl is unsubstituted or substituted with one or two substituents selected from the group consisting of:
i) (C₁-C₄)-alkyl,
ii) —O—(C₁-C₄)-alkyl,
iii) —CONR⁷R¹⁶,
iv) F, Cl, Br or I,
v) —COOR⁷,
vi) (C₁-C₄)-perfluoroalkyl,
vii) (C₃-C₇)-cycloalkyl,
viii) NR⁷R¹⁶,
ix) SO₂NR⁷R¹⁶,
x) hydroxy, or
xi) 2,3-, or 3,4-methylenedioxy;
(j) —CONHSO₂NH—(C₁-C₈)-alkyl, wherein the alkyl group is unsubstituted or substituted as defined in Z(d),
(k) —CONHSO₂NH—(C₁-C₄)-perfluoroalkyl,
(l) —CONHSO₂NH—(C₃-C₇)-cycloalkyl,
(m) —CONHSO₂NH-heteroaryl, wherein heteroaryl is defined as furyl, thienyl, pyrrolyl, isothiazolyl, imidazolyl, isoxazolyl, thiazolyl, oxazolyl, pyrazolyl, pyrazinyl, pyridyl, pyrimidyl, purinyl, quinolinyl, or carbazolyl, unsubstituted or substituted with (C₁-C₆)-alkyl;
(n) —SO₂NHCO-phenyl, wherein phenyl is as defined in Z(c) above,
(o) —SO₂NHCO—(C₁-C₈)-alkyl, wherein the alkyl group is unsubstituted or substituted as defined in Z(d),
(p) —SO₂NHCO—(C₁-C₄)-perfluoroalkyl,
(q) —SO₂NHCO-heteroaryl, wherein heteroaryl is as defined in Z(g) above,
(r) —SO₂NHCON(R¹⁶)₂ wherein the R⁶ groups are the same or different,
(s) —SO₂NHCOOR¹⁶,
(t) —PO(OR⁷)₂, wherein the R⁷ groups are the same or different, or
(u) —PO(R¹⁶)OR⁷;
R¹³ is:
(a) H,
(b) (C₁-C₆)-alkyl,
(c) CHR¹⁴—O—COR¹⁵,
(d) CH₂CH₂—N[(C₁-C₂)-alkyl]₂,
(e) CH₂CH₂—N[CH₂CH₂]₂O,
(f) (CH₂CH₂O)ᵧ—O—[(C₁-C₄)-alkyl], wherein y is 1 or 2,
(g) phenyl, naphthyl, CH₂-phenyl or CH₂-naphthyl, where phenyl or naphthyl is substituted or unsubstituted with CO₂—(C₁-C₆)-alkyl,

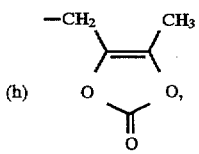

(h)

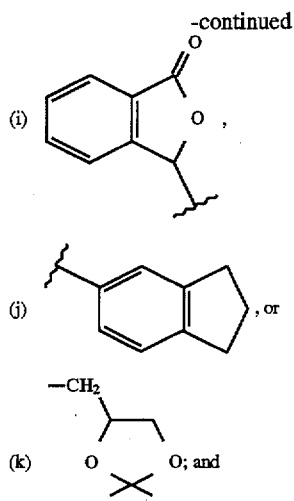

(i)

(j)

(k)

R¹⁴ and R¹⁵ independently are (C₁-C₆)-alkyl or phenyl; and
R¹⁶ is
(a) —(C₁-C₆)-alkyl,
(b) —(C₁-C₄)-perfluoroalkyl,
(c) —(C₁-C₄)-polyfluoroalkyl,
(d) -phenyl, unsubstituted or substituted with a substituent selected from the group consisting of:
i) (C₁-C₄)-alkyl,
ii) —O—(C₁-C₄)-alkyl,
iii) —CONR⁷R¹⁶,
iv) F, Cl, Br or I,
v) —COOR⁷,
(e) —(C₁-C₄)-alkyl-phenyl, wherein the phenyl is unsubstituted or substituted with a substituent selected from the group consisting of:
i) (C₁-C₄)-alkyl,
ii) —O—(C₁-C₄)-alkyl,
iii) —CONR⁷R¹⁶,
iv) F, Cl, Br or I,
v) —COOR⁷, or
(f) —(C₃-C₇)-cycloalkyl.

7. The compound of claim 6 of the structural Formula III:

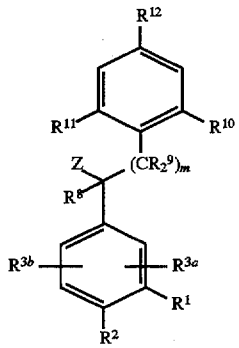

or a pharmaceutically acceptable salt thereof, wherein:
R¹ and R² on adjacent carbon atoms are joined together to form a heterocyclic oxygen containing ring structure containing the following group —O—[C(R⁶)(R⁶)]—O—;
R³ᵃ and R³ᵇ are independently:
(a) H,
(b) F, Cl, Br, or I,
(c) —NO₂, (d) $(C_1-C_4)$-alkyl,
(e) —$OR^7$,
(f) —NHCO—$(C_1-C_4)$-alkyl,
(g) —NHCO—$O(C_1-C_4)$-alkyl,
(h) —O—$(CH_2)_x$—$OR^7$,
(i) —$CONR^7R^{16}$, or
(j) —$COOR^7$;

x is 2, 3 or 4, m is: 1 or 2;

n is 0, 1 or 2, $R^6$ is:
(a) H, or
(b) F, or
(c) $(C_1-C_4)$-alkyl;

$R^7$ is:
(a) H,
(b) $(C_1-C_6)$-alkyl,
(c) phenyl, or
(d) benzyl;

$R^8$ is:
(a) H,
(b) $(C_1-C_6)$-alkyl, or
(c) phenyl;

$R^9$ is:
(a) H,
(b) $(C_1-C_6)$-alkyl, unsubstituted or substituted with a substituent selected from the group consisting of:
  i) -phenyl,
  ii) —$(C_3-C_7)$-cycloalkyl,
  iii) —OH, or
  iv) —O—$(C_1-C_4)$-alkyl;
(c) F, Cl, Br, I,
(d) —$COOR^7$,
(e) —O—$(CH_2)_x$—$OR^7$, or
(f) —$S(O)_n$—$(C_1-C_4)$-alkyl;

$R^{10}$ and $R^{11}$ are independently:
(a) H,
(b) $(C_1-C_6)$-alkyl, unsubstituted or substituted with $(C_3-C_7)$-cycloalkyl,
(c) Cl, Br, F, I,
(d) $(C_1-C_6)$-alkoxy,
(e) hydroxy-$(C_1-C_6)$-alkyl, or
(f) —$CO_2R^7$;

$R^{12}$ is
(a) H,
(b) $(C_1-C_6)$-alkyl, wherein alkyl is defined as unsubstituted or substituted with one or two substituents selected from the group consisting of:
  i) —OH,
  ii) —O—$(C_1-C_4)$-alkyl,
  iii) —$S(O)_n$—$(C_1-C_4)$-alkyl,
  iv) —$NR^7R^{16}$,
  v) —$COOR^7$,
  vi) —$CONHR^7$, or
  vii) —$OCOR^{16}$,
(c) —$COOR^{13}$,
(d) —$CONR^7R^{16}$,
(e) —$C(R^6)(OH)$—$C(R^6)(R^7)(OH)$,
(f) —$CONHSO_2R^{16}$,
(g) $NO_2$,
(h) $NH_2$,
(i) $OR^7$, or
(j) perfluoro-$(C_1-C_4)$-alkyl;

Z is:
(a) —$CO_2R^{13}$,
(b) —CONH-(tetrazol-5-yl),
(c) —$CONHSO_2$-phenyl, wherein phenyl is unsubstituted or substituted with one or two substituents selected from the group consisting of:
  i) $(C_1-C_4)$-alkyl,
  ii) —O—$(C_1-C_4)$-alkyl,
  iii) —$CONR^7R^{16}$,
  iv) F, Cl, Br or I,
  v) —$COOR^7$,
  vi) $(C_1-C_4)$-perfluoroalkyl,
  vii) $(C_3-C_7)$-cycloalkyl,
  viii) $NR^7R^{16}$,
  ix) $SO_2NR^7R^{16}$,
  x) hydroxy,
  xi) 2,3-, or 3,4-methylenedioxy;
(d) —$CONHSO_2$—$(C_1-C_8)$-alkyl, wherein alkyl is unsubstituted or substituted with one or two substituents selected from the group consisting of:
  i) —OH,
  ii) —O—$(C_1-C_4)$-alkyl,
  iii) —$S(O)_n$—$(C_1-C_4)$-alkyl,
  iv) —$NR^7$—$(C_1-C_4)$-alkyl,
  v) —$NHR^7$,
  vi) —$COOR^7$,
  vii) —$CONHR^7$,
  viii) —$OCOR^{16}$, or
  ix) —$CONR^7R^{16}$,
(e) $CONHSO_2$—$(C_1-C_4)$-perfluoroalkyl,
(f) —$CONHSO_2$—$(C_3-C_7)$-cycloalkyl,
(g) —$CONHSO_2$-heteroaryl, wherein heteroaryl is defined as furyl,
(h) —$CONHSO_2NH$-phenyl, wherein phenyl is unsubstituted or substituted with one or two substituents selected from the group consisting of:
  i) $(C_1-C_4)$-alkyl,
  ii) —O—$(C_1-C_4)$-alkyl,
  iii) —$CONR^7R^{16}$,
  iv) F, Cl, Br or I,
  v) —$COOR^7$,
  vi) $(C_1-C_4)$-perfluoroalkyl,
  vii) $(C_3-C_7)$-cycloalkyl,
  viii) $NR^7R^{16}$,
  ix) $SO_2NR^7R^{16}$,
  x) hydroxy, or
  xi) 2,3-, or 3,4-methylenedioxy;
(i) —$SO_2NHCO$-phenyl, wherein phenyl is as defined in Z(c) above,
-tetrazol-5-yl; and $R^{16}$ is
(a) $(C_1-C_6)$-alkyl,
(b) phenyl,
(c) —$(C_1-C_4)$-alkyl-phenyl, or
(d) $(C_3-C_7)$-cycloalkyl.

8. The compound of claim 6 of the structural Formula V:

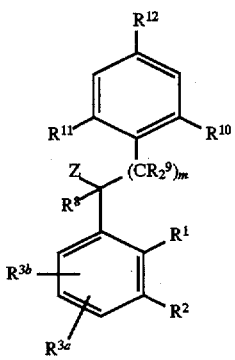

or a pharmaceutically acceptable salt thereof, wherein:

$R^1$ and $R^2$ on adjacent carbon atoms are joined together to form a heterocyclic oxygen containing ring structure containing the following group —O—[C(R$^6$)(R$^6$)]—O—;

$R^{3a}$ and $R^{3b}$ are independently:
  (a) H,
  (b) F, Cl, Br, or I,
  (c) —NO$_2$,
  (d) (C$_1$–C$_4$)-alkyl,
  (e) —OR$^7$,
  (f) —NHCO—(C$_1$–C$_4$)-alkyl,
  (g) —NHCO—O(C$_1$–C$_4$)-alkyl,
  (h) —O—(CH$_2$)$_x$—OR$^7$,
  (i) —CONR$^7$R$^{16}$, or
  (j) —COOR$^7$;

x is 2, 3 or 4, m is: 1 or 2;

n is 0, 1 or 2, $R^6$ is:
  (a) H,
  (b) F, or
  (c) (C$_1$–C$_4$)-alkyl;

$R^7$ is:
  (a) H,
  (b) (C$_1$–C$_6$)-alkyl,
  (c) phenyl, or
  (d) benzyl;

$R^8$ is:
  (a) H,
  (b) (C$_1$–C$_6$)-alkyl, or
  (c) phenyl;

$R^9$ is:
  (a) H,
  (b) (C$_1$–C$_6$)-alkyl unsubstituted or substituted with a substituent selected from the group consisting of:
    i) -phenyl,
    ii) —(C$_3$–C$_7$)-cycloalkyl,
    iii) —OH, or
    iv) —O—(C$_1$–C$_4$)-alkyl;
  (c) F, Cl, Br, I,
  (d) —COOR$^7$,
  (e) —O—(CH$_2$)$_x$—OR$^7$, or
  (f) —S(O)$_n$—(C$_1$–C$_4$)-alkyl;

$R^{10}$ and $R^{11}$ are independently:
  (a) H,
  (b) (C$_1$–C$_6$)-alkyl, unsubstituted or substituted with (C$_3$–C$_7$)cycloalkyl,
  (c) Cl, Br, F, I,
  (d) (C$_1$–C$_6$)-alkoxy,
  (e) hydroxy-(C$_1$–C$_6$)-alkyl, or
  (f) —CO$_2$R$^7$, $R^{12}$ is
  (a) H,
  (b) (C$_1$–C$_6$)-alkyl, wherein alkyl is defined as unsubstituted or substituted with one or two substituents selected from the group consisting of:
    i) —OH,
    ii) —O—(C$_1$–C$_4$)-alkyl,
    iii) —S(O)$_n$—(C$_1$–C$_4$)-alkyl,
    iv) —NR$^7$R$^{16}$,
    v) —COOR$^7$,
    vi) —CONHR$^7$, or
    vii) —OCOR$^{16}$,
  (c) —COOR$^{13}$,
  (d) —CONR$^7$R$^{16}$,
  (e) —C(R$^6$)(OH)—C(R$^6$)CR$^7$)(OH),
  (f) —CONHSO$_2$R$^{16}$,
  (g) NO$_2$,
  (h) NH$_2$,
  (i) OR$^7$, or
  (j) perfluoro-(C$_1$–C$_4$)-alkyl;

Z is:
  (a) —CO$_2$R$^{13}$,
  (b) —CONH-(tetrazol-5-yl),
  (c) —CONHSO$_2$-phenyl, wherein phenyl is unsubstituted or substituted with one or two substituents selected from the group consisting of:
    i) (C$_1$–C$_4$)-alkyl,
    ii) —O—(C$_1$–C$_4$)-alkyl,
    iii) —CONR$^7$R$^{16}$,
    iv) F, Cl, Br or I,
    v) —COOR$^7$,
    vi) (C$_1$–C$_4$)-perfluoroalkyl,
    vii) (C$_3$–C$_7$)-cycloalkyl,
    viii) NR$^7$R$^{16}$,
    ix) SO$_2$NR$^7$R$^{16}$,
    x) hydroxy,
    xi) 2,3-, or 3,4-methylenedioxy;
  (d) —CONHSO$_2$—(C$_1$–C$_8$)-alkyl, wherein alkyl is unsubstituted or substituted with one or two substituents selected from the group consisting of:
    i) —OH,
    ii) —O—(C$_1$–C$_4$)-alkyl,
    iii) —S(O)$_n$—(C$_1$–C$_4$)-alkyl,
    iv) —NR$^7$—(C$_1$–C$_4$)-alkyl,
    v) —NHR$^7$,
    vi) —COOR$^7$,
    vii) —CONHR$^7$,
    viii) —OCOR$^{16}$, or
    ix) —CONR$^7$R$^{16}$,
  (e) —CONHSO$_2$—(C$_1$–C$_4$)-perfluoroalkyl,
  (f) —CONHSO$_2$—(C$_3$–C$_7$)-cycloalkyl,
  (g) —CONHSO$_2$-heteroaryl, wherein heteroaryl is defined as furyl, or
  (h) -tetrazol-5-yl; and $R^{16}$ is
  (a) (C$_1$–C$_6$)-alkyl,
  (b) phenyl,
  (c) —(C$_1$–C$_4$)-alkyl-phenyl, or
  (d) (C$_3$–C$_7$)-cycloalkyl.

9. A method of treating a condition in a mammal, the treatment of which is effected or facilitated by a decrease in endothelin mediated actions, comprising the administration, in an amount that is effective for antagonizing the effect of endothelin, of a compound of Formula I as recited in claim 1.

10. The method as recited in claim 9 wherein the condition is hypertension.

11. The method as recited in claim 10 wherein the mammal is human.

12. A method of treating cardiovascular disorders by administering to a person in need of such treatment a therapeutically effective amount of a compound of Formula I as recited in claim 1.

13. The method as recited in claim 9 wherein the condition is benign prostatic hyperplasia.

14. The method as recited in claim 13 wherein the mammal is human.

15. A method of treating benign prostatic hyperplasia by administering to a person in need of such treatment a therapeutically effective amount of a compound of Formula I as recited in claim 1.

16. The method as recited in claim 9 comprising a pharmaceutical composition of therapeutically effective amount of the compound of Formula I and a pharmaceutically acceptable carrier.

17. A pharmaceutical formulation for the treatment of hypertension comprising a pharmaceutically acceptable carrier and an effective amount of the compound of Formula I as recited in claim 1.

18. A pharmaceutical formulation for the treatment of pulmonary hypertension comprising a pharmaceutically acceptable carrier and an effective amount of the compound of Formula I as recited in claim 1.

19. A pharmaceutical formulation for the treatment of asthma comprising a pharmaceutically acceptable carrier and an effective amount of the compound of claim 1.

20. A pharmaceutical composition for antagonizing the effect of endothelin, comprising a pharmaceutically acceptable carrier and a pharmaceutically effective amount of the compound of Formula I as recited in claim 1.

* * * * *